(12) United States Patent  (10) Patent No.: US 8,664,955 B1
Halpern  (45) Date of Patent: Mar. 4, 2014

(54) HIGH-ISOLATION TRANSMIT/RECEIVE SURFACE COILS AND METHOD FOR EPRI

(76) Inventor: Howard J. Halpern, Chicago, IL (US)

(*) Notice: Subject to any disclaimer, the term of this patent is extended or adjusted under 35 U.S.C. 154(b) by 404 days.

(21) Appl. No.: 13/032,626

(22) Filed: Feb. 22, 2011

Related U.S. Application Data

(60) Provisional application No. 61/306,917, filed on Feb. 22, 2010, provisional application No. 61/356,555, filed on Jun. 18, 2010, provisional application No. 61/445,037, filed on Feb. 21, 2011.

(51) Int. Cl.
G01V 3/00 (2006.01)
(52) U.S. Cl.
USPC ............................ 324/316; 324/318; 600/410
(58) Field of Classification Search
USPC .................................. 324/316, 318; 600/410
See application file for complete search history.

(56) References Cited

U.S. PATENT DOCUMENTS

| | | | |
|---|---|---|---|
| 4,280,096 A | 7/1981 | Karthe et al. | |
| 4,714,886 A | 12/1987 | Halpern | |
| 4,812,763 A | 3/1989 | Schmalbein | |
| 5,706,805 A | 1/1998 | Swartz et al. | |
| 5,828,216 A | 10/1998 | Tschudin et al. | |
| 5,865,746 A | 2/1999 | Murugesan et al. | |
| 6,150,817 A * | 11/2000 | Lurie et al. | 324/318 |
| 6,639,406 B1 | 10/2003 | Boskamp et al. | |
| 6,977,502 B1 | 12/2005 | Hertz | |
| 7,659,719 B2 | 2/2010 | Vaughan et al. | |
| 7,710,117 B2 | 5/2010 | Vaughan et al. | |
| 7,800,368 B2 | 9/2010 | Vaughan et al. | |
| 2006/0264738 A1* | 11/2006 | Hashimshony et al. | 600/410 |

OTHER PUBLICATIONS

Halpern, Howard J., et al., "Rapid quantitation of parameters from inhomogeneously broadened EPR spectra", "Journal of Magnetic Resonance", 1993, pp. 13-22, vol. A 103.
Blasberg, et al., "Molecular-genetic imaging: current and future perspectives", "The Journal of Clinical Investigation", Jun. 2003, pp. 1620-1629, vol. 111, No. 11.
Bremer, et al., "Optical imaging of matrix metalloproteinase-2 activity in tumors: feasibility study in a mouse model", "Radialogy", Nov. 2001, pp. 523-529, vol. 221, No. 2.

(Continued)

Primary Examiner — Melissa Koval
Assistant Examiner — Rishi Patel
(74) Attorney, Agent, or Firm — Charles A. Lemaire; Jonathan M. Rixen; Lemaire Patent Law Firm, P.L.L.C.

(57) ABSTRACT

The present invention provides an apparatus and a corresponding method useful for electron paramagnetic resonance imaging, in situ and in vivo, using high-isolation transmit/receive (TX/RX) coils, which, in some embodiments, provide microenvironmental images that are representative of particular internal structures in the human body and spatially resolved images of tissue/cell protein signals responding to conditions (such as hypoxia) that show the temporal sequence of certain biological processes, and, in some embodiments, that distinguish malignant tissue from healthy tissue. In some embodiments, the TX/RX coils are in a surface, volume or surface-volume configuration. In some embodiments, the transmit coils are oriented to generate an RF magnetic field in directions substantially orthogonal to a static gradient field, and the receive coils are oriented to sense RF EPR signal in directions substantially orthogonal to the transmitted field and to the static field, to minimize coupling of the transmitted signal to the receive coils.

20 Claims, 32 Drawing Sheets
(14 of 32 Drawing Sheet(s) Filed in Color)

(56) References Cited

OTHER PUBLICATIONS

Brizel, D. et al., "Tumor oxygenation predicts for the likelihood of distant metastases in human soft tissue sarcoma", "Cancer Res", 1996, pp. 941-943, vol. 56.

Burks, et al., "Optimization of labile esters for esterase-assisted accumulation of nitroxides into cells: a model for in vivo EPR imagi", "Bioconjug Chem", Oct. 2008, pp. 2068-2071, vol. 19, No. 10.

Chalfie, et al., "Green fluorescent protein as a marker for gene expression", "Science", Feb. 11, 1994, pp. 802-805, vol. 263.

Dewhirst, et al., "Microvascular studies on the origins of perfusion-limited hypoxia", "British Journal of Cancer", 1996, pp. S247-S251, vol. 74.

Dothager, et al., "Molecular imaging of pulmonary disease in vivo", "Proceedings of the American Thoracic Society", 2009, pp. 403-410, vol. 6.

Elas, et al., "Electron paramagnetic resonance oxygen images correlate spatially and quantitatively with Oxylite oxygen measurements", "Clin Cancer Res", 2006, pp. 4209-4217, vol. 12.

Epel, Boris J., et al., "A Versatile High Speed 250-MHz Pulse Imager for Biomedical Applications", "Magn. Reson. Part B (Magn. Reson. Engineering)", 2008, pp. 163-176, vol. 33B.

Evans, et al., "2-Nitroimidazole (EF5) binding predicts radiation resistance in individual 9L s.c. tumors", "Cancer Research", Jan. 15, 1996, pp. 405-411, vol. 56.

Fink, et al., "Identification of a tightly regulated hypoxia-response element in the promoter of human plasminogen activator inhibitor-", "Blood", Mar. 15, 2002, pp. 2077-2083, vol. 99, No. 6.

Fischbach, et al., "Cancer cell angiogenic capability is regulated by 3D culture and integrin engagement", 2009, pp. 399-404, vol. 106, No. 2, Publisher: Proc Natl Acad Sci.

Gillespie, et al., "Silencing of hypoxia inducible factor-1alpha by RNA interference attenuates human glioma cell growth in vivo", "Clin. Cancer Res.", 2007, pp. 2441-2448.

Halpern, et al., "Oxymetry deep in tissues with low-frequency electron paramagnetic resonance", "Proc. Natl. Acad. Sci.", Dec. 1994, pp. 13047-13051, vol. 91.

Halpern, Howard J., et al., "Imaging radio frequency electron-spin-resonance spectrometer with high resolution and sensitivity for in vivo measuremen", "Rev. Sci. Instrum.", Jun. 1989, pp. 1040-1050, vol. 60, No. 6.

Haney, et al., "Reduction of image artifacts in mice by bladder flushing with a novel double-lumen urethral catheter", Jul. 2006, pp. 175-179, vol. 5, No. 3, Publisher: Mol Imaging.

Hockel, M. et al., "Association between tumor hypoxia and malignant progression in advanced cancer of the uterine cervix.", "Cancer Res", 1996, pp. 4509-4515, vol. 56.

Lewis, et al., "Evaluation of 64Cu-ATSM in vitro and in vivo in a hypoxic tumor model", "The Journal of Nuclear Medicine", Jan. 1999, pp. 177-183, vol. 40, No. 1.

Lungu, et al., "In vivo imaging and characterization of hypoxia-induced neovascularization and tumor invasion", "International Journal of Oncology", 2007, pp. 45-54, vol. 30.

Massoud, et al., "Molecular imaging in living subjects: seeing fundamental biological processes in a new light", "Genes and Development", 2003, pp. 545-580.

McCaffrey, et al., "Advancing molecular therapies through in vivo bioluminescent imaging", "Molecular Imaging", Apr. 2003, pp. 75-86, vol. 2, No. 2.

Mechtcheriakova, et al., "Vascular endothelial cell growth factor-induced tissue factor expression in endothelial cells is mediated by EGR-1", "Blood", Jun. 1999, pp. 3811-3823, vol. 93, No. 11.

Shibata, et al., "Development of a hypoxia-responsive vector for tumor-specific gene therapy", "Gene Therapy", 2000, pp. 493-498, vol. 7.

Shibata, T., et al., "Hypoxia-inducible regulation of a prodrug-activating enzyme for tumor-specific gene therapy.", "Neoplasia", 2002, pp. 40-48, vol. 4.

Studholme, et al., "Automated 3-D registration of MR and CT images of the head", "Medical Image Analysis", 1996, pp. 163-175, vol. 1, No. 2.

Studholme, et al., "Automated three-dimensional registration of magnetic resonance and positron emission tomography brain images by multires", "Med. Phys.", Jan. 1997, vol. 24, No. 1.

Sun, et al., "Quantitative imaging of gene induction in living animals", "Gene Therapy", 2001, pp. 1572-1579, vol. 8.

Thurston, et al., "VEGF and Delta-Notch: interacting signalling pathways in tumour angiogenesis", "British Journal of Cancer ", 2008, pp. 1204-1209, vol. 99, No. 8.

Timke, et al., "Combination of vascular endothelial growth factor receptor/platelet-derived growth factor receptor inhibition markedly i", "Clinical Cancer Research", 2008, pp. 2210-2219.

Weissleder, et al., "Shedding light onto live molecular targets", "Nature Medicine", Jan. 2003, pp. 123-128, vol. 9, No. 1.

Weissleder, et al, "In vivo magnetic resonance imaging of transgene expression", "Nature Medicine", Mar. 2000, pp. 351-355, vol. 6, No. 3.

Wells, et al., "Multi-modal volume registration by maximization of mutual information", "Medical Image Analysis", 1996, pp. 35-51, vol. 1, No. 1.

Beekman, et al., "The pinhole: gateway to ultra-high-resolution three-dimensional radionuclide imaging", "Eur J Nucl Med Mol Imaging", 2007, pp. 151-161, vol. 34, No. 2.

Adriany, et al., "A Geometrically Adjustable 16-Channel Transmit/Receive Transmission Line Array for Improved RF Efficiency and Parallel . . . ", "Magnetic Resonance in Medicine", 2008, pp. 590-597, vol. 59.

Halpern, Howard J., "Stable soluble paramagnetic compounds", "In: L.J. Berliner, Ed., In Vivo EPR(ESR): Theory and Applications, vol. 18. Chapter 8.", 2003, Publisher: Kluwer Academic/Plenum Pub. Corp, New York.

Halpern, Howard J., "Cancer Research", "In: L.J. Berliner, Ed., In Vivo EPR(ESR): Theory and Applications, vol. 18. Chapter 17.", 2003, Publisher: Kluwer Academic/Plenum Pub. Corp, New York.

Halpern, Howard J., et al., "Low-Frequency EPR Spectrometers: MHz Range", "In: L.J. Berliner, Ed., In Vivo EPR(ESR): Theory and Applications, vol. 18. Chapter 6.", 2003, pp. 45-62, Publisher: Kluwer Academic/Plenum Pub. Corp, New York.

Vaughan, J.T., et al., "Clinical Imaging at 7T with a 16 Channel Whole Body Coil and 32 Receive Channels.", "Proceedings 17th Scientific Meeting, International Society for Magnetic Resonance in Medicine", Apr. 2009, p. 392.

\* cited by examiner

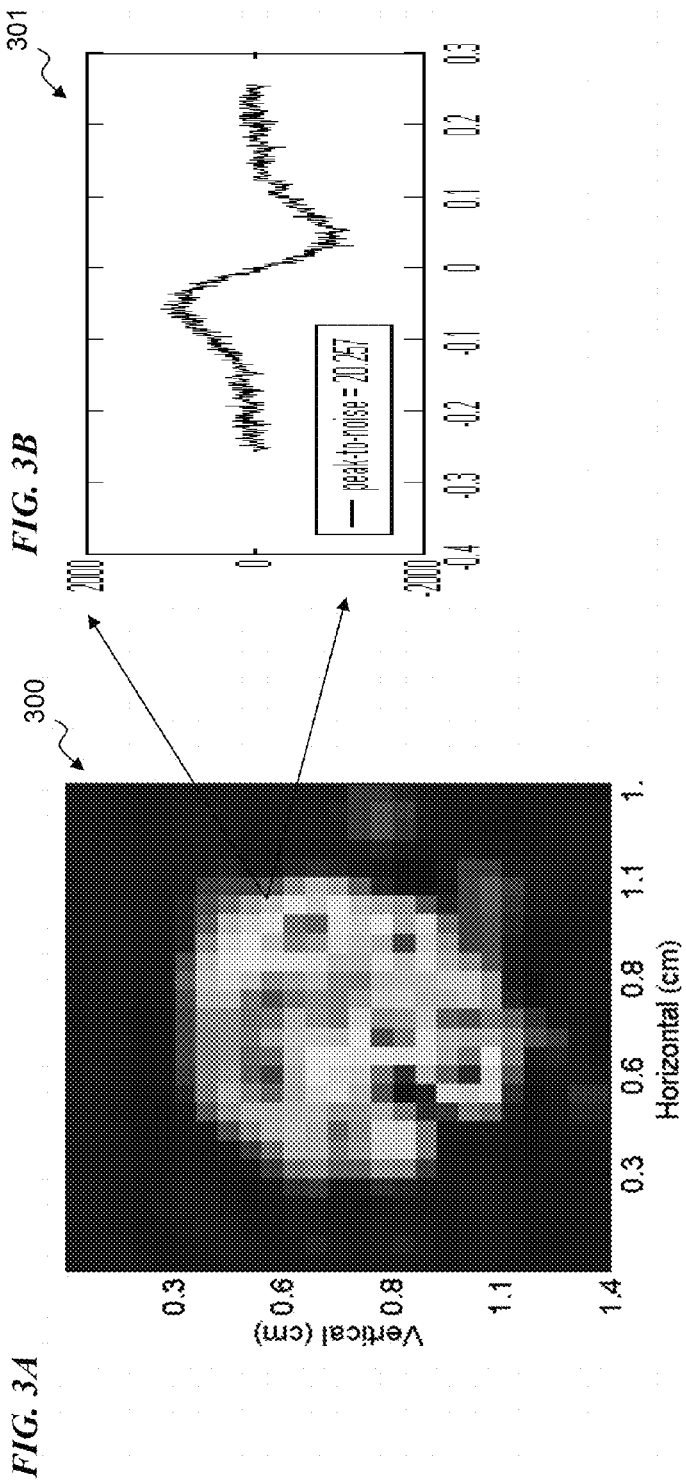
*FIG. 3A*
*FIG. 3B*
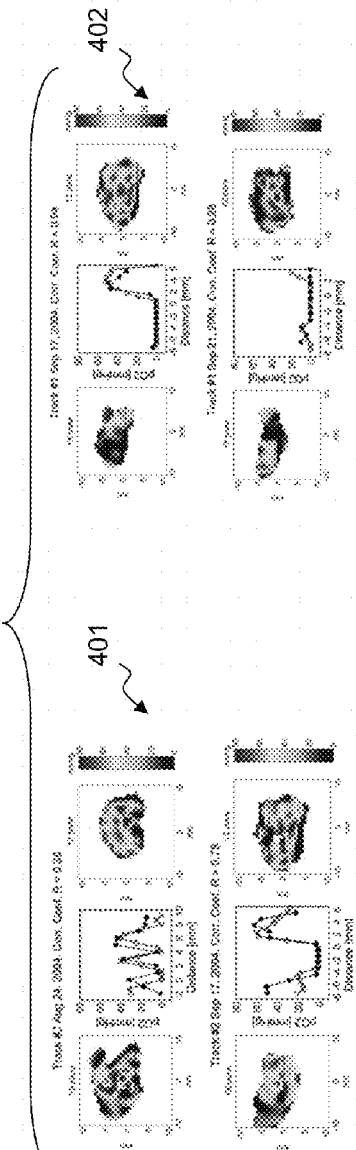
*FIG. 4*

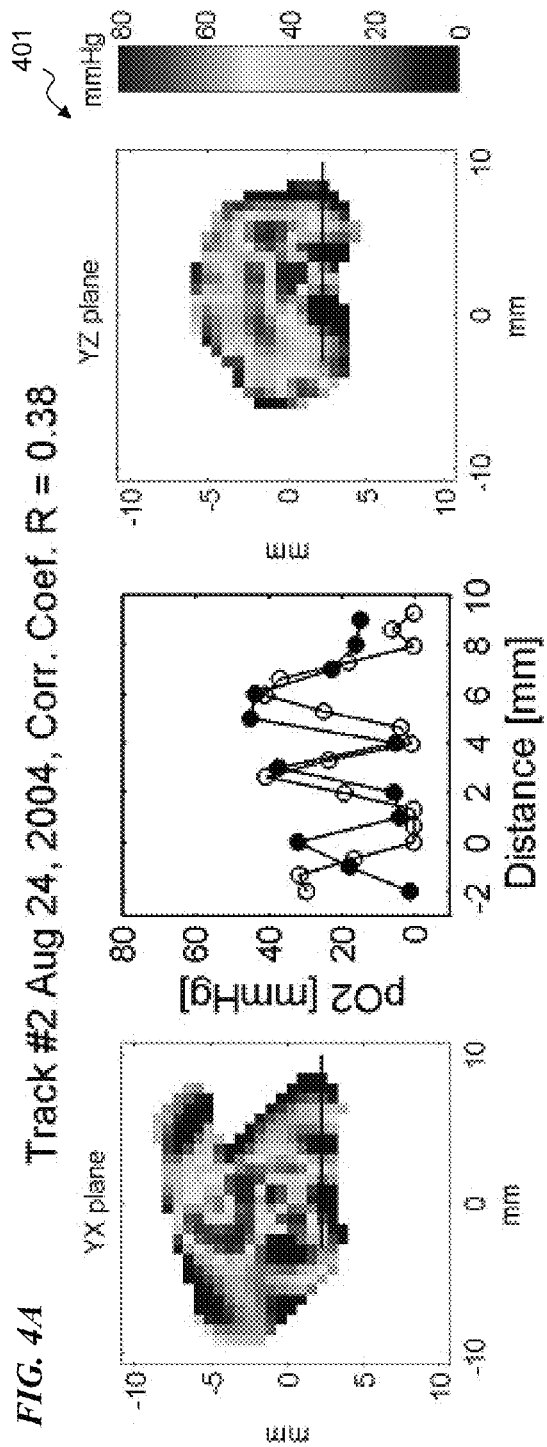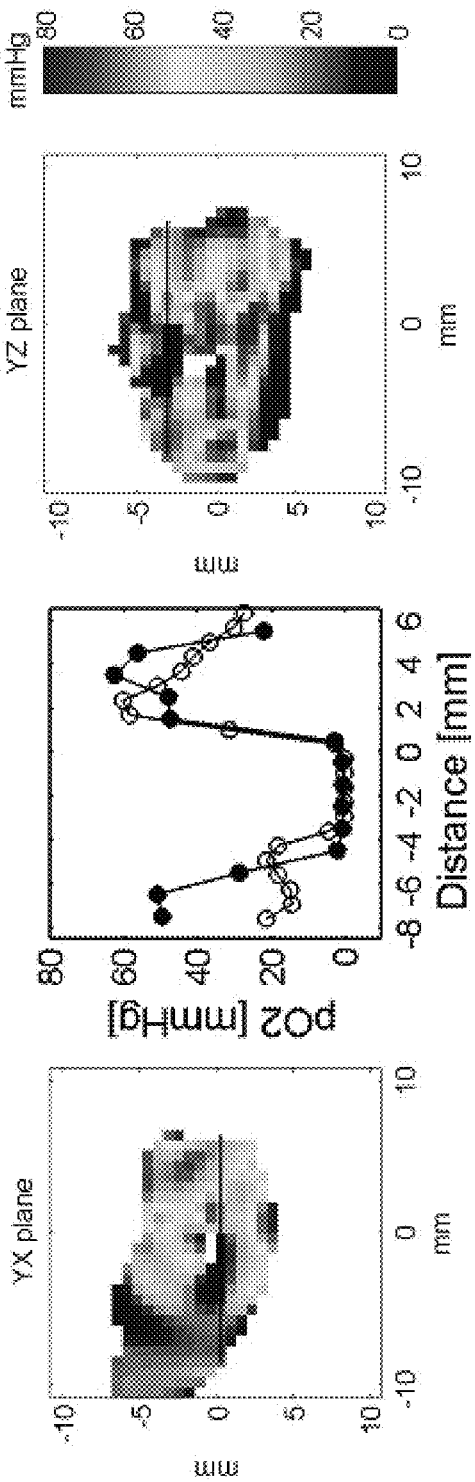
FIG. 4A

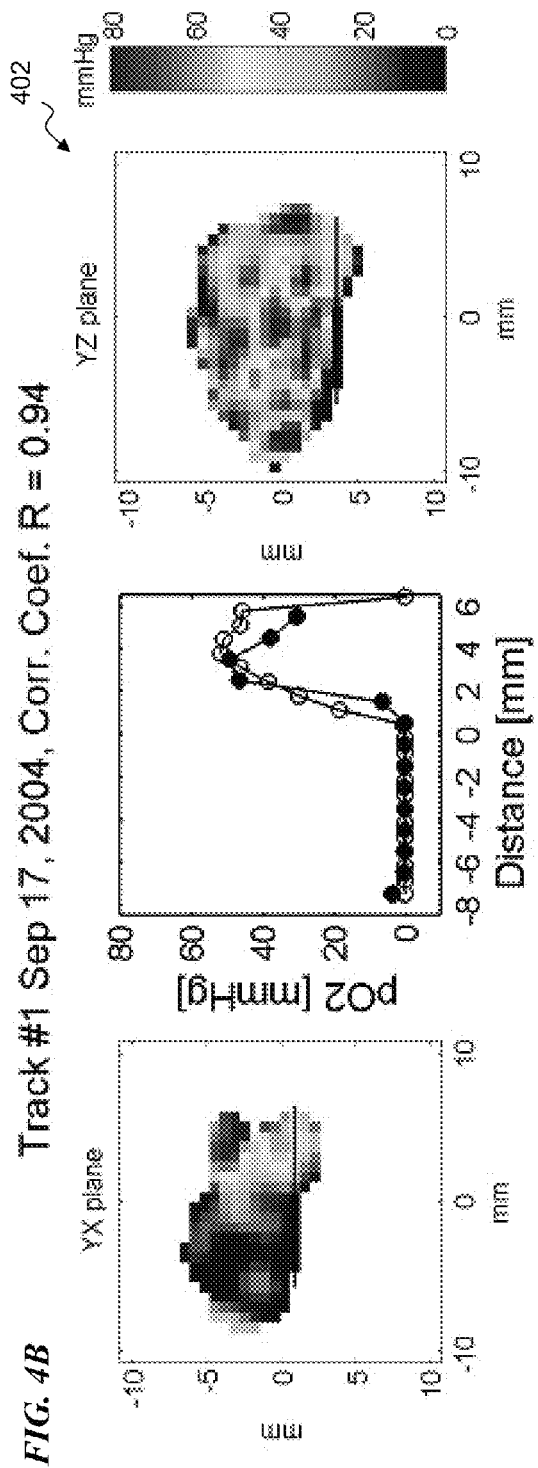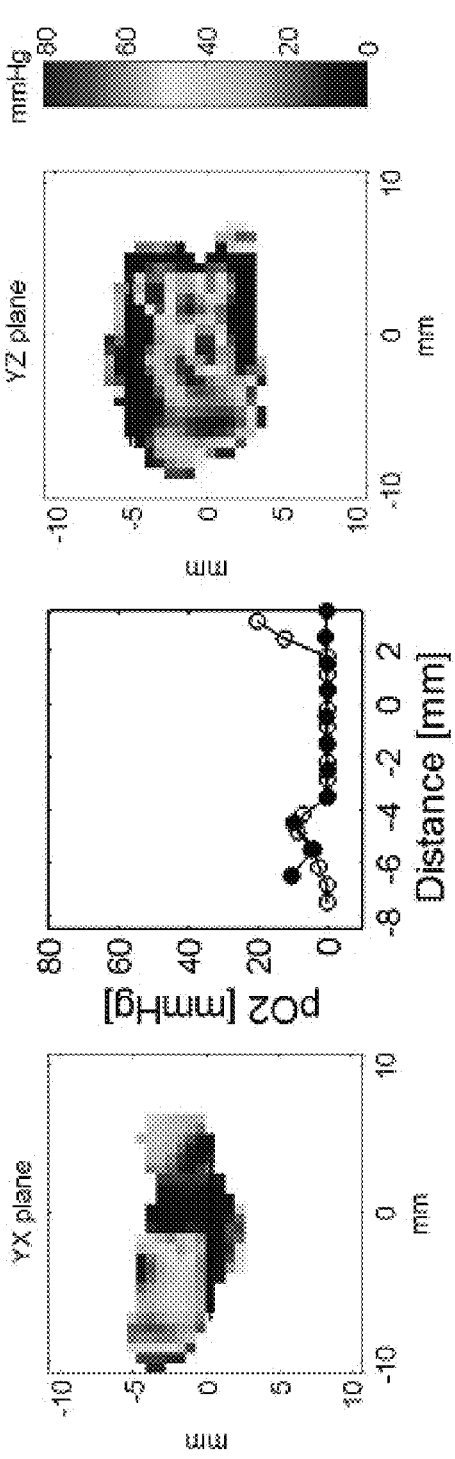
FIG. 4B

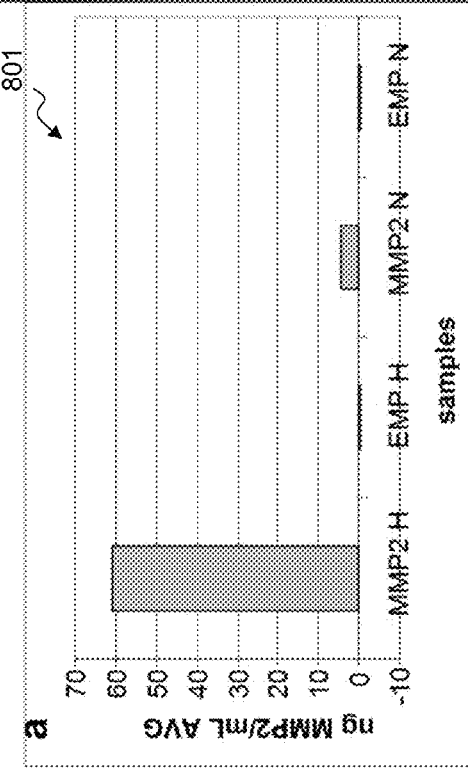
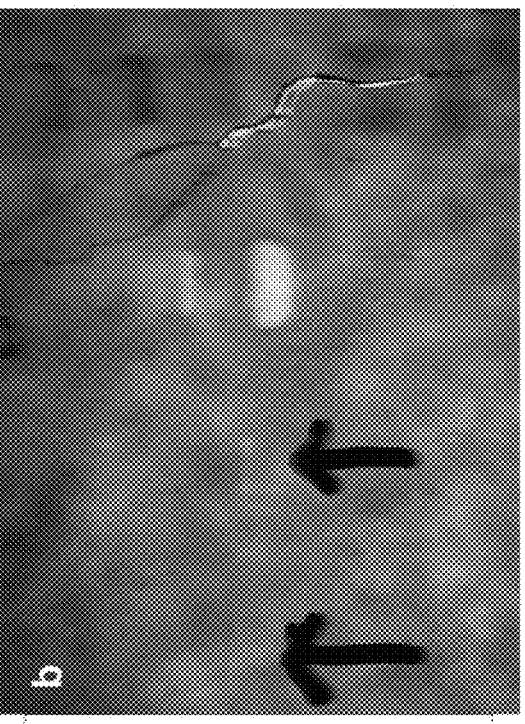
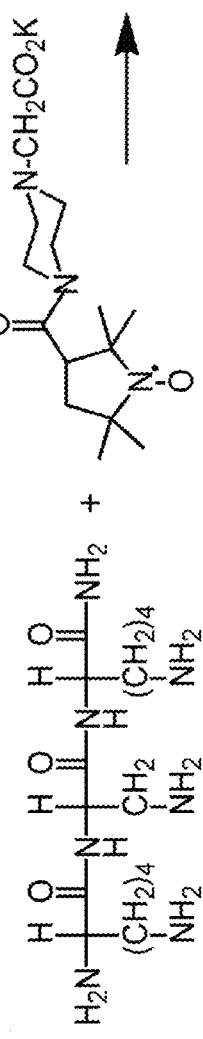
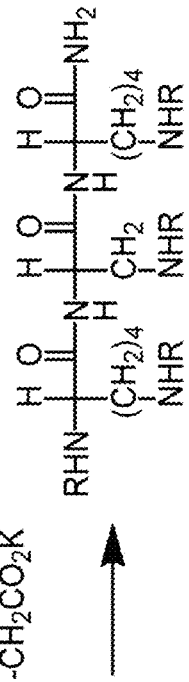
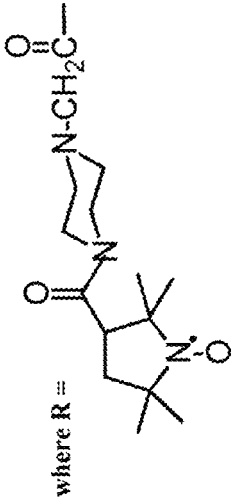
FIG. 8A
FIG. 8B
FIG. 8C

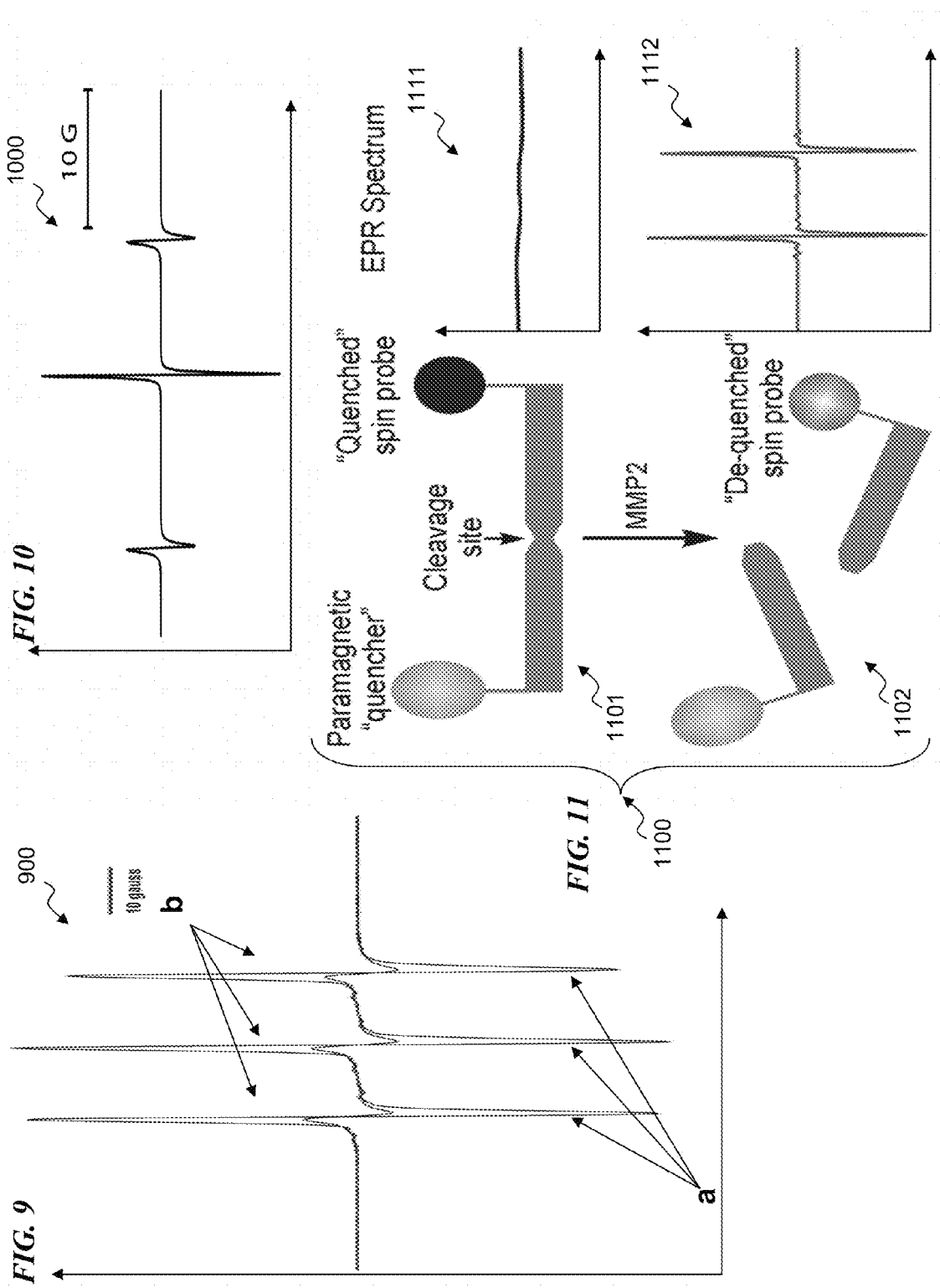

Scheme 2:
Hypoxia/↓$O_2$ ⇨ ↑MMP2

FIG. 15C  Scheme 3: Hypoxia/↓O2 ⇒ ↑MMP2 ⇒ ✗ Dinitroxide ⇔ ↑EPR Signal

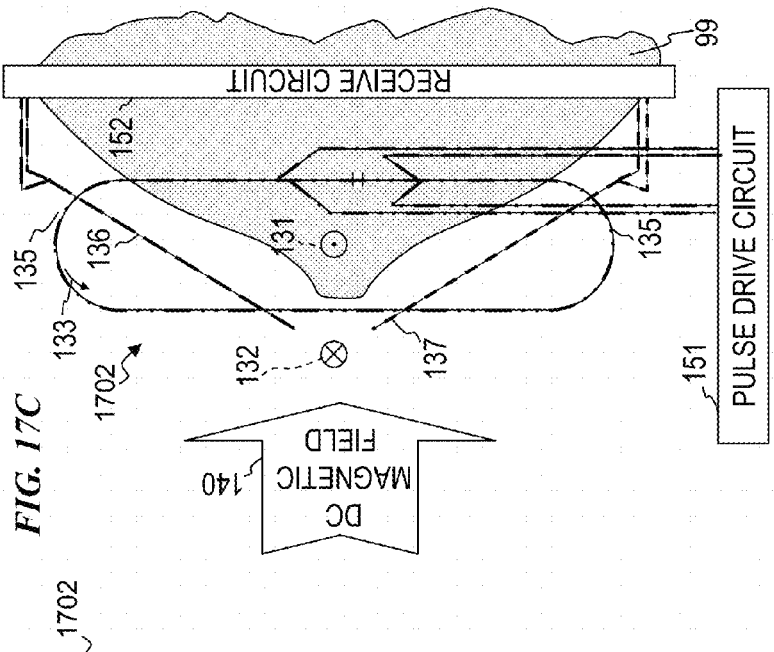
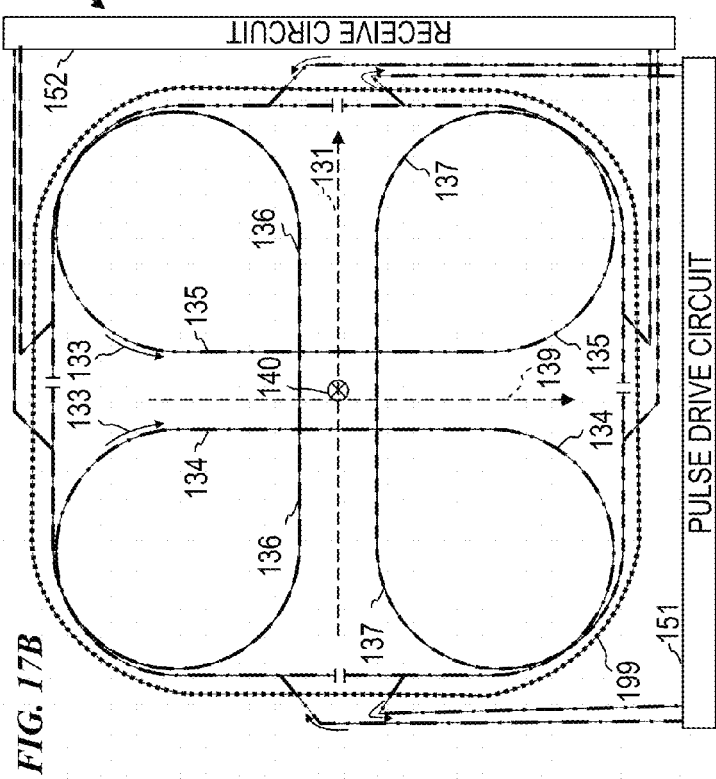
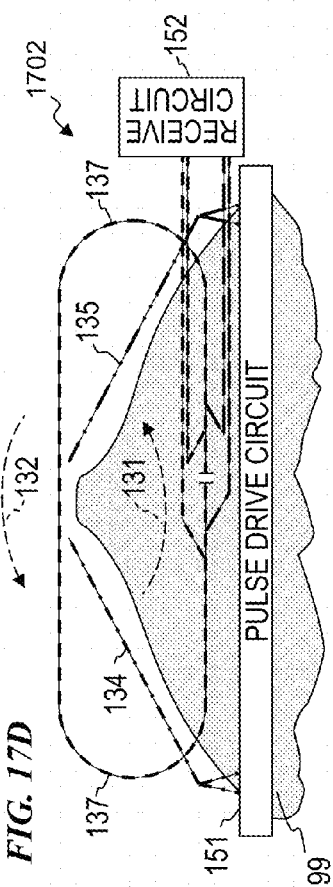
FIG. 17C
FIG. 17B
FIG. 17D

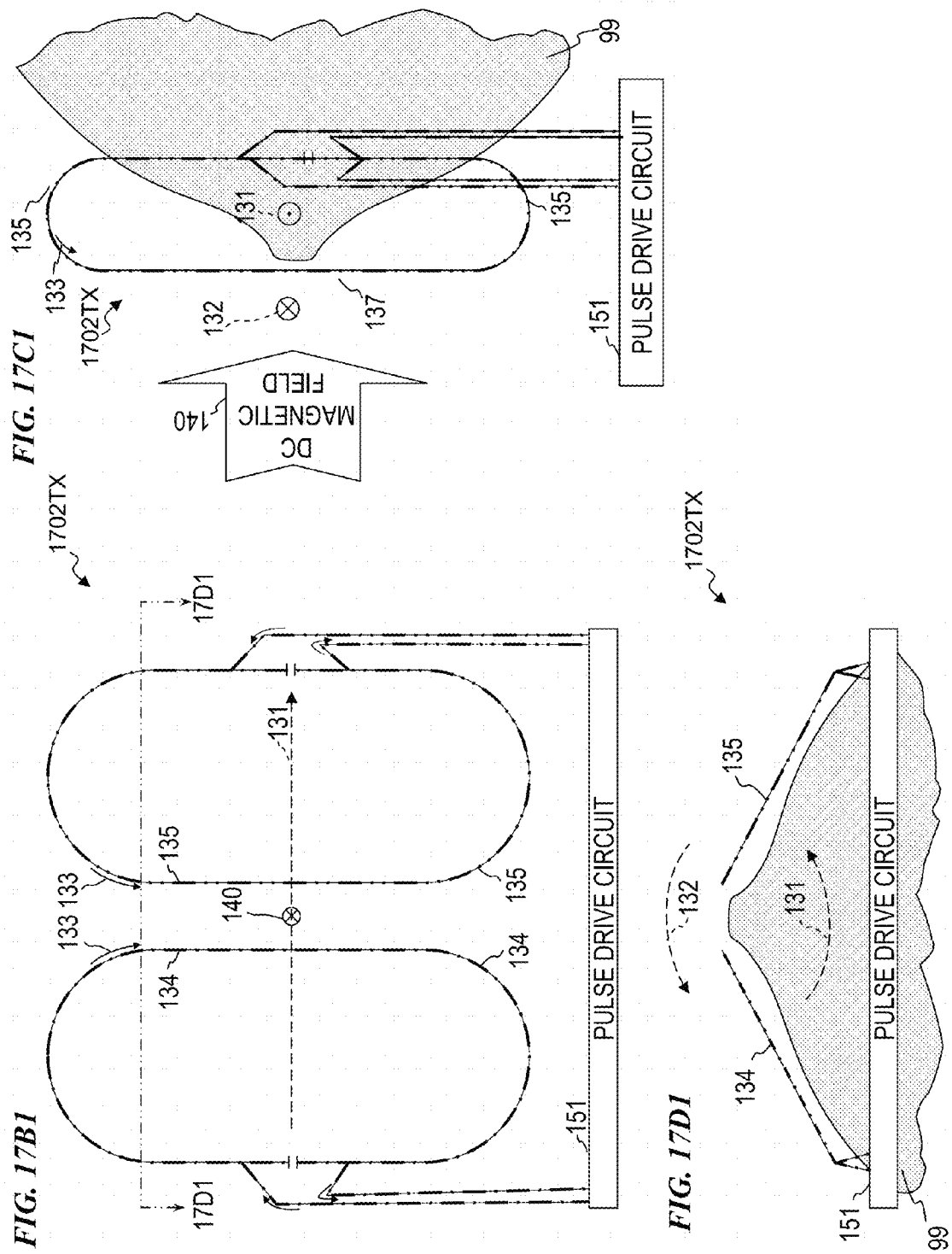

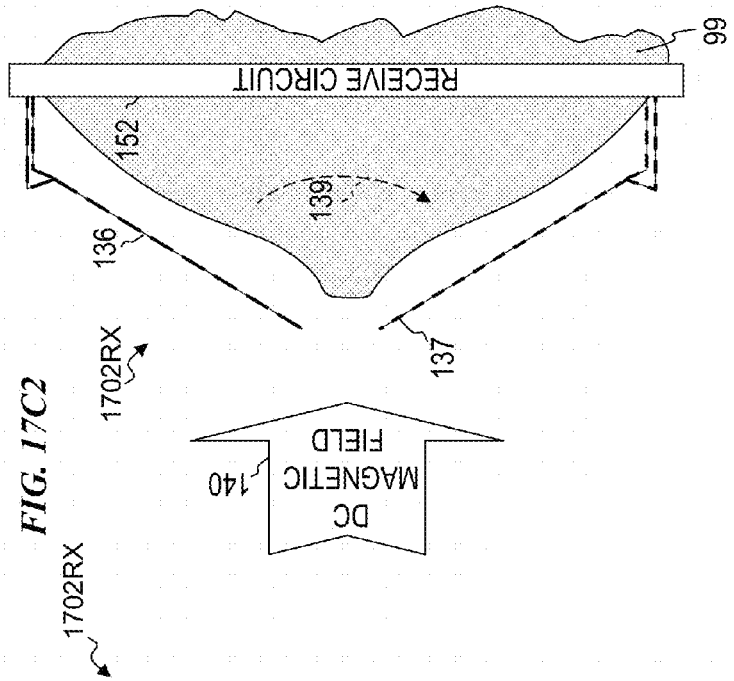
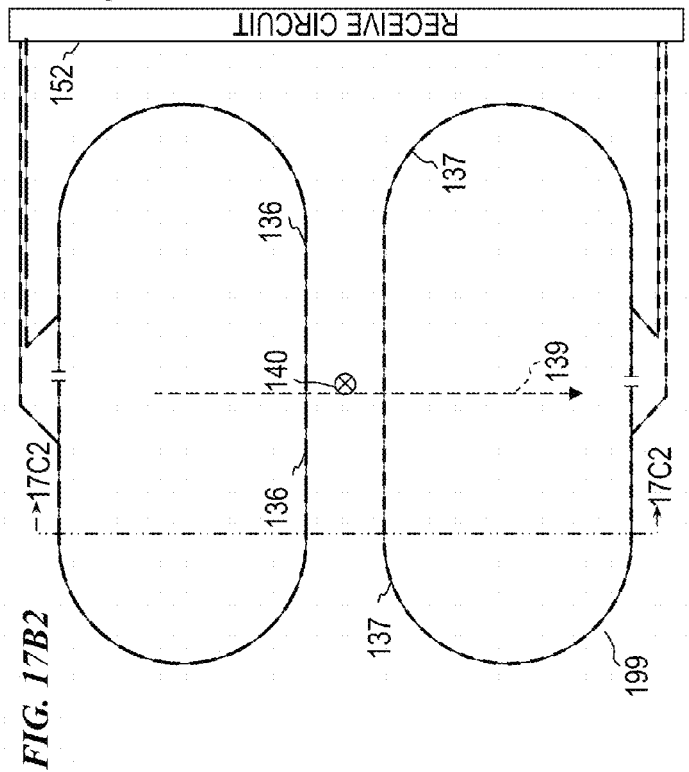
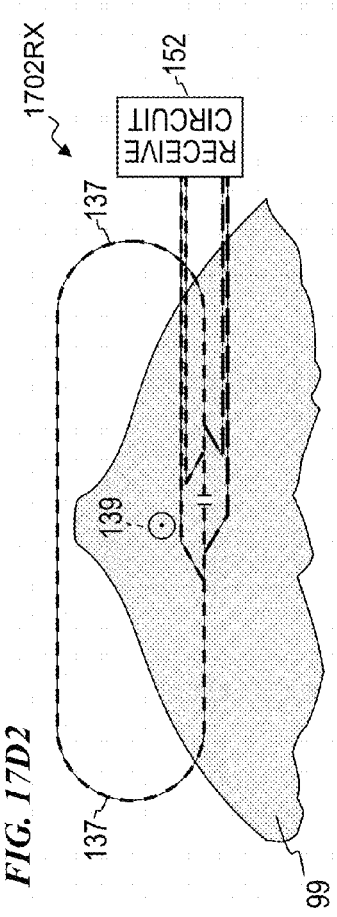
FIG. 17B2
FIG. 17C2
FIG. 17D2

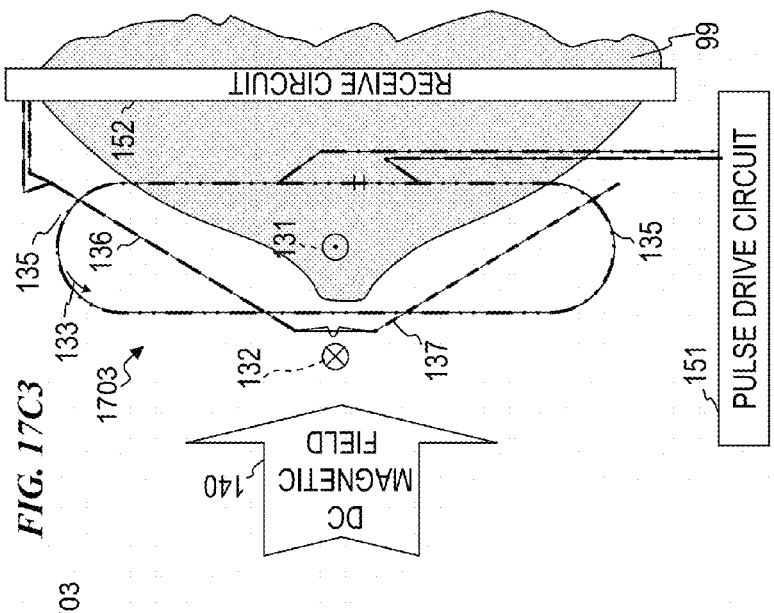
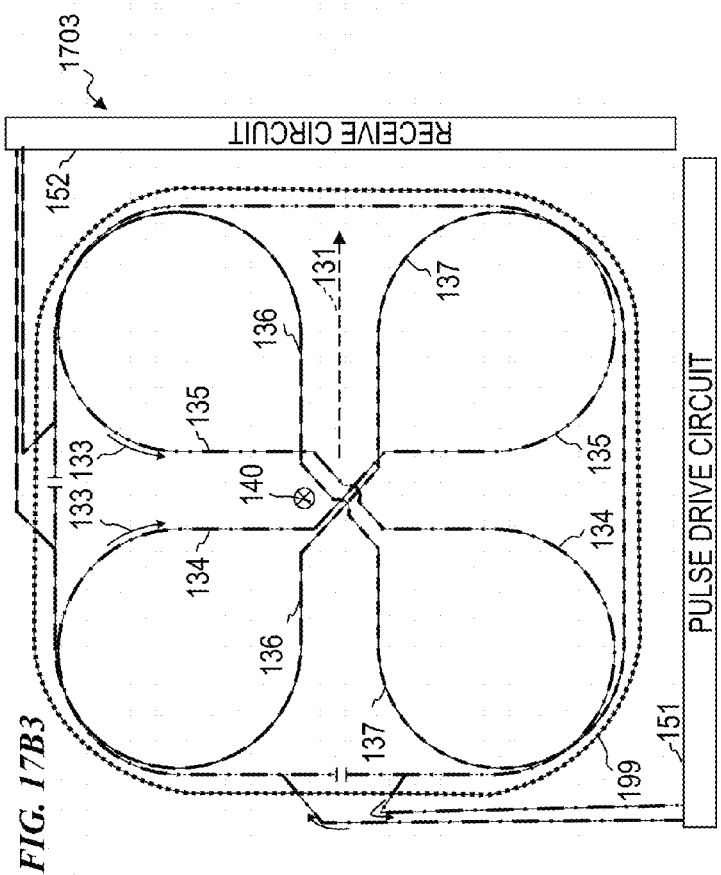
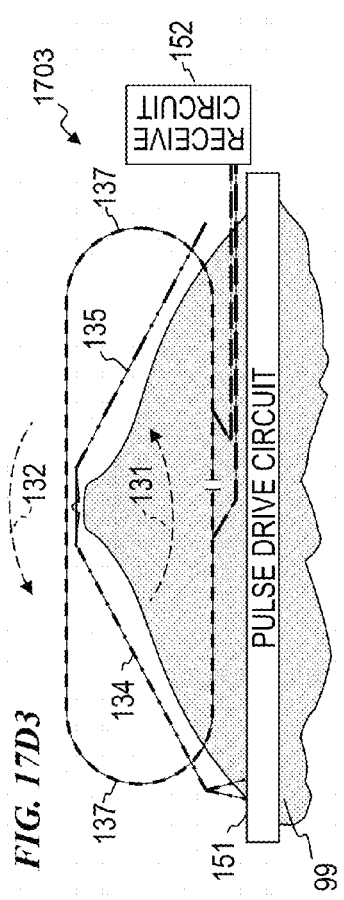

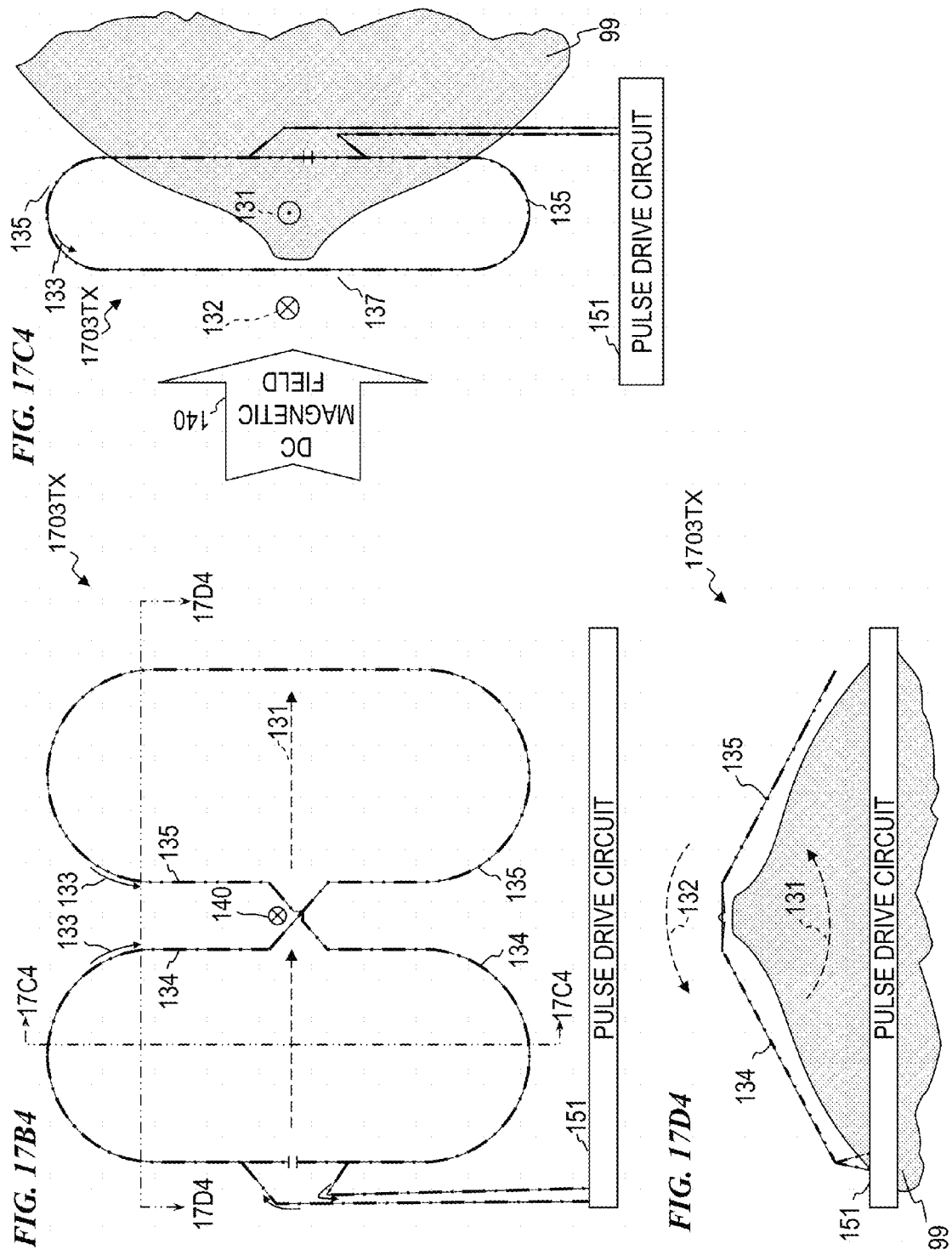

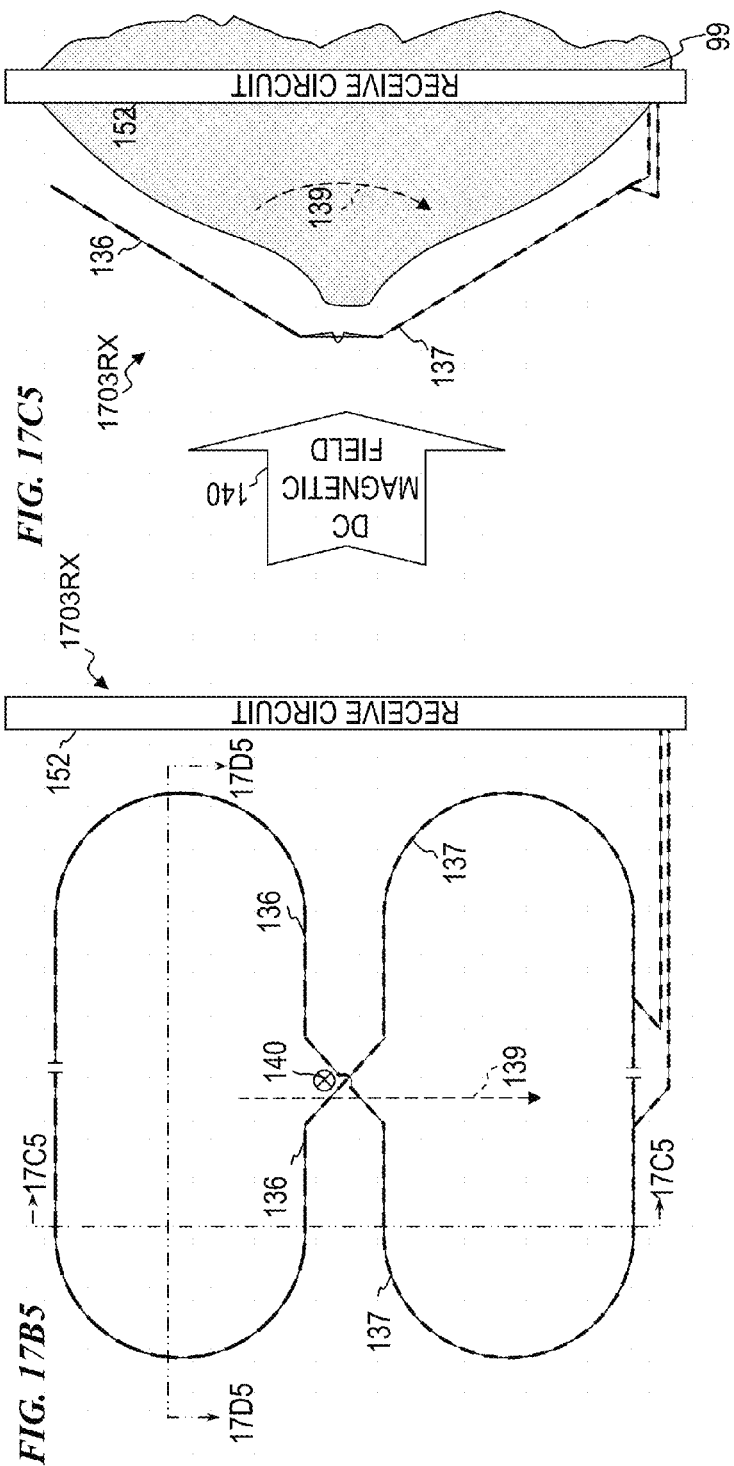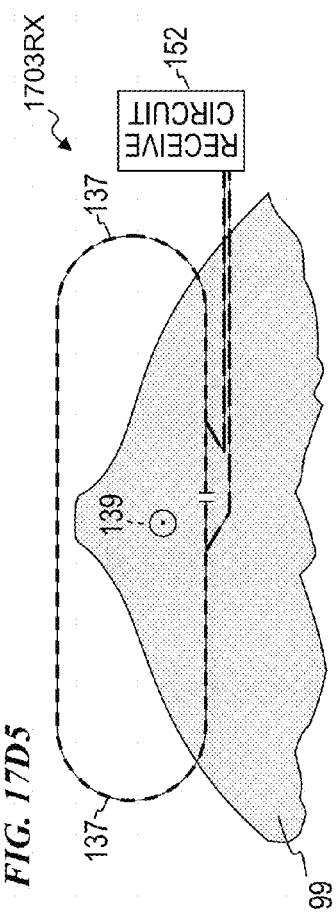

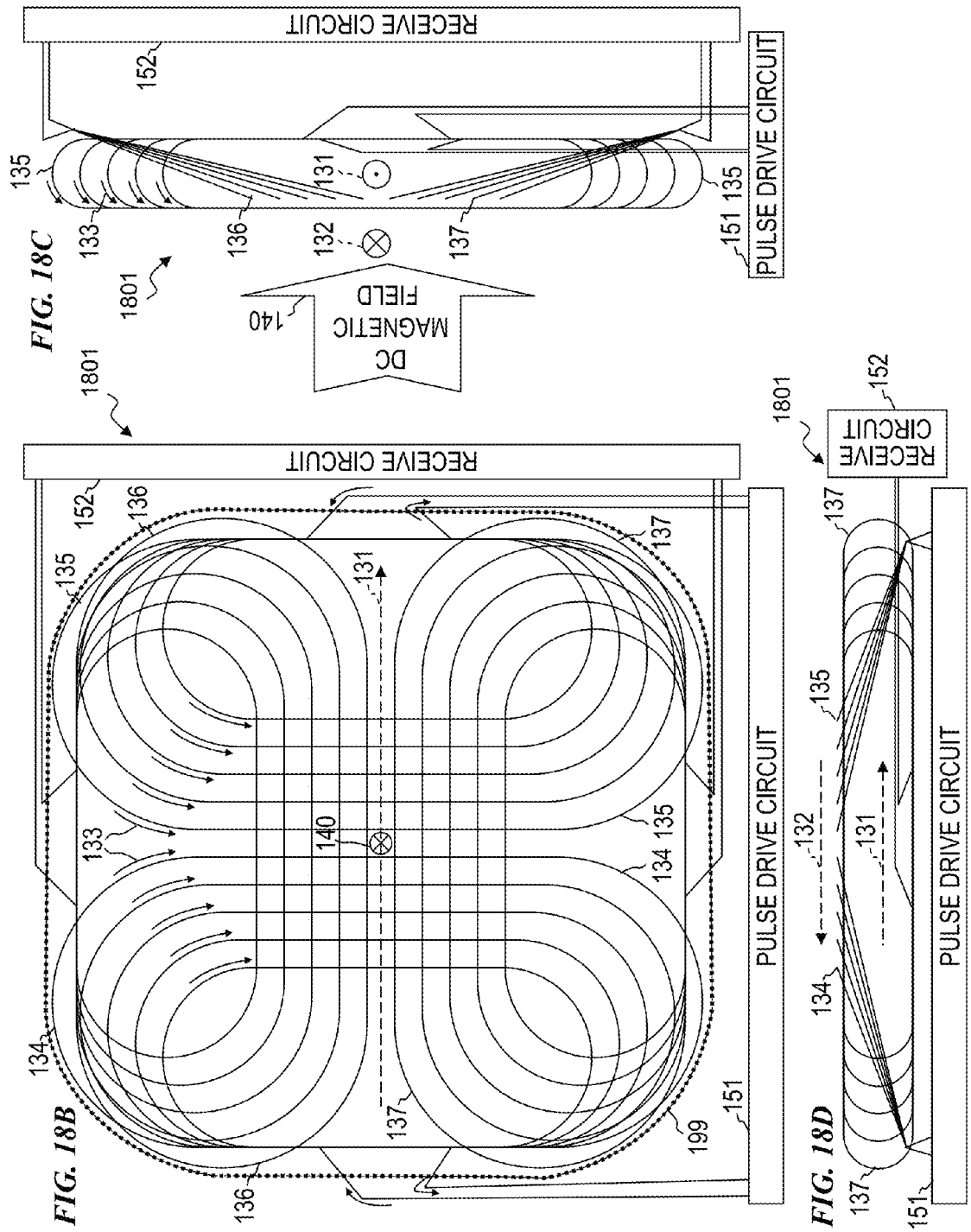

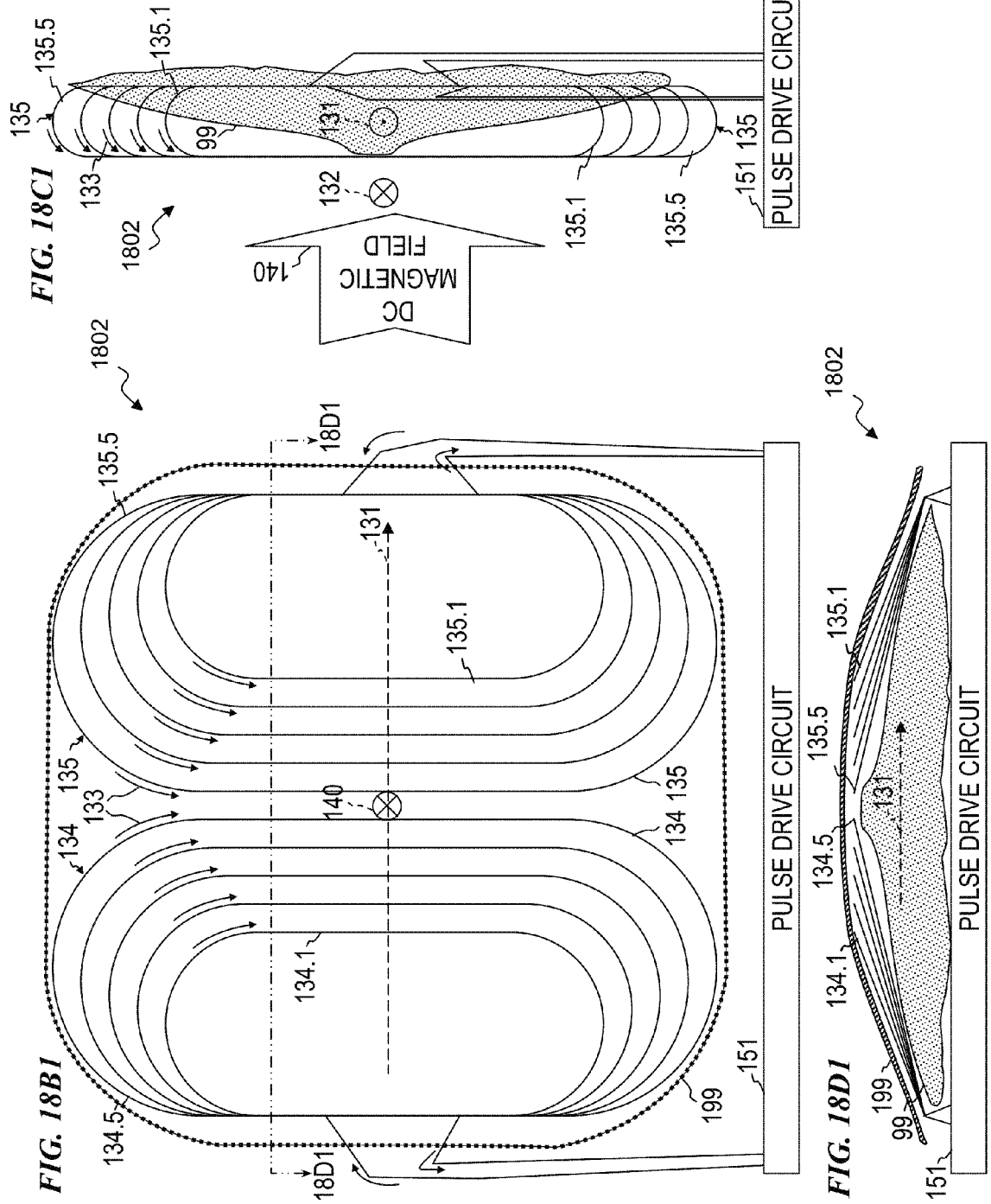

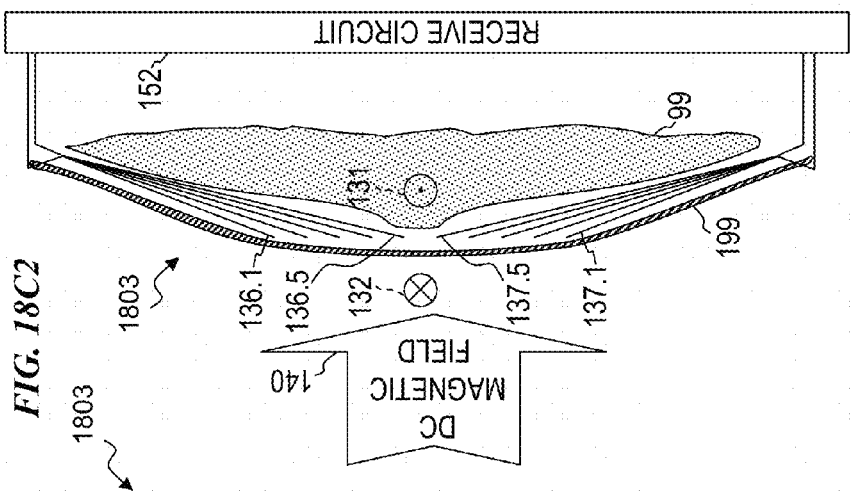
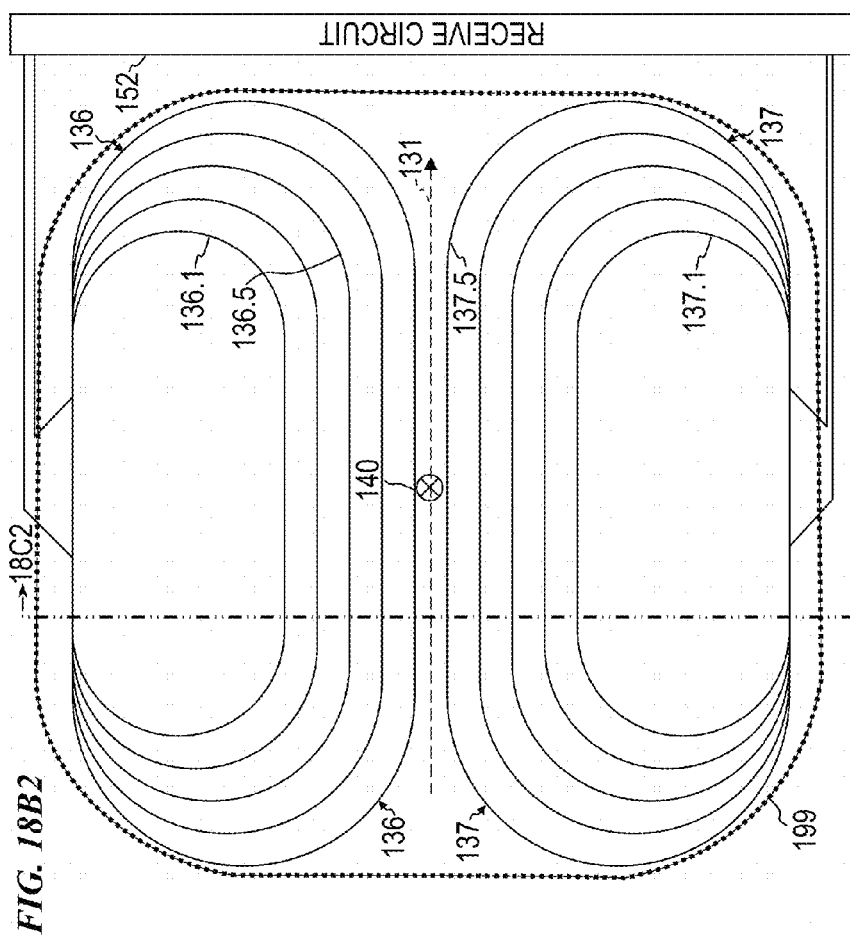
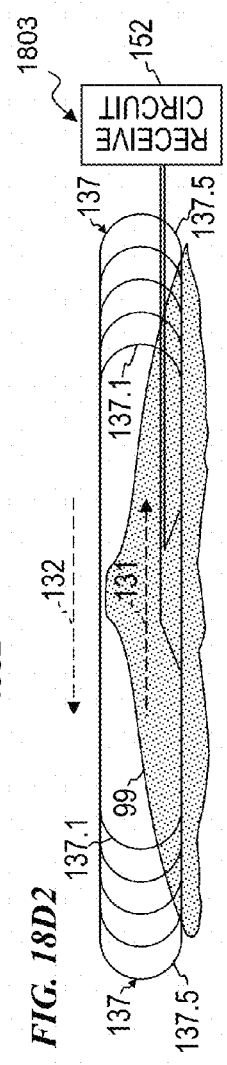

HIGH-ISOLATION TRANSMIT/RECEIVE SURFACE COILS AND METHOD FOR EPRI

CROSS-REFERENCE TO RELATED APPLICATIONS

This application claims priority to U.S. Provisional Patent Application 61/306,917 titled "HIGH-ISOLATION TRANSMIT/RECEIVE SURFACE COILS AND METHOD FOR EPRI" filed Feb. 22, 2010 by Howard J. Halpern, U.S. Provisional Patent Application 61/356,555 titled "T1-SENSITIVE INVERSION RECOVERY IMAGING APPARATUS AND METHOD FOR EPRI" filed Jun. 18, 2010 by Howard J. Halpern et al., and U.S. Provisional Patent Application 61/445,037 titled "T1-SENSITIVE INVERSION RECOVERY IMAGING METHOD AND APPARATUS FOR EPRI" filed Feb. 21, 2011 by Howard J. Halpern et al., which are all incorporated herein by reference in their entirety including their appendices.

FIELD OF THE INVENTION

This invention relates to the field of medical imaging and modeling, and more specifically to a method and apparatus having high-isolation radio-frequency (RF) transmit and receive coils useful for electron paramagnetic resonance imaging (EPRI), in situ and in vivo, using high-isolation transmit/receive surface coils, which, in some embodiments, provide microenvironmental images that are representative of particular internal structures in the human body and spatially resolved images of tissue/cell protein signals responding to conditions (such as hypoxia) that show the temporal sequence of certain biological processes, and, in some embodiments, that distinguish malignant tissue from healthy tissue.

BACKGROUND OF THE INVENTION

Attached as part of U.S. Provisional Patent Application 61/306,917 titled "HIGH-ISOLATION TRANSMIT/RECEIVE SURFACE COILS AND METHOD FOR EPRI" filed Feb. 22, 2010 by Howard J. Halpern are Appendix A (titled "A Versatile High Speed 250-MHz Pulse Imager for Biomedical Applications" by Boris Epel, et al. Concepts Magn. Reson. Part B (Magn. Reson. Engineering) 33B: 163-176, 2008), Appendix B (titled "Imaging radio frequency electron-spin-resonance spectrometer with high resolution and sensitivity for in vivo measurements" by Howard Halpern et al., Rev. Sci. Instrum. 60(6), June 1989), Appendix C, Appendix D, and Appendix E which form a part of that provisional application, which is incorporated herein by reference in its entirety including its appendices.

Cells activate protein signaling in response to crucial environmental conditions. Among the best studied is the cellular response to chronically low levels of oxygen, hypoxia. Cells respond to hypoxia by increasing hypoxia inducible factor 1α (HIF1α), a signaling peptide which is the master regulator of hypoxic response. HIF1α promotes genes and their protein products, orchestrating cell, tissue, and organism hypoxic response such as new vessel formation and increase in red cell volume.

U.S. Pat. No. 6,977,502 to David Hertz issued Dec. 20, 2005 titled "Configurable matrix receiver for MRI" is incorporated herein by reference. Hertz describes a configurable matrix receiver having a plurality of antennas that detect one or more signals. The antennas are coupled to a configurable matrix comprising a plurality of amplifiers, one or more switches that selectively couple the amplifiers in series fashion, and one or more analog-to-digital converters (ADCs) that convert the output signals generated by the amplifiers to digital form. For example, a matrix that includes a first amplifier having a first input and a first output, and a second amplifier having a second input and a second output, a switch to couple the first output of the first amplifier to a the second input of the second amplifier, a first ADC coupled to the first output of the first amplifier, and a second ADC coupled to the second output of the second amplifier. In one embodiment, the signals detected by the antennas include magnetic resonance (MR) signals.

United States Patent Application Publication 2008/0084210 by Vaughan et al. published Apr. 10, 2008 titled "Multi-Current Elements for Magnetic Resonance Radio Frequency Coils" is incorporated herein by reference. In Publication 2008/0084210, Vaughan et al. disclose a current unit having two or more current paths allows control of magnitude, phase, time, frequency and position of each of element in a radio frequency coil. For each current element, the current can be adjusted as to a phase angle, frequency and magnitude. Multiple current paths of a current unit can be used for targeting multiple spatial domains or strategic combinations of the fields generated/detected by combination of elements for targeting a single domain in magnitude, phase, time, space and frequency.

United States Patent Application Publication 2008/0129298 by Vaughan et al. published Jun. 5, 2008 titled "High field magnetic resonance" is incorporated herein by reference. In Publication 2008/0129298, Vaughan et al. disclose, among other things, multi-channel magnetic resonance using a TEM coil.

An article co-authored by the inventor of the present invention is titled "Imaging radio frequency electron-spin-resonance spectrometer with high resolution and sensitivity for in vivo measurements" by Howard Halpern et al., Rev. Sci. Instrum. 60(6), June 1989, was attached as Appendix B to U.S. Provisional Patent Application 61/306,917 titled "HIGH-ISOLATION TRANSMIT/RECEIVE SURFACE COILS AND METHOD FOR EPRI" filed Feb. 22, 2010 by Howard J. Halpern, which is also incorporated herein by reference. Halpern et al. describe a radio frequency (RF) electron-spin-resonance spectrometer with high molar sensitivity and resolution. 250-MHz RF is chosen to obtain good penetration in animal tissue and large aqueous samples.

Another article co-authored by the inventor of the present invention is titled "A Versatile High Speed 250-MHz Pulse Imager for Biomedical Applications" by Boris Epel, et al. at the Center for EPR Imaging In Vivo Physiology, Department of Radiation and Cellular Oncology, University of Chicago, Chicago, Ill. 60637 (Concepts Magn. Reson. Part B (Magn. Reson. Engineering) 33B: 163-176, 2008) was attached as Appendix A to U.S. Provisional Patent Application 61/306,917 titled "HIGH-ISOLATION TRANSMIT/RECEIVE SURFACE COILS AND METHOD FOR EPRI" filed Feb. 22, 2010 by Howard J. Halpern, which is also incorporated herein by reference. Epel et al. describe a versatile 250-MHz pulse electron paramagnetic resonance (EPR) instrument for imaging of small animals is presented. Flexible design of the imager hardware and software makes it possible to use virtually any pulse EPR imaging modality. A fast pulse-generation and data-acquisition system based on general purpose PCI boards performs measurements with minimal additional delays. Careful design of receiver protection circuitry allowed us to achieve very high sensitivity of the instrument. In this article, Epel et al. demonstrate the ability of the instrument to obtain three-dimensional (3D) images using the electron spin echo (ESE) and single-point imaging (SPI) methods. In a phantom that contains a 1 mM solution of narrow line (16 µT, peak-to-peak) paramagnetic spin probe, their device achieved an acquisition time of 32 s per image with a fast 3D ESE imaging protocol. Using an 18-min 3D phase relaxation ($T_{2e}$) ESE imaging protocol in a homogeneous sample, a spatial resolution of 1.4 mm and a standard deviation of $T_{2e}$ of 8.5% were achieved. When applied to in vivo imaging this precision of $T_{2e}$ determination would be equivalent to 2 Torr resolution of oxygen partial pressure in animal tissues.

U.S. Pat. No. 4,812,763 to Schmalbein Mar. 14, 1989 titled "Electron spin resonance spectrometer" is incorporated herein by reference. Schmalbein describes an electron spin resonance spectrometer that includes a resonator containing a sample and arranged in a magnetic field of constant strength and high homogeneity. A microwave bridge can be supplied with microwave energy in the form of an intermittent signal. Measuring signals emitted by the resonator are supplied to a detector and a signal evaluation stage. A line provided between a microwave source and the microwave bridge is subdivided into parallel pulse-shaping channels, one of them containing a phase shifter, an attenuator and a switch for the signal passing through the pulse-shaping channels. In order to be able to set, if possible, an unlimited plurality of pulse sequences for experiments of all kinds, the pulse-shaping channels are supplied in equal proportions from the line by means of a divider. All pulse-shaping channels are provided with a phase shifter and an attenuator. The pulse-shaping channels are re-united by means of a combiner arranged before the input of a common microwave power amplifier.

U.S. Pat. No. 6,639,406 to Boskamp, et al. issued Oct. 28, 2003 titled "Method and apparatus for decoupling quadrature phased array coils", and is incorporated herein by reference. Boskamp, et al. describe a method and apparatus for combining the respective readout signals for a loop and butterfly coil pair of a quadrature phased array used for magnetic resonance imaging. The technique used to combine the signals introduces a 180-degree phase shift, or multiple thereof, to the loop coil signal, thereby allowing the loop coil signal to be decoupled from other loop coil signals by a low-input-impedance preamplifier in series with the signal. This patent describes a surface coil that is applied to one surface of the body part being examined.

U.S. Pat. No. 7,659,719 to Vaughan, et al. issued Feb. 9, 2010 titled "Cavity resonator for magnetic resonance systems", and is incorporated herein by reference. Vaughan, et al. describe a magnetic resonance apparatus that includes one or more of the following features: (a) a coil having at least two sections, (b) the at least two sections having a resonant circuit, (c) the at least two sections being reactively coupled or decoupled, (d) the at least two sections being separable, (e) the coil having openings allowing a subject to see or hear and to be accessed through the coil, (f) a cushioned head restraint, and (g) a subject input/output device providing visual data to the subject, the input/output device being selected from the group consisting of mirrors, prisms, video monitors, LCD devices, and optical motion trackers. This patent describes a volume head coil that surrounds a human head.

U.S. Pat. No. 5,706,805 Swartz, et al. issued Jan. 13, 1998 titled "Apparatus and methodology for determining oxygen tension in biological systems", and is incorporated herein by reference. Swartz, et al. describe apparatus and methods for measuring oxygen tensions in biological systems utilizing physiologically acceptable paramagnetic material, such as India ink or carbon black, and electron paramagnetic resonance (EPR) oximetry. India ink is introduced to the biological system and exposed to a magnetic field and an electromagnetic field in the 1-2 GHz range. The EPR spectrum is then measured at the biological system to determine oxygen concentration. The EPR spectrum is determined by an EPR spectrometer that adjusts the resonator to a single resonator frequency to compensate for movements of the biological system, such as a human or animal. The biological system can also include other in vivo tissues, cells, and cell cultures to directly measure $pO_2$ non-destructively. The paramagnetic material can be used non-invasively or invasively depending on the goals of the $pO_2$ measurement. A detecting inductive element, as part of the EPR spectrometer resonator, is adapted relative to the measurement particularities.

U.S. Pat. No. 5,865,746 to Murugesan, et al. issued Feb. 2, 1999 titled "In vivo imaging and oxymetry by pulsed radiofrequency paramagnetic resonance", and is incorporated herein by reference. Murugesan et al. describe a system for performing pulsed RF FT EPR spectroscopy and imaging includes an ultra-fast excitation subsystem and an ultra-fast data acquisition subsystem. Additionally, method for measuring and imaging in vivo oxygen and free radicals or for performing RF FT EPR spectroscopy utilizes short RF excitations pulses and ultra-fast sampling, digitizing, and summing steps.

U.S. Pat. No. 4,280,096 to Karthe, et al. issued Jul. 21, 1981 titled "Spectrometer for measuring spatial distributions of paramagnetic centers in solid bodies", and is incorporated herein by reference. Karthe, et al. describe a spectrometer in which gradient coils are provided in order to create an inhomogeneous magnetic field for use in analyzing individual regions within the sample under examination. The gradient coils and the modulating coils are operated by discrete pulses, rather than continuously. A keying unit coordinates the interaction of the various components of the spectrometer in order to monitor resonance of the sample under examination while such pulses occur.

U.S. Pat. No. 5,828,216 to Tschudin, et al. issued Oct. 27, 1998 titled "Gated RF preamplifier for use in pulsed radiofrequency electron paramagnetic resonance and MRI", and is incorporated herein by reference. Tschudin et al. describe a gated RF preamplifier used in system for performing pulsed RF FT EPR spectroscopy and imaging or MRI. The RF preamplifier does not overload during a transmit cycle so that recovery is very fast to provide for ultra-fast data acquisition in an ultra-fast excitation subsystem. The preamplifier includes multiple low-gain amplification stages with high-speed RF gates inserted between stages that are switched off to prevent each stage from overloading during the transmit cycle.

U.S. Pat. No. 4,714,886 to one of the present inventors, Howard Halpern, issued Dec. 22, 1987 titled "Magnetic resonance analysis of substances in samples that include dissipative material", and is incorporated herein by reference. U.S. Pat. No. 4,714,886 describes magnetic resonance images of the distribution of a substance within a sample that are obtained by splaying a pair of magnetic field generating coils relative to each other to generate a magnetic field gradient along an axis of the sample. In other aspects, electron spin resonance data is derived from animal tissue, or images are derived from a sample that includes dissipative material, using a radio frequency signal of sufficiently low frequency.

There is a need for an improved apparatus and method of electron-spin-resonance spectrometry and/or imaging to non-invasively provide images representative of particular internal structures and processes in the human body, and to be able to distinguish malignant tissue from healthy tissue.

SUMMARY OF THE INVENTION

In magnetic resonance devices, radio-frequency (RF) "coils" are antenna elements arranged to transmit and/or receive RF signals to and/or from the volume of tissue being imaged, spectroscopically examined or otherwise measured.

As used herein, "surface coils" are coils that are placed on a single surface (a surface in a single plane or a slightly curved surface) of the volume of tissue being measured and the RF energy penetrates the object from that one side. Coils such as described in U.S. Pat. No. 6,639,406 to Boskamp, et al. described above are considered surface coils herein. In such a configuration, the loop coil is configured for sensing RF fields in the volume of interest that are perpendicular to the surface against which the coil pair is placed, while the butterfly coil is configured for sensing RF fields parallel to the surface against which the coil pair is placed. The main magnetic field (the direction of the static field) would typically be oriented in the volume of interest to be orthogonal to both the RF fields of the loop coil and to the RF fields of the butterfly coil. In general, surface-normal vectors for the surfaces of surface coils will be approximately parallel to the center axis of the volume of tissue that is being measured by the surface coil. See FIG. 1A.

On the other hand, "volume coils" are coils that are placed surrounding the volume of tissue being measured (e.g., when doing human imaging studies, generally around a circumference of the portion of the body being imaged, such as around the head, knee or wrist) and the RF energy penetrates completely through the object from opposite sides of the volume that are 180 degrees apart, across from one another relative to a center axis of the coil, where the center axis of the coil passes through the volume being measured. Coils such as described in U.S. Pat. No. 7,659,719 to Vaughan, et al. described above are considered volume coils herein. In general, surface-normal vectors for the inner surfaces of volume coils will be orthogonal to the center axis (or to lines parallel to the center axis) of the volume of tissue that is surrounded by the volume coil. See FIG. 1B.

In some embodiments of the present invention, "surface-volume coils" are used. As used herein, "surface-volume coils" can be thought of as between surface coils and volume coils, in that they generate and/or receive RF signals from two or more sides that are angled to one another (not co-planar and not opposite facing). In general, surface-normal vectors for the surfaces of surface-volume coils will be at acute angles to the center axis of the coil and the volume of tissue that is being measured by the surface-volume coil. See FIG. 1C.

The present invention provides a method and apparatus for medical imaging and modeling, and more specifically to a method and apparatus for electron paramagnetic resonance imaging (EPRI), in situ and in vivo. In some embodiments, the present invention uses high-isolation transmit/receive surface-volume coils, which, in some embodiments, provide microenvironmental images that are representative of particular internal structures in the human body and spatially resolved images of tissue/cell protein signals responding to conditions (such as hypoxia) that show the temporal sequence of certain biological processes (such as vascular endothelial growth factor (VEGF) signaling), and, in some embodiments, that distinguish malignant tissue from healthy tissue.

In some embodiments, the present invention provides a first set of one or more transmit coils operative to transmit an RF pulse (e.g., into a tissue of a live animal, such as a human patient), and a second set of one or more receive coils operative to receive an RF signal (e.g., a spin-echo signal from the tissue of the live animal, such as a human patient that results from electron paramagnetic resonance). In some embodiments, the transmit coils include one or more loops of conductive material (such as copper wire) that are oriented to generate an RF magnetic field generally in a first direction that is generally transverse to a static B0 magnetic field whose strength varies spatially (forming a gradient field) across a volume of tissue being imaged. That is, the direction of the B0 field would be in the Z direction, but the strength of the B0 field would change as a function of position (the direction of the gradient) in the Z direction, the X direction and/or the Y direction. In some such embodiments, the B0 gradient field would generate virtual surfaces (e.g., planes) each having one of a plurality of constant magnetic strengths, wherein the direction of the gradient (the direction of the derivative of the field strength, and thus the orientation of these planes of constant field strength, which are orthogonal to the gradient direction) would be set to a selected orientation (selected from t a plurality of different orientations) for each of a plurality of different measurements of the same volume of tissue, in order to be able to reconstruct a three-dimensional (3D) image from the received RF signals from the receive coils. The receive coils are oriented to receive a maximum amount of signals from the tissue while receiving a minimum amount of signal from the transmit coils (i.e., having the receive coils physically oriented to be RF-field isolated from the transmit coils).

In some embodiments, the present invention includes defined RF transmit pulse sequences that are configured to obtain measurements of the T1 EPR parameter of the molecules in the volume being inspected. In some embodiments, in other words, the transmitted RF excitation pulses are of a predetermined RF frequency, pulse duration, and pulse temporal spacing for a given temporally constant magnetic field (and its gradient direction) to selectively orient the spins of certain molecules (called reporter molecules) to generate spin-echo response signals (which are received and stored) that represent the T1 relaxation of the reporter molecules in a selected subset of the measurement volume of tissue. By taking a plurality of such measurements, each at a different gradient direction (and/or magnitude), the response signals are usable to reconstruct a three-dimensional (3D) image of the various components of the tissue.

In some embodiments, the present invention further includes medical procedures, animal models, and biological agents (such as viral "Trojan Horse" constructs or other vectors) that facilitate the obtaining of EPR images that distinguish different types of tissues or healthy tissues from malignant or infected tissues, and that show various spatially and temporally resolved signaling, regulation, promotion and responses of, for example, signaling peptides, protein products.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 3A is an EPR image 300 of the voxels of a single plane through a subject.

FIG. 3B is a graph 301 of an EPR spectrum of one of the voxels of FIG. 3A.

FIG. 4 is a set 400 of four panels each having two images and a graph, where the images show a comparison of Oxylite and EPROI voxel oxygen values: the four panels each showing two orthogonal planes of a single FSa tumor-bearing leg of a C3H mouse.

FIG. 4A is an enlargement 401 of the left two panels of comparison 400 of FIG. 4.

FIG. 4B is an enlargement 402 of the right two panels of comparison 400 of FIG. 4.

FIG. 8A is a graph 801 showing MMP2 ELISA of PC3 cells infected with hypoxia-inducible MMP2 vector (MMP2) or empty vector (EMP) subjected to 4 hours of hypoxia (H) or normoxia (N).

FIG. 8B is a Zymogram 802 of MMP2 showing active protein as light bands.

FIG. 8C is a sequence 803 of chemical formulae for synthesis of peptide-linked nitroxides.

FIG. 9 is a graph 900 of an EPR spectrum of Nitroxide MB: a) before MMP2, and b) after MMP2

FIG. 10 is a graph 1000 of an EPR spectrum of $^{15}$N-nitroxide plus trityl at 250 MHz (as simulated).

FIG. 11 is a schematic diagram 1100 of EPR transmitter probe (EPRTP) activated by MMP2 reporter protein.

FIG. 15C illustrates a Scheme 3 1503, wherein hypoxia (i.e., reduced oxygen) results in increased MMP2, which is used to cut dinitroxide, which then results in increased EPR signal.

FIG. 17B is a schematic plan drawing of a TX-RX isolation surface-volume coil system 1702, according to some embodiments of the present invention.

FIG. 17C is a schematic side-elevation drawing of TX-RX surface-volume isolation coil system 1702.

FIG. 17D is a schematic front-elevation drawing of TX-RX surface-volume isolation coil system 1702.

FIG. 17B1 is a schematic plan-view diagram of only the transmit portion 1702TX of TX-RX isolation coil system 1702 according to one embodiment of the present invention.

FIG. 17C1 is a schematic side-elevation-view diagram of only the transmit portion 1702TX of TX-RX isolation coil system 1702 (a view that is orthogonal to that of FIG. 17B1) according to one embodiment of the present invention.

FIG. 17D1 is a schematic front-elevation-view diagram of only the transmit portion 1702TX of TX-RX isolation coil system 1702 (a view that is orthogonal to that of FIG. 17B1 and FIG. 17C1) according to one embodiment of the present invention.

FIG. 17B2 is a schematic plan-view diagram of only the receive portion 1702RX of TX-RX isolation coil system 1702 according to one embodiment of the present invention.

FIG. 17C2 is a schematic side-elevation-view diagram of only the receive portion 1702RX of TX-RX isolation coil system 1702 (a view that is orthogonal to that of FIG. 17B2) according to one embodiment of the present invention.

FIG. 17D2 is a schematic front-elevation-view diagram of only the receive portion 1702RX of TX-RX isolation coil system 1702 (a view that is orthogonal to that of FIG. 17B2 and FIG. 17C2) according to one embodiment of the present invention.

FIG. 17B3 is a schematic plan drawing of a butterfly-type TX-RX isolation coil system 1703, according to some embodiments of the present invention.

FIG. 17C3 is a schematic side-elevation drawing of butterfly-type TX-RX isolation coil system 1703.

FIG. 17D3 is a schematic front-elevation drawing of butterfly-type TX-RX isolation coil system 1703.

FIG. 17B4 is a schematic plan-view diagram of transmit portion 1703TX of butterfly-type TX-RX isolation coil system 1703 according to one embodiment of the present invention.

FIG. 17C4 is a schematic side-elevation-view diagram of transmit portion 1703TX of butterfly-type TX-RX isolation coil system 1703 (a view that is orthogonal to that of FIG. 17B4) according to one embodiment of the present invention.

FIG. 17D4 is a schematic front-elevation-view diagram of transmit portion 1703TX of butterfly-type TX-RX isolation coil system 1703 (a view that is orthogonal to that of FIG. 17B4 and FIG. 17C4) according to one embodiment of the present invention.

FIG. 17B5 is a schematic plan-view diagram of transmit portion 1703RX of butterfly-type TX-RX isolation coil system 1703 according to one embodiment of the present invention.

FIG. 17C5 is a schematic side-elevation-view diagram of transmit portion 1703RX of butterfly-type TX-RX isolation coil system 1703 (a view that is orthogonal to that of FIG. 17B5) according to one embodiment of the present invention.

FIG. 17D5 is a schematic front-elevation-view diagram of transmit portion 1703RX of butterfly-type TX-RX isolation coil system 1703 (a view that is orthogonal to that of FIG. 17B5 and FIG. 17C5) according to one embodiment of the present invention.

FIG. 18B is a schematic plan-view diagram of transmit-receive system 1801 according to one embodiment of the present invention.

FIG. 18C is a schematic elevation-view diagram of transmit-receive system 1801 (a view that is orthogonal to that of FIG. 18B) according to one embodiment of the present invention.

FIG. 18D is a schematic elevation-view diagram of transmit-receive system 1801 (a view that is orthogonal to that of FIG. 18B and FIG. 18C) according to one embodiment of the present invention.

FIG. 18B1 is a schematic plan-view diagram of transmit portion 1802 of transmit-receive system 1801 according to one embodiment of the present invention.

FIG. 18C1 is a schematic elevation-view diagram of transmit portion 1802 of transmit-receive system 1801 (a view that is orthogonal to that of FIG. 18B1) according to one embodiment of the present invention.

FIG. 18D1 is a schematic elevation-view diagram of transmit portion 1802 of transmit-receive system 1801 (a view that is orthogonal to that of FIG. 18B1 and FIG. 18C1) according to one embodiment of the present invention.

FIG. 18B2 is a schematic plan-view diagram of receive portion 1803 of transmit-receive system 1801 according to one embodiment of the present invention.

FIG. 18C2 is a schematic elevation-view diagram of receive portion 1803 of transmit-receive system 1801 (a view that is orthogonal to that of FIG. 18B2) according to one embodiment of the present invention.

FIG. 18D2 is a schematic elevation-view diagram of receive portion 1803 of transmit-receive system 1801 (a view that is orthogonal to that of FIG. 18B2 and FIG. 18C2) according to one embodiment of the present invention.

DESCRIPTION OF PREFERRED EMBODIMENTS

Figure 1A:
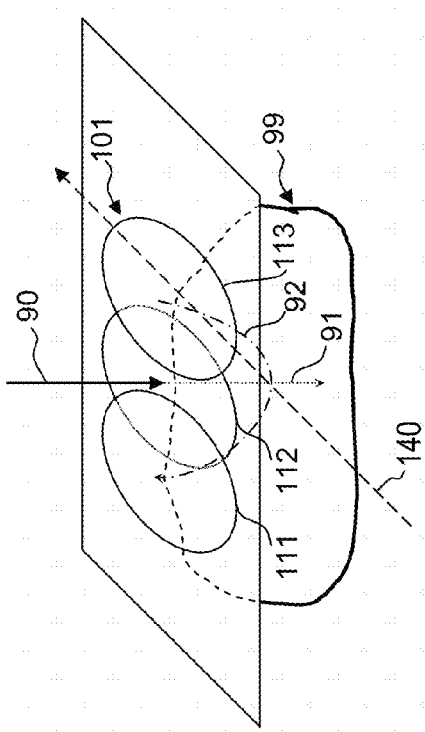
FIG. 1A is a schematic perspective drawing of a design of a transmit-receive isolation (TX-RX isolation) surface coil 101, according to some embodiments of the present invention.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon, the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Cells activate protein signaling in response to crucial environmental conditions. Among the best studied is the cellular response to chronically low levels of oxygen, hypoxia. Cells respond to hypoxia by increasing hypoxia inducible factor 1α (HIF1α), a signaling peptide which is the master regulator of hypoxic response. HIF1α promotes genes and their protein products, orchestrating cell, tissue, and organism hypoxic response such as new vessel formation and increase in red cell volume. The present invention provides a novel and potentially clinically useful technology to monitor cellular protein signaling response in vivo, using Electron Paramagnetic Resonance Imaging (EPRI). EPRI can provide highly specific magnetic resonance images of spatially resolved $pO_2$ distributions in living tissues and tumors. In some embodiments, the present invention extends the EPRI technique to spatially resolved images of tissue/cell protein signals responding to hypoxia while the system images the microenvironmental hypoxia. In some embodiments, the present invention simultaneously images, in situ, in vivo, $pO_2$ and the cellular production of HIF1α activated in response to low $pO_2$ in human PC3 xenograft tumors, in nude mice. In some embodiments, this is accomplished by locally infecting cells in the tumor with a viral "Trojan Horse" construct. The "Trojan Horse" contains hypoxia responsive elements (HRE) that bind HIF1α and promote the transcription of an exportable reporter protein (RP). The RP hydrolyses an EPR molecular beacon (EPRMB), activating an EPR signal that is imaged. The EPRMB signal is spectrally distinct from that imaging $pO_2$. In some embodiments, uninfected PC3 tumor cells produce undetectable levels of RP. The spatial 3D imaging of HIF1α response provides a unique ability to observe specific hypoxia-induced signaling in conditions as native as has been achieved heretofore. The present invention provides a way to further investigate hypoxia biology by developing vectors for imaging vascular endothelial growth factor (VEGF) signaling responding to hypoxia via a VEGF responsive element promoter/reporter adenoviral vector. It is hypothesized that malignant tissue has a different HIF1α response, in vivo, to a given $pO_2$ level in vivo than normal tissue. It is hypothesized that solid tumors have a different VEGF response to a given $pO_2$ level in vivo than normal tissue. Imaging $pO_2$, HIF1α signaling, and VEGF signaling simultaneously allows the present invention to image a detailed stimulus-response distribution. In some embodiments, this is extended to humans for cancer prognosis, to direct therapy (e.g., anti-angiogenic therapy) and to determine the response to therapy.

To create a new, gene-specific diagnostic imaging technology we propose to further develop electron paramagnetic resonance (EPR) imaging (EPRI) utilizing state of the art molecular biological approaches to exploit, in vivo, well characterized molecular pathways involved in hypoxia induced signaling. A viral vector based system containing Response Elements (RE) to hypoxia signaling proteins Hypoxia Inducible Factor 1α (HIF1α) or Vascular Endothelial Growth Factor (VEGF) signaling proteins will induce a reporter protein (RP) to activate EPR signals from separately injected EPR molecular beacons (EPRMB). The vectors will be directly injected into tumors of living mice, infecting both normal and malignant cells. The RP is matrix metallo-proteinase 2 (MMP2) which is known to be exported to the extracellular space. MMP2 is not produced by the PC3 tumors used in these experiments, and can thus serve as a reporter protein for proof of principle studies. The inventor will separately build upon our previous work and expertise to develop self quenched EPRMBs consisting of two nitroxides or a gadolinium chelate and a nitroxide linked by a peptide that is specifically hydrolysed by MMP2, activating the EPR signal. The MMP2 reporter protein will hydrolyse the peptide linker, converting a molecule with a very low EPR signal to one with a very large signal, making it detectable. Because EPR is a magnetic resonance technique, these activated signals can be imaged. This will allow in vivo registered (knowing which points in one image are at the same location in the animal as points in another) images of cell signaling in response to hypoxia defined by simultaneous EPR oxygen images (EPROI). Using EPROI we will produce registered images of tissue $pO_2$, HIF1α signaling and, VEGF. To this end, the present invention develops:

Stereotacticly located biopsy assay of HIF1α signaling registered with an EPR Oxygen Image. This will validate the localized relationship in vivo between hypoxia and the increase in HIF1α protein as the master regulator of hypoxic response. The technique is based on a proven correlation of data from EPROI based hypoxia identification with Vascular Endothelial Growth Factor (VEGF) content in stereotactically obtained biopsies registered with associated oxygen images. It is also based on the success of our demonstration that HRE vector infected cells produce, in vitro, MMP2 reporter when stimulated by hypoxia. Identifying HIF1α in biopsies registered with the EPROI represents a first step in developing an in vivo registration reporter protein and a proof of principle of the system.

A viral vector with a VEGF responsive promoter element. VEGF is an element of the hypoxia response stimulated by HIF1α. Angiogenesis stimulated by VEGF should spatially correlate with EPROI based hypoxia as does HIF1α. Development of this vector is a first step in exploring in vivo downstream signaling consequences of hypoxia imaged with EPROIs.

High-sensitivity deuterated EPR molecular beacon (EPRMB). The EPRMB is activated by MMP2 reporter protein to give rise to measurable signals using EPRI. In some embodiments, these probes consist of either two $^{15}$N-perdeuterated nitroxides or a gadolinium chelate-nitroxide pair linked by a peptide hydrolyzed by the MMP2 reporter.

Simultaneous measurement capability. Some embodiments then simultaneously image hypoxia with a trityl EPR Oxygen Image (EPROI) and hypoxia signaling with the $^{15}$N-nitroxide based HIF1α signal image which will be automatically registered. Simultaneous imaging is made possible by the 1 mT shift of the $^{15}$N of the EPRMB relative to the trityl line.

Simultaneous measurement capability extended to VEGF signaling. Using the VEGF response element vector coupled with a separate reporter system hydrolyzing a second peptide linked and quenched $^{14}$N nitroxide based EPRMB (EPRMB2), some embodiments extend the system to simultaneously image hypoxia and HIF1α and VEGF signaling. This relies on the 1-mT separation between the $^{15}$N nitroxide line and the carbon based trityl line and the 0.3 mT separation between the $^{14}$N based nitroxide central line and the carbon-based trityl at 250 MHz due to Breit-Rabi oscillations.

These EPR-based images will allow a unique combination of simultaneous imaging of the hypoxia stimulus via EPROI and the EPRMB image of the signaling response, automatic voxel-by-voxel registration and native environment. They provide not only new enabling probes of native oxygen biology, but a new technology for imaging that biology.

In some embodiments, the present invention addresses aspects of Oxygen, HIF1α, VEGF and cancer biology. Regions of low $pO_2$-hypoxia-are characteristic of solid tumors and have long been known to increase resistance of malignant cells to radiation. {Hall, 2000 #1012; Gatenby, 1988 #21; Brizel, 1996 #695; Brizel, 1999 #1121; Brizel, 1996 #1124; Brizel, 1997 #1123; Hockel, 1996 #1111} and can be exploited for cancer therapy. {Shibata, 2002 #1657} Hypoxia selects for a mutagenic, carcinogenetic, and aggressive malignant phenotype. {Graeber, 1996 #942} Oxygen status is so important in tissue homeostasis that the absence of oxygen, hypoxia is the causative element in an entire regulatory peptide signaling cascade. Hypoxia inducible factor 1α, HIF1α is the master regulator of the response of the cell response to hypoxia, initiating this cascade {Semenza, 1998 #1693} This cascade generates compensatory responses to hypoxia at the cellular level (intracrine response) e.g., apoptosis, {Carmeliet, 1998 #1132}, local vascular response (paracrine response) {Carmeliet, 1998 #1132; Semenza, 1998 #1693}, and a general organism response, e.g., erythrocyte production (endocrine response {Semenza, 1998 #1693}.

FIG. 1A is a schematic perspective drawing of a design of a transmit-receive isolation (TX-RX isolation) surface coil 101, according to some embodiments of the present invention. In some embodiments, the loop coil 112 is configured for sensing RF signals in the volume of interest that are perpendicular to the surface against which the coil pair is placed (RF fields parallel to surface normal 91 of loop coil 112), while the pair of coils 111 and 113 (or an equivalent butterfly coil) are configured for transmitting RF fields 92 that within the volume of tissue 99, are parallel to the surface against which the coil pair is placed. (Note that in other embodiments, coils 111 and 113 can be used for sensing the RF signals (in direction 92) in the volume of interest, while loop coil 112 can be used for transmitting the excitation RF fields (in direction 91).) In some embodiments, the intersection of the applied DC static magnetic field 140, the transmit field (or receive field) axis 92 and the receive field (or transmit field) axis 91 are all orthogonal to one another at a region of interest in the center of volume of tissue 99. In general, surface-normal vectors 92, 91 and 92 (respectively) for the surfaces of surface coils 111, 112, and 113 (respectively) will be approximately parallel to the center axis 90 of the volume of tissue 99 that is being measured by the surface coil 101.

Figure 1C:
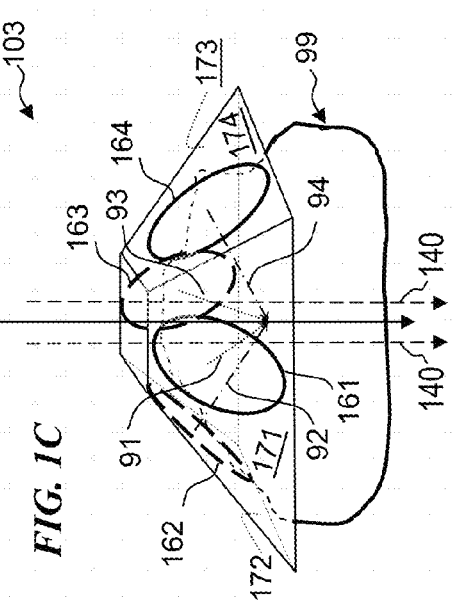
FIG. 1C is a schematic perspective drawing of a design of a transmit-receive isolation (TX-RX isolation) surface-volume coil 103, according to some embodiments of the present invention.
Figure 1B:
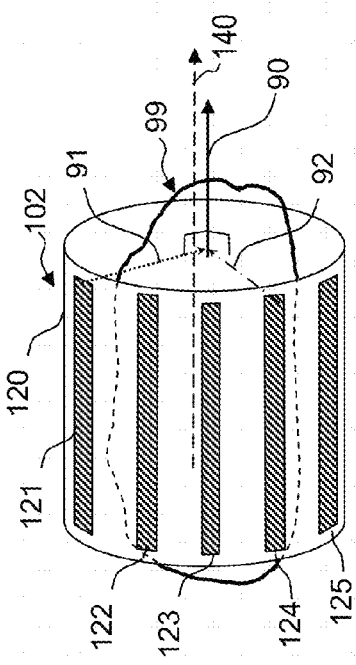
FIG. 1B is a schematic perspective drawing of a design of a transmit-receive isolation (TX-RX isolation) volume coil 102, according to some embodiments of the present invention.

FIG. 1B is a schematic perspective drawing of a design of a volume transmit-receive isolation (TX-RX isolation) volume coil 102, according to some embodiments of the present invention. In some embodiments, volume coil 102 is placed surrounding the volume of tissue 99 being measured (e.g., when doing human imaging studies, generally around a circumference of the portion of the body being imaged, such as around the head, knee or wrist) and the RF energy penetrates completely through the object from opposite sides of the volume that are 180 degrees apart, across from one another relative to a center axis of the coil, where the center axis 90 of the coil 102 passes through the volume 99 being measured. In some embodiments, two or more coil elements (e.g., element 121 and its corresponding element (not shown) on the opposite side of the cylinder 120) would be used for the transmit signal which would penetrate the tissue 99 in direction 91, while two or more coil elements (e.g., element 124 and its corresponding element (not shown) on the opposite side of the cylinder 120) that are at right angles to the transmit coil elements are used for the receive signal. In general, surface-normal vectors (e.g., vectors in directions 91 and 92) for the inner surfaces of volume coils will be orthogonal to the center axis 90 of the coil 102 (or to lines parallel to the center axis), which is also the center axis of the volume of tissue 99 that is surrounded by the volume coil 102. The intersection of the applied DC static magnetic field 140, the transmit field (or receive field) axis 92 and the receive field (or transmit field) axis 91 are all orthogonal to one another at a region of interest in the center of volume of tissue 99. In various embodiments, the antenna elements 121, 122, 123, 124, 125 and the like can be implemented as any suitable antenna form (such as wire loops, dipoles, etc.).

FIG. 1C is a schematic perspective drawing of a design of a transmit-receive isolation (TX-RX isolation) surface-volume coil 103, according to some embodiments of the present invention. As used herein, "surface-volume coils" can be thought of as a configuration between that of surface coils and that of volume coils, in that they generate and/or receive RF signals from two or more sides that are angled to one another (not co-planar such as shown in FIG. 1A and not opposite facing such as shown in FIG. 1B). In some embodiments, two of the coil elements 162 (having surface normal vector 92) and 164 (having surface normal vector 94), on opposite sides of center axis 90 of the coil 103 and having their respective surface normal vectors 92 and 94 intersect center axis 90 at acute angles, are used to transmit the RF pulses used for the magnetic resonance excitation, while the other two coil elements 161 (having surface normal vector 91) and 163 (having surface normal vector 93), on opposite sides of center axis 90 orthogonal to the transmit vectors of the coil 103 and having their respective surface normal vectors 91 and 93 intersect center axis 90 at acute angles, are used to receive the resulting RF signals. Note that in some embodiments, the plane defined by (i.e., the plane containing both) surface normal vector 91 and surface normal vector 93 is orthogonal to the plane defined by (i.e., the plane containing both) surface normal vector 92 and surface normal vector 94, and the center axis 90 and the static field 140 are substantially parallel to the intersection of these two planes. In general, surface-normal vectors for the surfaces of surface-volume coils will be at acute angles to the center axis of the coil and the volume of tissue that is being measured by the surface-volume coil.

In some embodiments, the set of RF transmit coils includes a first transmit loop 162 and a second transmit loop 164, wherein the first transmit loop 162 is positioned on a first surface 172 having a first surface normal vector 92 at a generally center location (e.g., at a centroid of the loop) on the first surface 172 within a periphery of the first transmit loop 162, wherein the second transmit loop 164 is positioned on a second surface 174 having a second surface normal vector 94 at a center location on the second surface 174 within a periphery of the second transmit loop 164, and wherein the first surface normal vector 92 and the second surface normal vector 94 define a first plane (up-down and left-right in FIG. 1C). The set of RF receive coils includes a first receive loop 161 and a second receive loop 163, wherein the first receive loop 161 is positioned on a third surface 171 having a third surface normal vector 91 at a center location on the third surface 171 within a periphery of the first receive loop 161, wherein the second receive loop 163 is positioned on a fourth surface 173 having a fourth surface normal vector 93 at a center location within a periphery of the second receive loop 163, and wherein the third surface normal vector 91 and the fourth surface normal vector 93 define a second plane. The first plane is orthogonal to the second plane, and a line or vector 90 defined by the intersection of the first plane and the second plane (which is considered herein as generally the center vector 90 of the surface-volume coil 103) forms an acute angle (the angle between vector 90 and 92) to the first normal vector, forms an acute angle (the angle between vector 90 and 94) to the second normal vector, forms an acute angle (the angle between vector 90 and 91) to the third normal vector, and forms an acute angle (the angle between vector 90 and 93) to the fourth normal vector.

In some embodiments, the surface 172 is a first plane and the surface 174 is a second plane, and a third plane that contains surface normal vector 92 and surface normal vector 92 (as well as the center vector 90) is orthogonal to the first plane and to the second plane. In some embodiments, the angle between surface normal vector 92 and center vector 90 has approximately the same value as the angle between surface normal vector 94 and center vector 90. In some embodiments, the surface 171 is a fourth plane and the surface 173 is a fifth plane, and a sixth plane that contains surface normal vector 91 and surface normal vector 93 (as well as the center vector 90) is orthogonal to the fourth plane and to the fifth plane. Note that the center vector is the intersection between the third plane and the sixth plane. In some embodiments, the angle between surface normal vector 91 and center vector 90 has approximately the same value as the angle between surface normal vector 93 and center vector 90. In some embodiments, for surface coils of the present invention, the value of these angles is in a range of between about 0 degrees and about 10 degrees inclusive. In some embodiments, for surface-volume coils of the present invention, the value of these angles is in a range of between about 10 degrees and about 90 degrees inclusive. In some embodiments, for surface-volume coils of the present invention, the value of these angles is in a range of between about 10 degrees and about 20 degrees inclusive. In some embodiments, the value of these angles is in a range of between about 20 degrees and about 30 degrees inclusive. In some embodiments, the value of these angles is in a range of between about 30 degrees and about 40 degrees inclusive. In some embodiments, the value of these angles is in a range of between about 40 degrees and about 50 degrees inclusive. In some embodiments, the value of these angles is about 45 degrees. In some embodiments, the value of these angles is in a range of between about 50 degrees and about 60 degrees inclusive. In some embodiments, the value of these angles is in a range of between about 60 degrees and about 70 degrees inclusive. In some embodiments, the value of these angles is in a range of between about 70 degrees and about 80 degrees inclusive. In some embodiments, the value of these angles is in a range of between about 80 degrees and about 90 degrees inclusive.

In other embodiments, each of the four loops 161, 162, 163 and 164 is replaced by a plurality of loops (e.g., see FIGS. 18A-18G), and each one of these pluralities of loops is mounted on a surface having a surface normal vector, and each of these surface normal vectors forms an angle with the center line or vector 90 having a value that is between 0 degrees and about 10 degrees for surface coils of the present invention, and having a value between about 10 degrees and 90 degrees (or one or more of the subranges listed above in the previous paragraph) for surface-volume coils of the present invention.

It is hypothesized that in vivo, in situ, the signal peptide response to hypoxic environment is different in native and malignant cells.

The present invention develops unique electron paramagnetic resonance (EPR) imaging (EPRI) technology to demonstrate this in animals with possible extension to humans. Although in vitro work has established HIF1α signaling, in vivo, native environment signaling appears to be far more complicated. Given the heterogeneity of tissue $pO_2$ (FIG. 1) this must be done using $pO_2$ images and co-localized or registered signal images. The need for imaging is particularly acute in tumors because of the rapid variation of tumor $pO_2$ with location—large spatial oxygen gradients—in vivo as found in electron paramagnetic resonance (EPR) oxygen images (EPROI) (FIG. 1). {Elas, 2006 #1906; Elas, 2008 #2117} A major goal of the Center for EPR Imaging In Vivo Physiology is higher $pO_2$ and spatial resolution images of tissue and tumor $pO_2$. The present invention develops an entirely new means of molecular imaging of the peptide signal response to hypoxia, using EPR, registered with $pO_2$ images. This technique can be extended to a vast array of peptide signaling processes. An example of this is the imaging of Vascular Endothelial Growth Factor, VEGF, an HIF1 signal response to create new vessels. Combined, co-localized images of $pO_2$ and peptide signaling response will produce a quantified, localized relationship between the extent of hypoxia and the cell/tissue signal response to hypoxia which we hypothesize is different in malignant and normal tissue. Through the Center, the eventual extension of EPR imaging technology to humans is anticipated. Thus, the cell signaling technology described here may impact the study of human health and disease.

The impact of EPR oxygen imaging on the study of human health and disease.

Figure 1D:
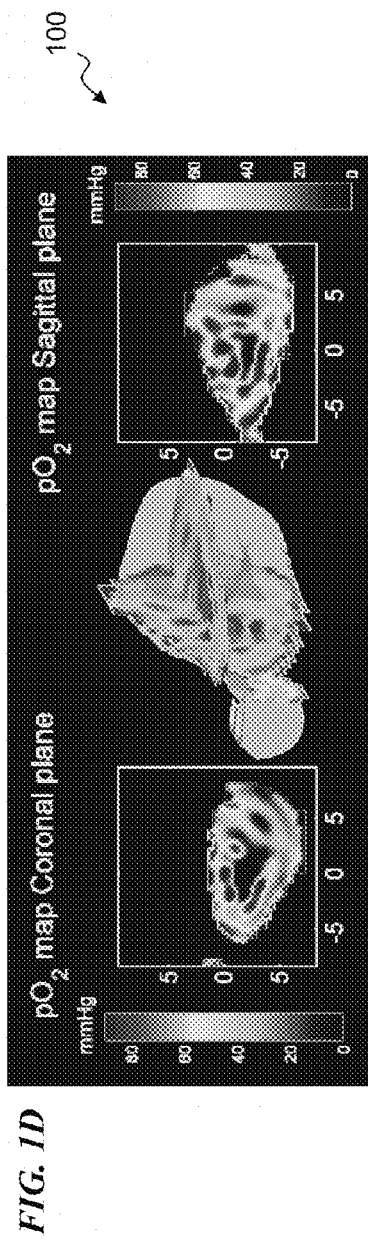
FIG. 1D is an electron paramagnetic resonance (EPR) image 100 of oxygen concentrations (EPR oxygen image) of mouse leg bearing an FSa fibrosarcoma. Colorbars show $pO_2$ in mm/hg (torr). Numbers on the images are length scales in millimeters (mm). 1-mm spatial and 3-torr $pO_2$ resolutions are shown. Note that the tumor is not distinguished in this image. The tumor is defined using a registered $T_2$ nuclear-magnetic-resonance image (MRI).

FIG. 1D is a two-plane set 100 of EPR oxygen images of a mouse leg bearing an FSa fibrosarcoma. The color bars at the far left and far right show $pO_2$ in mm/hg (torr). Numbers on figures are distances in mm. 1 mm spatial and 3 torr $pO_2$ resolution are shown. The center-left image is a $pO_2$ map in a coronal plane, the center-right image is a $pO_2$ map in a sagittal plane, and the centermost image is a perspective view showing both planes intersecting one another. Note that the tumor is not distinguished in this image. In some embodiments, the tumor would be defined using registered $T_2$ MRIs (nuclear magnetic resonance images) and shown superimposed on these EPR oxygen-map images.

Why should one image cell signaling with molecular imaging?

Recent cell-signaling discoveries have provided unique insight into modes by which cells communicate with cells in their environment, the basis of multicellular organism homeostasis. {Alberts, 2008 #2096} Studying isolated cells or cell colonies is biology in artificial environments which contrast with those of a living animal. {Fischbach, 2009 #2089} The interaction of anatomy and signaling molecules through vascular bed structure, target organ distance, size and location can affect signaling. Organ or tissue dependent modulation of the signaling can provide another layer of control to understand the physiology of signaling. But the most important reason to image cell signaling is the variation with position, shown in FIG. 1, of cellular environments. Registering images of a quantified environment characteristic like $pO_2$ with images of the peptide response allows the development of models stimulus and response in a native environment.

Reporter Gene/Molecular Beacon Imaging Technologies:

The reporter gene LacZ has been a major tool used to dissect transcription induction using optical and fluorescence transmitter probe detection. {Alam, 1990 #1662} The original such technology, LacZ, the bacterial gene encoding β-galactosidase (reporter) turns the indole linked sugar X-Gal (molecular beacon) blue. {Holt, 1958 #1663} By coupling the β-galactosidase gene to a gene of interest, gene expression is directly seen taking place in blue cells. Many other such technologies have followed. {Alam, 1990 #1662; Chalfie, 1994 #1664; Weissleder, 2003 #1694; McCaffrey, 2003 #1692; Blasberg, 2003 #1681; Massoud, 2003 #1687; Herschman, 2003 #1684}, producing chromophores or fluorescence in cells producing transcriptionally coupled gene products that can be detected and imaged in vivo. The work described here uses this basic technique, modified to turn on an EPR molecular beacon so that it can be imaged in vivo obviating the problems with radionuclide, optical or MRI techniques.

Comparison of Molecular Imaging Techniques: Optical images and radionuclide imaging dominate molecular imaging. {Dothager, 2009 #2227} Optical techniques use reporter genes that can be engineered into transgenic mice {Zhang, 2001 #1695} or into implanted tumor cells in mice and detected not only as a primary growth but as micro-metastases. {Adams, 2002 #1680} Optical techniques are surface weighted because of the rapid non-resonant absorption of optical frequency light by tissue. This makes it difficult to quantify image signal intensity, linewidths or relaxation times of depth greater than a few mm. {Kirkpatrick, 2004 #1691} Other than in artificial systems such as window chamber {Dewhirst, 1996 #1775}, quantified relationship between stimulus such as micro-environmental oxygen and peptide signal response is difficult.

Detection of radiotracer with positron emission tomography (PET) avoids problems with depth sensitivity {Schober, 2009 #2099; Sun, 2001 #1374; Blasberg, 2003 #1665} and is extremely flexible. The advantage of reporters retain radiotracer is that it can be translated to human studies. However, a major problem with PET imaging is its limited resolution in space (~2 mm) and time. Single photon emission computed tomography (SPECT) with pinhole optics {Beekman, 2007 #2100} has progressed in resolution, although this depends on the magnitude of the radiotracer signal. In principle, the work described here could be accomplished with radionuclide techniques. For radionuclide studies hypoxia is defined as the reductive retention of nitro-imidazole {Raleigh, 1992 #765; Evans, 1996 #931} or ATSM copper chelates. {Lewis, 1999 #1371} Hypoxic signaling via HIF1α might be imaged, as is described herein, with adenoviral vectors containing hypoxia responsive elements that bind HIF1α which then promotes production of a downstream signal by inducing the synthesis of thymidine kinase that would cause hypoxic cells to retain radioactive thymidine. The limitations of this are:

1) It would be difficult to distinguish the signal from the reductively retained compound signaling hypoxia from the thymidine retained through phosphorylation, signaling hypoxic response. EPR allows the images of the two processes to be distinguished by using spectrally distinct signals for measuring hypoxia and the peptide response to it.

2) The timings for the measurements of the radionuclide are similar while the EPROI is nearly immediate (it can be obtained in 10 minutes) and the signal response image will occur 1-3 hours later.

3) The EPROI is quantitative while the reductive retention image is qualitative. Radionuclide images depend heavily on access of the radionuclide to the location where oxygen is measured, and other aspects of local tissue reductive capability, (i.e., P450 reductase, xanthine oxidase etc.) activity. {Melo, 2000 #2229} For EPROI, as long as some spin probe reaches the location, the oxygen measurement depends only weakly on the signal amplitude. Rather it depends on the signal relaxation time or line width.

MRI has been used for molecular imaging. {Louie, 2000 #1395} This has been accomplished in the context of embryos half of whose cells express the reporter gene. While high spatial resolution is demonstrated, a very high concentration of reporter gene product is necessary. This is because the technology introduces contrast in a very high signal background. Weissleder et al. {Weissleder, 2000 #1673} show images of mouse tumors all of whose cells express the transferrin receptor which binds high contrast holo-tranferrin conjugated hyperparamagnetic iron oxide nano-particles. The contrast is seen against a large background water signal. This technology is unlikely to be useful to accomplish what is described herein for EPR images because of the small signal concentration that makes detection with MRI. Unlike MRI, the EPR technology involves activation of a "beacon in the dark".

In some embodiments, the present invention improves scientific knowledge, technical capability, and/or clinical practice in one or more broad fields. Here is an explanation of why to use EPR Imaging.

EPR images are obtained at excitation RF frequencies of very high field (6-7 T) MRIs that are presently being used for whole body human MRI {Vaughan, 2009 #2230} but because the magnetic moment of the electron is 658 times that of the water proton, magnetic fields are 1/658 times lower allowing low field inexpensive magnet systems ~90 gauss, 9 milliTesla (mT) at our operating frequency of 250 MHz. {Halpern, 1989 #89; Halpern, 1991 #899} This promises a low cost technology not specifically requiring expensive high field superconducting magnets, although standard field MRI is useful to provide anatomic correlates. EPR spectral linewidths of certain carbon centered spin probes, trityls, are specific and sensitive to local $pO_2$. {Halpern, 2003 #1798} The transverse relaxation times, or, equivalently, the spin packet line-widths of these spin probes are directly proportional to the local oxygen concentration. They give a direct quantitative readout of tissue micro-environmental $pO_2$. Using spectroscopic EPR imaging {Lauterbur, 1984 #177; Maltempo, 1986 #181; Halpern, 1994 #93; Epel, 2008 #2200}, spatial images of quantitative tissue $pO_2$ may be obtained from living animals. We propose here to obtain simultaneous registered images of cell signals responding to low $pO_2$ using nitrogen centered molecular beacons activated by hypoxia signaling coupled reporter proteins. These cell signal images would be spectrally distinct from the trityl based $pO_2$ images and could be obtained simultaneously with them. At 9 mT, carbon centered and the central manifold of $^{14}N$ have sufficiently different absorption frequencies (~8.4 MHz) that they are, effectively two color images. The readout frequencies are low enough to avoid poisonous non-resonant absorption to allow oxygen quantification deep in living tissue. {Halpern, 1994 #93} A variant project with simultaneous imaging of $pO_2$, HIF1α signaling and the vascular endothelial growth factor (VEGF) response to HIF1α would use carbon centered oxygen sensitive trityl radicals and $^{14}N$ and $^{15}N$ molecular beacons, effectively 3 color images automatically registered with each other.

In some embodiments, the concepts, methods, technologies, treatments, services, or preventative interventions that drive this field will be changed by the present invention.

In some embodiments, the present invention provides for the first time, automatic co-localization of micro-environment stimulus and cell signal response in native animal tissue and tumor environment, allowing their comparison. Distinct responses of normal and tumor tissue provide insight into therapies that can exploit these differences, targeting malignant tumors and sparing normal tissues. This opens a major avenue to the improvement of the therapeutic ratio for cancer therapy.

Approach used by some embodiments:

1. Electron paramagnetic resonance (EPR) oxygen images give uniquely sensitive, specific, spatially resolved and physiologically relevant images of oxygen distributions.

Figure 2:
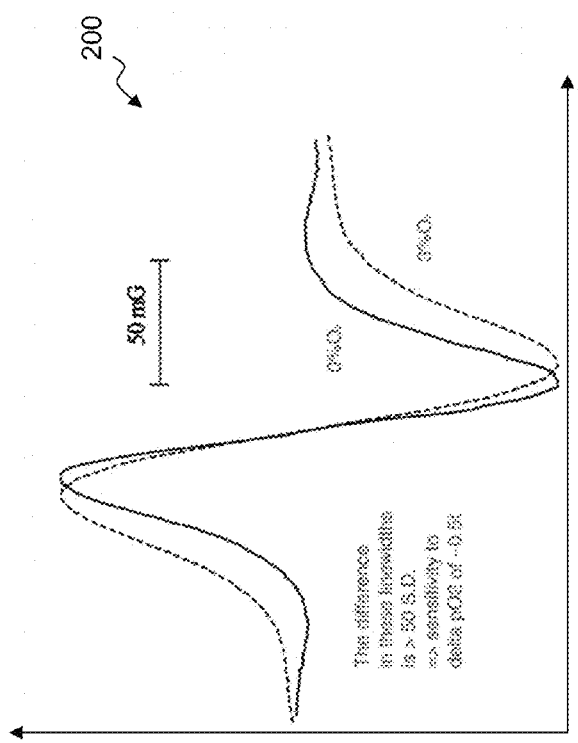
FIG. 2 is a graph 200 of spectral line widths of the spin probe under different oxygen concentrations showing that oxygen broadens the spin-probe spectral lines.

FIG. 2 is a graph 200 of spectral line widths of the spin probe under different oxygen concentrations showing that oxygen broadens the spin-probe spectral lines. The difference in the linewidths shown is >50 S.D., meaning a sensitivity to delta $pO_2$ of about 0.5 torr.

FIG. 3A is an EPR image of the volume-elements (voxels) of a single plane of voxels through the subject, wherein the color of each pixel of this image represents the signal strength of the spin echo signal from the corresponding voxel (the three-dimensional (3D) volume element that is one unit high in the vertical direction indicated in the figure, one unit wide in the horizontal direction indicated in the figure, and one unit thick in the dimension perpendicular to the plane of the image). Voxels (volume elements) in a 3D object correspond to pixels (picture elements) of a 2D image that are extended into a third dimension perpendicular to the plane of the image.

FIG. 3B is an EPR spectrum of one of the voxels of FIG. 3A. Note that in some embodiments, the corresponding EPR spectrum of each voxel (in the 3D volume being measured) is determined and stored for further analysis. In some embodiments, a color-coded image is generated from the spectra of each voxel, such that rather than the signal strength of each voxel such as shown in FIG. 3A, the line width, signal strength, ratios of measurements of a plurality of signals, and/or other attribute of the spectra of each voxel is displayed in the resulting image (e.g., the color, hue, and/or brightness of each element in the image being determined by one or more attributes of the spectrum of the corresponding voxel). In some embodiments, a computer system elicits and receives a pixel selection from a user (the user can move a pointer, using a mouse, and then hover over, or click on, a pixel of image 300 shown on a monitor), and the system would then display a spectrum 301 corresponding to the selected pixel in a window on the monitor, as indicated by FIG. 3A and FIG. 3B. In some embodiments, a representation showing three dimensions of an image (representing two or more parameters obtained from the received EPR signals) is calculated and displayed on a monitor. In some embodiments, images that combine information from regular MRI (nuclear magnetic imaging) and information from EPRI (electron paramagnetic imaging) are displayed and are manipulatable by the user to show various aspects, with the data from the MRI registered and/or superimposed on the data from the EPRI.

EPR Spectra of Specific Spin Probes Specifically and Sensitively Broaden in Response to Local Oxygen Concentrations.

EPR spectra from very-narrow-spectral-line compounds referred to as trityls show very specific and sensitive broadening in response to the presence of oxygen dissolved in local water. FIG. 2 shows distinct EPR spectral widths obtained in 30 s from a trityl in water equilibrated with 0 torr and 22 torr $pO_2$. For trityls, spectral width response is linear in $pO_2$ and minimally sensitive to confounding broadening from itself, viscosity and lower temperature. Because EPR is a magnetic-resonance technique, using magnetic field gradients, an EPR image of a sample can be obtained. Spectroscopic imaging of 1.6 mm trityl tubes, a 0.66 mm-thick plane of which is shown in FIG. 3A, gives a trityl spectrum from each image voxel. Each spectrum from each voxel gives the $pO_2$ of the voxel. From the above, continuous-wave spectroscopic images, having a spatial resolution of 1 mm and $pO_2$ resolution of 3 torr, are obtained in 30 minutes. From more recent electron spin echo measurements, images having 1 mm spatial resolution and 1 torr $pO_2$ resolution are obtained in about 10 minutes.

a. EPR Oxygen Images (EPROI) in Living Tissue/Tumor Agree Point by Point with "Gold Standard" Oxylite™.

FIG. 4 shows a graphical comparison 400 of Oxylite™ and EPROI voxel oxygen values: the four panels each showing two orthogonal planes of a single FSa tumor-bearing leg of a C3H mouse (wherein the tumors are not distinguished in these images), each pair of images flanking a graphical comparison of Oxylite™ $pO_2$ (shown by filled circles ●) with EPROI image voxel $pO_2$ (shown by open circles ○). An enlargement 401 of the left two panels of comparison 400 is presented in FIG. 4A. An enlargement 402 of the right two panels of comparison 400 is presented in FIG. 4B.

FIG. 4 shows comparison of EPROI $pO_2$ with the gold standard Oxylite™ in legs of C3H mice bearing FSa tumors. Two orthogonal planes of $pO_2$ are shown in FIG. 1 and here in each of the four panels of FIG. 4. A single track, visible as a fine black horizontal line in FIG. 4 in each plane/image is contained in both planes of each of the four sets of images. This line represents the path of an Oxylite fiberoptic $pO_2$ point oxymeter stereotacticly co-located or registered with the EPROI. The colorbar in each panel shows the EPROI $pO_2$ in torr. The graphs between the EPROI image planes show the $pO_2$ values from Oxylite (●) and $pO_2$ values from the co-located voxels of the EPROI (○). The agreement is good. {Elas, 2006 #1906} b. Tumor is Located in EPROI with Registered T2 MRI:

EPROI, co-registered with MRI allows the distinction of tumor from normal tissue voxels.

Figure 5:
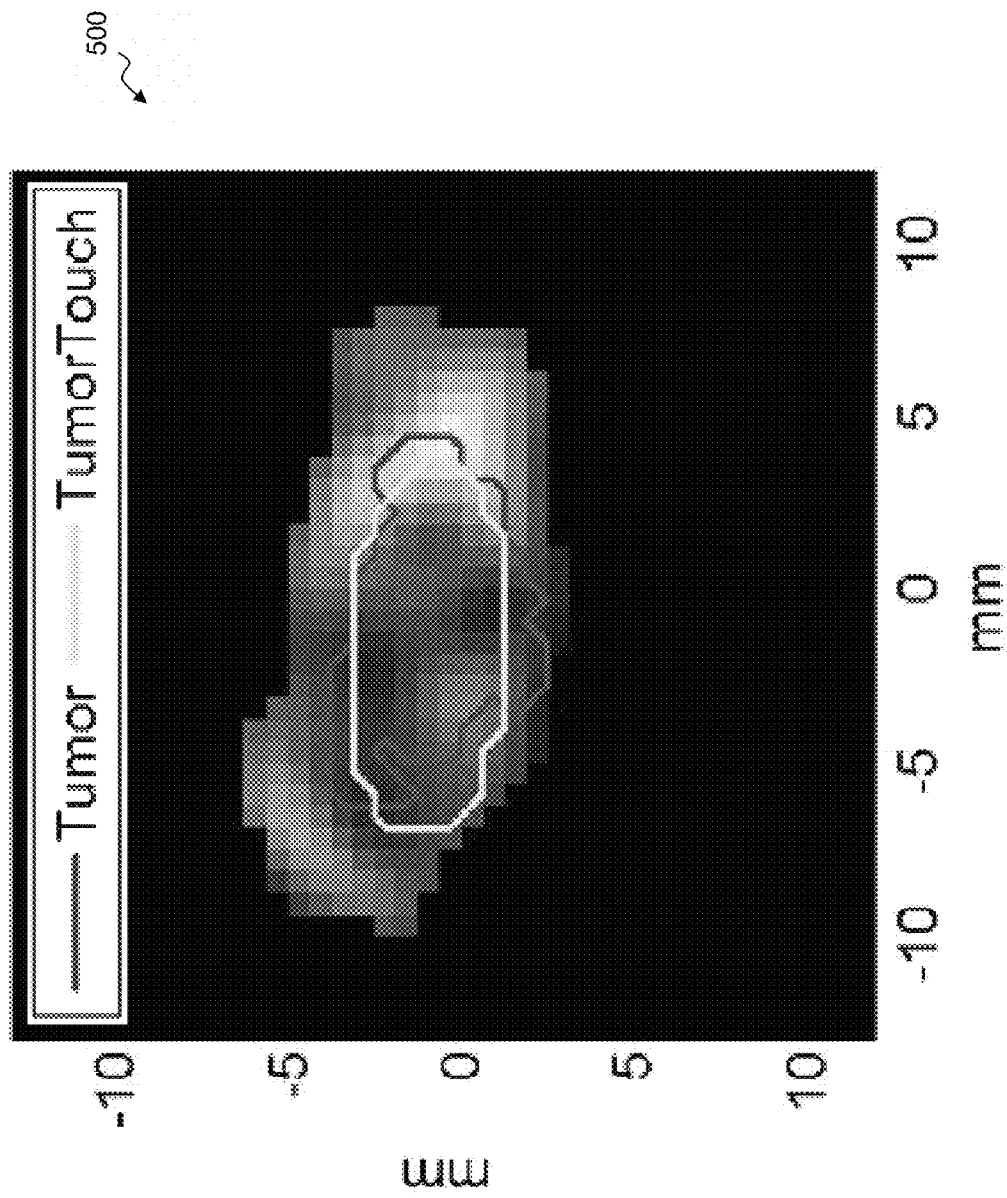
FIG. 5 is an EPROI image 500 with two contours overlaid on the EPR image.

FIG. 5 is an EPROI image with two contours overlaid on the image. The red contour shows the $T_2$-determined tumor contour from the MRI co-located or registered with the EPROI. The yellow contour is derived from the crossed diameters of the tumor giving an ellipsoid which was then fit to stereotactic locations of a needle tip touching the surface of the tumor. {Haney, 2009 #2194}

Figure 6:
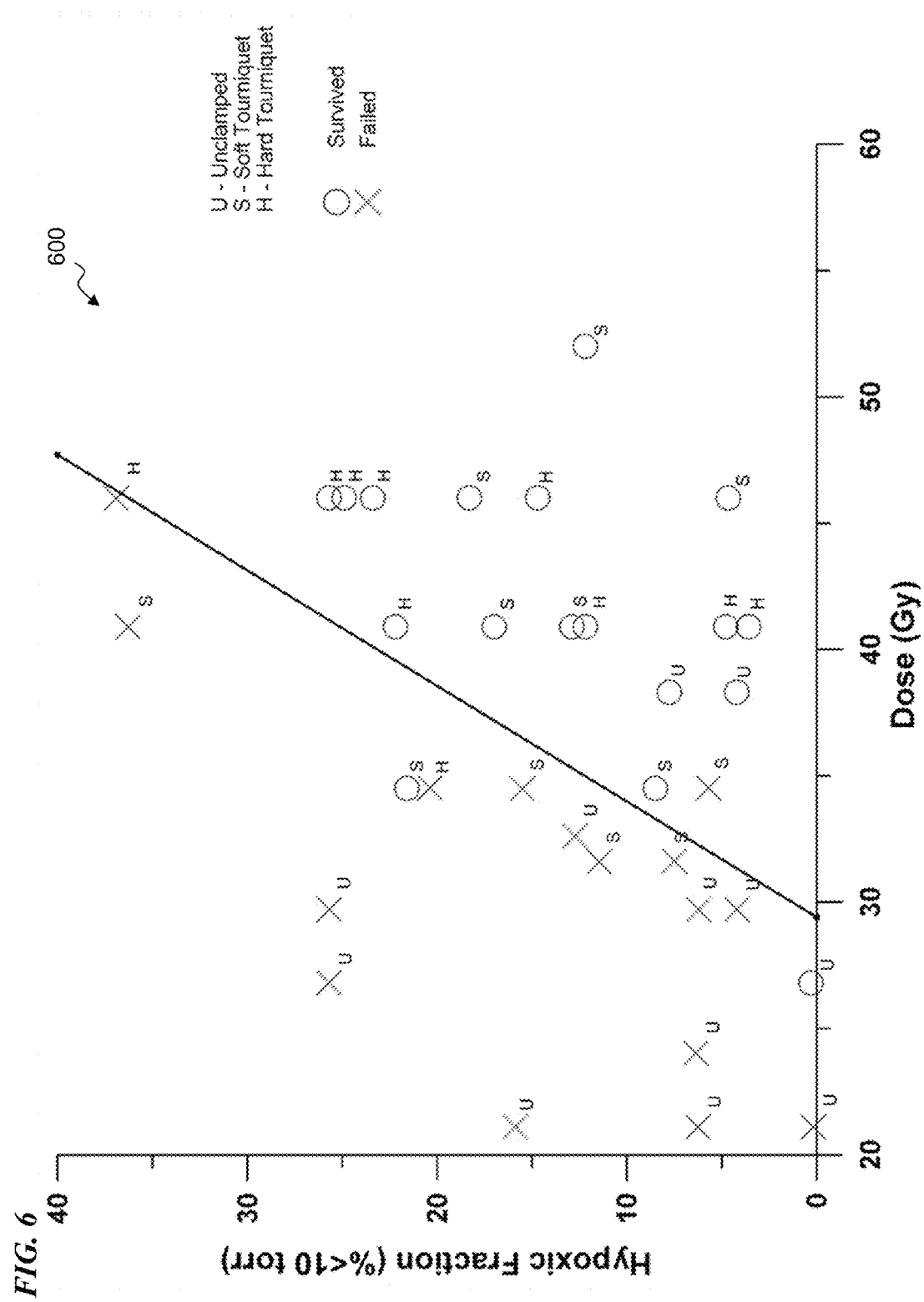
FIG. 6 is a scatter plot 600 of controlled tumors (○) and tumors that fail radiation (x), Hypoxic Fraction—% of EPROI voxels having less than 10 torr prior to radiation versus dose.

FIG. 6 is a scatter plot of controlled tumors (those that survived radiation each denoted by an open circle ○) and tumors that fail radiation (each denoted by an x), wherein the vertical axis is the hypoxic fraction—showing the percentage (%) of EPROI voxels less than 10 torr prior to radiation versus radiation dose.

Figure 7:
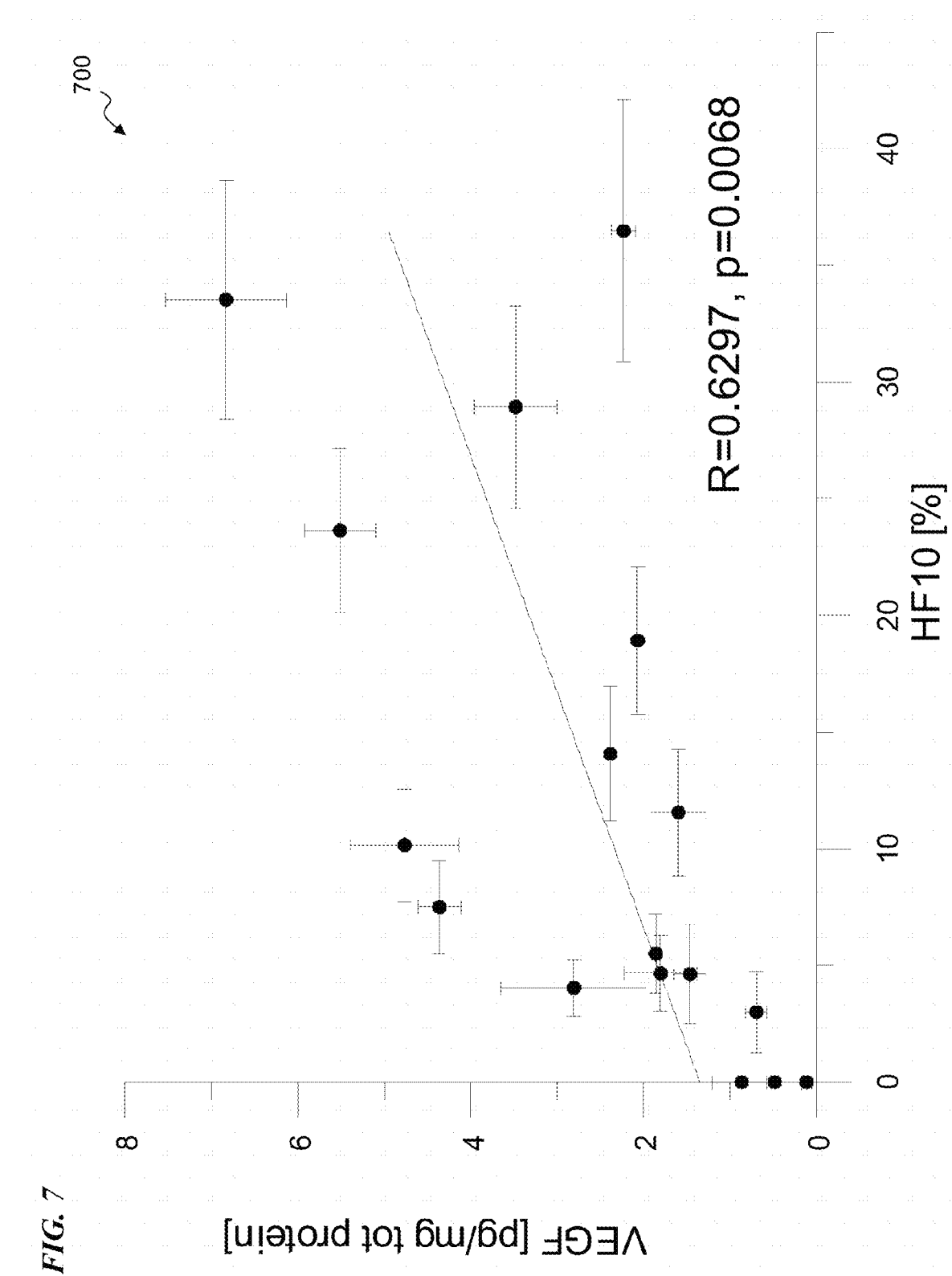
FIG. 7 is a scatter plot 700 of VEGF versus HF10.

FIG. 7 is a scatter plot of VEGF vs. HF10. (Vascular endothelial growth factor (VEGF) is a signal protein produced by cells that stimulates the growth of new blood vessels, a process called angiogenesis. HF10 is a measure of the hypoxic fraction (e.g., the percentage of voxels measured) at less than 10 torr.)

c. Fraction of EPROI Tumor Voxels<10 Torr (HF10) Enhances Prediction of Radiation Tumor Curability EPROI enables evaluation of the $pO_2$ of each tumor voxel and the fraction of tumor voxels with $pO_2$ less than a threshold. FIG. 6 {Elas, 2008 #2038} shows EPROI-based HF10 from 9-mm FSa fibrosarcomas in the legs of C3H mice. These were obtained just before their treatment with doses of X-ray doses near their $TCD_{50}$ (tumor-control dose where 50% of the treated tumors are controlled). The HF10 along as well as radiation dose significantly correlates, on bivariate analysis, with tumor cure. The regression provides a line on the scatter plot of tumor dose and HF10 that significantly better selects tumor cures (○) from failures (x) than dose alone. This is shown in FIG. 6. HF10 provides highest significance for correlation with eventual tumor cure.

d. Stereotactic EPROI Registered Vascular Endothelial Growth Factor (VEGF) Biopsy Negatively Correlates with $HF_{10}$ The stereo-tactic needle location used for EPROI and Oxylite comparisons used to provide biopsies that could be registered with the EPROI as pictured in FIG. 14. This allows measurement of the $pO_2$ of the voxels within the biopsy. With a number-11 (#11) biopsy needle, an inner diameter of 1.8 mm, 10-mm long biopsies gave ~100 voxels, enough for oxygen statistics and sufficient tissue for VEGF ELISA assay. Biopsy samples were suspended in lysis buffer containing 50 mM Tris pH 7.4, 3 mM EDTA, 20 mM β-glycerophosphate, and protease inhibitor cocktail (Fisher Scientific, Pittsburgh, Pa., USA) and homogenized for ELISA (Quantikine, Minneapolis, Minn.) for mouse VEGF. The relationship between all $pO_2$ statistics and VEGF concentrations in the biopsies was highly significant. However, the $HF_{10}$ was of highest significance. The scatter plot is presented in FIG. 7 p=0.0068 and Pearson product moment coefficient R=0.06297 indicating that ~⅝ of the variation is not random. {Colton, 1974 #1724}

2. Hypoxia Inducible Factor 1α (HIF1α) is the cellular protein regulator of response to hypoxia. This work aims to image increased levels of HIF1α registered with EPROI in vivo and in situ. In some embodiments, this is accomplished by locally infecting tumors with a viral vector with a HIF1α responsive reporter protein (RP) that activates the spectrum of an EPR molecular beacon (MB).

a. We Successfully Infected PC3 Tumor Cells with a Virus Encoding a HIF1α Responsive Matrix Metallo-Proteinase 2 (MMP2) RP to Report Cellular Hypoxia Response.

HIF1α promotes the cell response to hypoxia by binding to a specific DNA promoter sequence upstream of genes whose protein products orchestrate the cell response to hypoxia. This is referred to as a hypoxia responsive element (HRE). We constructed a hypoxia inducible reporter protein, MMP2, by inserting the MMP2 gene upstream of the HRE promoter. CMV inducible MMP2 cDNA was obtained from Oncogene (Siemens Healthcare Diagnostics Inc., Cambridge, Mass.). MMP2 cDNA was released from the pCMV6 vector using EcorI and XbaI. This MMP2 cDNA was ligated into the VQ.Ad5K-NpA shuttle vector using the same restriction sites, generating plasmid AD.MMP2. A 5×HRE promoter sequence was released from 5×HRE-Luc obtained from the laboratory of Dr. Amato Giaccia {Shibata, 2000 #1659} and cloned into AD.MMP2 using XhoI and HindIII enzymes. Viraquest (North Liberty, Iowa) packaged the construct in the adenoviral vector giving $4.4×10^{12}$ PU in 4 ml A195 buffer. Elevated levels of HIF1α signal, generated by hypoxia, attach to this viral reporter vector infected into cells to increase MMP2 RP.

FIG. 8A is a graph 801 showing MMP2 ELISA of PC3 cells infected with hypoxia-inducible MMP2 vector (MMP2) or empty vector (EMP) subjected to 4 hours of hypoxia (H) or normoxia (N).

FIG. 8B is a Zymogram 802 of MMP2 showing active protein as light bands above dark vertical arrow (H), none in adjacent lanes.

PC3 cells (available from ATCC (www.atcc.org), Manassas, Va.) are human prostate cancer cells, which, when grown in athymic nude mice (NCI (National Cancer Institute), Frederick, Md.), show minimal tissue invasion. Constitutive levels of MMP2 in PC3 cells have been shown to be low, ~2 ng/ml medium. (e.g., {Wilson, 2004 #2083}), confirmed by our ELISA graph shown in FIG. 8A. 5×105 cells grown in a six-well dish containing 3-5 ml complete F12 medium were exposed to 1.1×109 PU vector (10 µl in PBS+3% sucrose) for 3 hours. MMP2 ELISA (Quantikine, available from R&D Systems, Minneapolis, Minn. (a division of Techne Corporation)) measured pro- and active forms of MMP 2 in the supernatant of the cells after the hypoxic procedure. Cells were washed three (3) times in PBS and resuspended in 2 ml serum-free F12 medium at 37° C. for four (4) hours, during which they were exposed either to hypoxia, 3.5 torr (MMP2 H in FIG. 8A), or normoxia, room air (MMP2 N), where solution pO2 was measured with an Oxylite™ oximeter. Empty vector under hypoxia (EMP H) and normoxia (EMP N) are also shown with low MMP2 levels. Hypoxia enhances MMP2 level by over an order of magnitude relative to normoxia validating the success of the infection of the hypoxia responsive vector and the extracellular export of the reporter MMP2.

The Gelatin Zymogram (using Novex Precast Gel, available from Invitrogen, Carlsbad, Calif.) treated with Coomassie Stain was used to evaluate MMP2 activity. Supernatant was electrophoretically analyzed showing clearing of the blue dye where MMP2 activity was present. The white spot in FIG. 8B is a positive 100 ng/ml MMP 2 control The faint line above the arrows shows MMP 2 activity induced by exposing the PC3 cells to hypoxia, 0.2% oxygen over 4 hours. The normoxic bands to the right of each arrow show no activity.

b. Vascular Endothelial Growth Factor (VEGF) Responsive Element is a Downstream Response to Hypoxia, Stimulating Vessel Growth.

Although VEGF, produced in response to HIF1α, is usually activates cell membrane VEGF receptors, VEGF itself promotes transcription of Tissue Factor. As above with HIF1α, will use a VEGF responsive element (VRE) defined in the laboratory of Dr. Erhard Hofer {Mechtcheriakova, 1999 #2087} Department of Vascular Biology and Thrombosis Research at VIRCC, University of Vienna, Vienna, Austria. This is described more fully in the Specific Methods Section. The optimization of the VRE will follow procedures defined for the HRE in {Shibata, 2000 #1659}.

c. Molecular Beacons (MB) Will be Activated by the MMP2 RP. MBs are Peptide Linked, Broadened Nitroxides that can be Transformed into Narrow Detectable Nitroxides Via MMP2 Hydrolysis.

FIG. 8C is a sequence 803 of chemical formulae for synthesis of peptide-linked nitroxides.

Synthesis of Peptide-Linked Nitroxides:

The scheme of FIG. 8C depicts the attachment of nitroxides to a small peptide, incorporating a localized high concentration of a specific nitroxide, which at physiological pH is positively-charged. In a typical experiment shown in FIG. 8C, nitroxide [2] is covalently attached to the small peptide [1] using BOP (benzotriazole-1-yl-oxy-tris-(dimethylamino)-phosphonium hexafluorophosphate) as the linking agent {Castro, 1975 #2093} to afford peptide-linked nitroxide [3]. Since the pKa of the amine in the piperazine ring of [3] is >9.0, at physiological pH peptide-linked nitroxide [3] should predominately exist in a 4+ charge state.

Synthesis of Peptide-Linked Nitroxides:

The Scheme 1 shown in FIG. 8C depicts the attachment of nitroxides to a small peptide, incorporating a localized high concentration of a specific nitroxide, which at physiological pH is positively-charged. In a typical experiment shown below, nitroxide [2] is covalently attached to the small peptide [1] using BOP (benzotriazole-1-yl-oxy-tris-(dimethylamino)-phosphonium hexafluorophosphate) as the linking agent {Castro, 1975 #2093} to afford peptide-linked nitroxide [3]. Since the pKa of the amine in the piperazine ring of [3] is >9.0, at physiological pH peptide-linked nitroxide [3] should predominately exist in a 4+ charge state.

This compound demonstrates that when more than one nitroxide is bound in close proximity to another nitroxide, the spectrum of the nitroxide [3], is significantly broadened. Here the peptide-linked-nitroxide spectrum shown in FIG. 9 has an amplitude an order of magnitude less than the same compound after exposure to MMP2. These spectra demonstrate that the RP converts the MB from virtually invisible to visible. This will be the basis of the EPR-based reporter construct. The reporter protein will hydrolyse the peptide=linked nitroxide dimer converting the spectrum from one like that from compound [3] to that from [2].

FIG. 9 is a graph of the spectrum of Nitroxide molecular beacon (MB):

a) before MMP2, and
b) after MMP2

FIG. 10 is a graph of the simulated EPR spectrum of $^{15}$N-nitroxide plus trityl at 250 MHz 3. Trityl+$^{15}$N-nitroxide spectrum simulation: FIG. 10 shows a simulation of the trityl (central line) and $^{15}$N-nitroxide (flanking lines) at 250 MHz. The unequal distance between the carbon-centered trityl and the $^{15}$N lines reflects Breit-Rabi oscillations. The information from each is fully resolved. The field difference between the low field nitroxide line and the trityl line is large enough so that individual images can be obtained simultaneously.

4. Specific Approach-Basic Method: Developing an EPR signal responding to hypoxia signaling.

Hypoxia slows the degradation of constitutively transcribed/translated HIF1α. In some embodiments, PC3 tumors in athymic nude mice are locally infected with an adenovirus containing either a hypoxia responsive element (HRE) or a vascular endothelial growth factor (VEGF) responsive element (VRE) that will promote the production of the reporter protein matrix metalloproteinase 2 (MMP2), EC 3.4.24.24.

This has peptide sequences that activate the process of export from tumor cells into the extracellular fluid where it is activated. {Bremer, 2001 #1407} Active MMP2 hydrolyses a specific peptide sequences, including glycine-proline-leucine-glycine-valine-lysine (GPLGVL) at the glycine-valine site. A transmitter spin probe activated by MMP2 hydrolysis will be injected into an animal that will allow us to image the hypoxia induced transmitter probe registered with an EPR oxygen image. This process is shown in FIG. 11 and the result in FIG. 9.

FIG. 11 is a schematic diagram of the EPR transmitter probe (EPRTP) activated by the MMP2 reporter protein.

As with florescence, nearby EPR transmitter spin probes or other paramagnetic species broaden the EPR line, making it impossible to detect. They "quench" the signal. We develop an initially invisible-to-EPR-spectroscopic-sensing (see spectrum 1111), "quenched" spin probe molecule 1101 by tethering either two narrow-line 15N-nitroxides or a nitroxide and a gadolinium chelate via a polypeptide linker, GPLGVL, that can be hydrolysed by the MMP2 reporter protein. This hydrolysing will separate the two nitroxides into a pair of pieces 1102, eliminate the self "quenching" and make the piece with the "de-quenched" spin probe spectroscopically visible (see spectrum 1112) and imagable. Significant broadening of nitroxides attached to the terminus of the dendrimer {Rosen, 2003 #1548} has been observed, and preliminary results show the broadened spectrum from a multinitroxide peptide. FIG. 11 shows the process of cell signal activation of the EPR transmitter probe by the MMP2 reporter protein.

Sensitivity of the Basic Method: The sensitivity of the method should be addressed before attempting signaling images. The following calculation indicates feasible spin-probe concentrations for detection/imaging cell signaling in vivo. Estrogen Receptor (ER) on breast cancer cells is an example of an actively expressed signaling protein. One may infer concentrations of signal protein from measures of ER concentrations. High ER tissues express more than 100 fmol/mg tissue protein and often higher than 500 fmol/mg tissue protein.

Protein is approximately one-half (½) the dry cell weight, or 18% of the cell mass. {Alberts, 1994 #40} There are approximately $10^6$ cells per mg. tissue. Therefore there are approximately $6 \times 10^6$ cells per mg-protein. Given that there are $\sim 10^9$ receptors per fmol., 500 fmol/mg protein gives $\sim 10^5$ receptors per highly ER positive cell. For $10^{12}$ cells per L, this gives $10^{17}$ receptors per liter, or per kilogram or about 0.1 micromolar. This number reflects an inducible signaling protein and therefore is a good representation of the expected concentration of a transcriptionally inducible peptidase. Asking that each of the $10^{-7}$ M peptidase molecules hydrolyse a thousand (1000) peptide bonds results in a 100-micromolar local concentration of narrow-line spin probe. Delivery of 50-100 micromolar di-nitroxide into tissue would provide the $\sim 100$-200 micromolar of released spin probe. This is not an unreasonable concentration of di-nitroxide and should yield a measurable and an imagable concentration of trityl or narrow line nitroxide. The oxygen images already obtained derive from 200 µM of OX063 trityl spin probe which has a peak-to-peak line width close to that of a wo line deuterated pyrroloxyl {Halpern, 1990 #850; Halpern, 1993 #91} strongly suggest the feasibility of an EPRI image with the properties described above.

i. Biopsy Assay of HIF1α Signaling Registered with an EPR Oxygen Image (EPROI)

Figure 12:
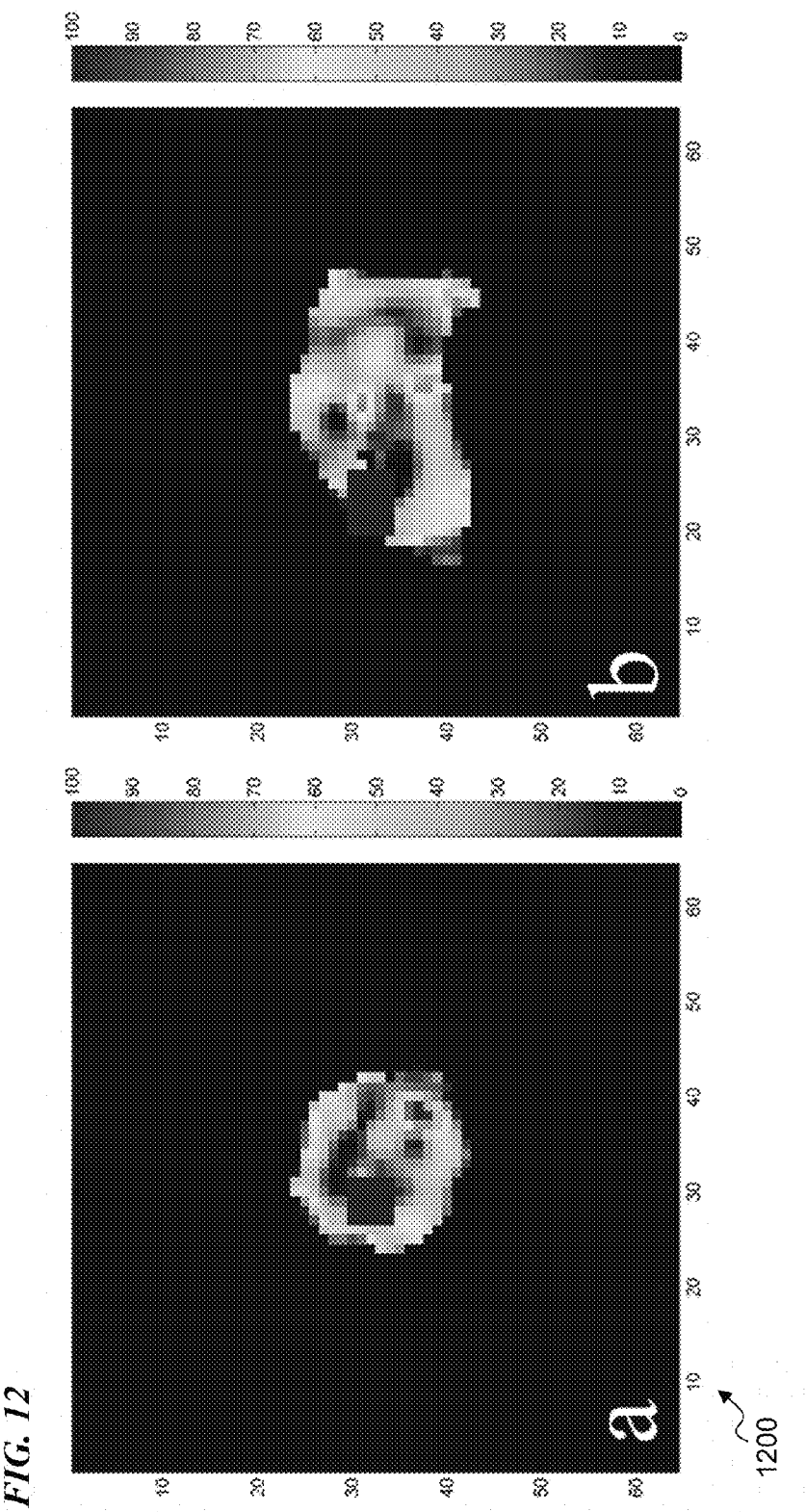
FIG. 12 shows two cross-sectional EPRO images 1200, image a (e.g., in an X=0 plane) and image b (e.g., in an Y=0 plane), that indicate the location (dark red voxels) for taking a biopsy in the EPROI-imaged volume.

FIG. 12 shows two cross-sectional EPRO images, a and b (image a (e.g., in an X=0 plane) and image b (e.g., in an Y=0 plane)), that indicate the location (dark red voxels) for taking a biopsy in the EPROI-imaged volume.

Basic Approach:

We have developed an infections adenoviral vector with a hypoxia-responsive element (HRE), the binding domain of the HIF-1α/HIF-1β heterodimer, which induces transcription of the reporter protein human MMP2. In preliminary studies, it was shown that hypoxia signaling in PC3 human prostate cancer cells infected with the viral vector gave increased levels of active MMP2 in response to hypoxia. In some embodiments, PC3 cells are grown in the legs of athymic nude mice. The viral vector will be stereotactically injected in regions of high and low $pO_2$ as determined by an EPROI. After allowing 4 hours for viral infection, hypoxic transcriptive response and MMP2 export, shown to be adequate in vitro, biopsies will be obtained as shown in FIG. 12. MMP2 will be quantified via ELISA. Quantified MMP2 will be correlated with mean, median $pO_2$ and HF10 of EPROI biopsy voxels shown as the red voxels in the EPROI of FIG. 12, with the $pO_2$ colorbar to the right.

Rationale: One of the promises of the EPR molecular imaging is its ability to image both fundamental aspects of the biologic milieu to which the animal's cells/tissue cell aggregates are responding and the response itself. Having established both EPROI and in vitro success of the viral vector's response to hypoxia, a first step to establish the native in vivo methodology is to correlate the oxygen image and a stereotactic biopsy registered with the oxygen image. The signal monitored for these experiments is MMP2 measured via ELISA.

Brief Methods:

Plasmid cDNA with an optimal hypoxia promoter have been obtained from Dr. Amato Giaccia's lab at Stanford, who have investigated various HRE configurations to optimize the hypoxia promotional activity. {Shibata, 2000 #1659; Fink, 2002 #1676}. The MMP2 gene was obtained from Viroquest. These sequences were verified and ligated in the laboratory of Dr. Ralph Weichselbaum and the ligated cDNA was sent to Viroquest for the insertion in adenoviral vector and generation of adenoviral particles, yielding $4.4 \times 10^{12}$ PU.

Figures 13A, 13B:
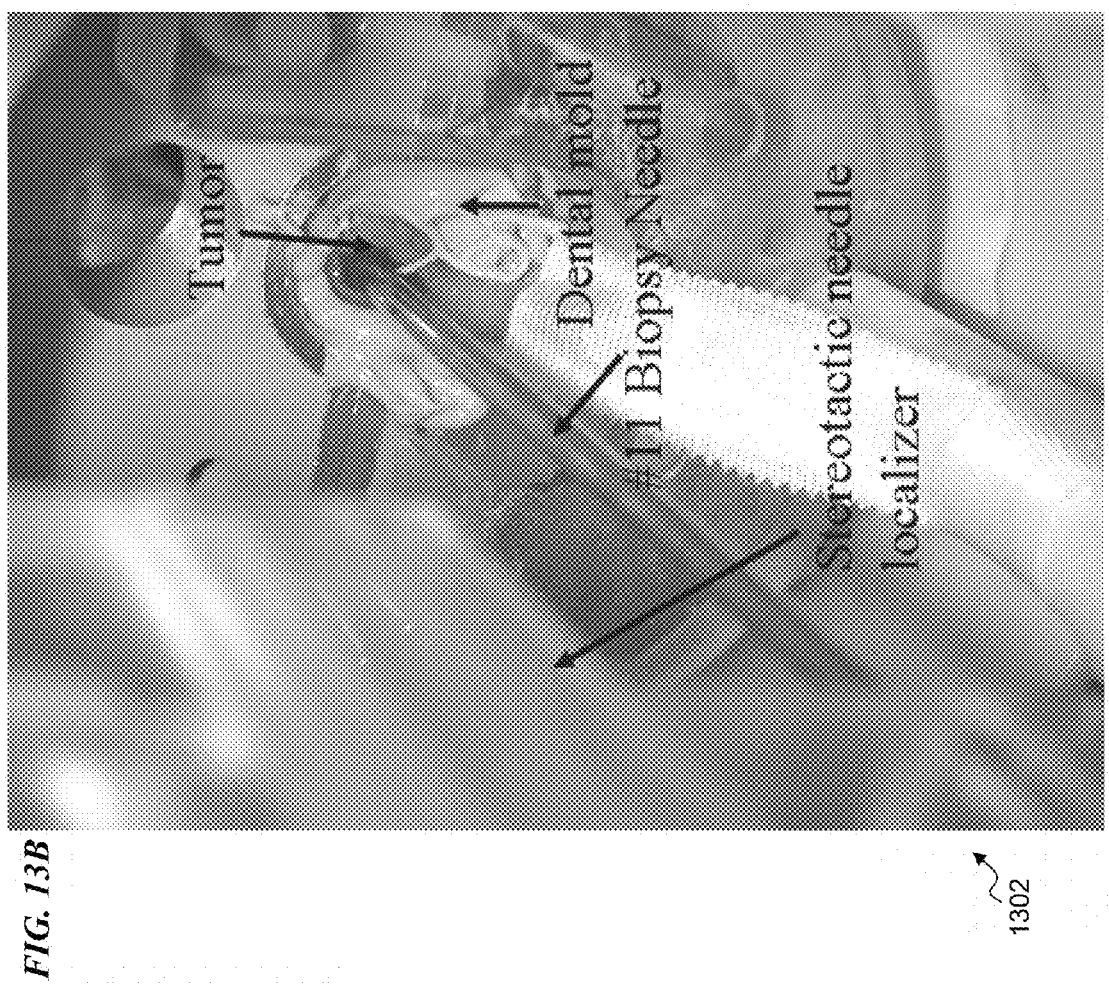
FIG. 13A is an illustration 1301 of Scheme 2, wherein hypoxia (i.e., reduced oxygen) results in increased MMP2.
FIG. 13B is a photograph 1302 illustrating a simple scheme for obtaining a tumor biopsy in the imager of the present invention.

FIG. 13A illustrates Scheme 2, wherein hypoxia (i.e., reduced oxygen) results in increased MMP2 (Hypoxia/$\downarrow O_2 \Rightarrow \uparrow$MMP2).

FIG. 13B is a photograph illustrating a simple scheme for obtaining a tumor biopsy in the imager.

In some embodiments, PC3 cells are grown in the legs of Sprague-Dawley athymic nude mice (Indianapolis, Ind.). We have some experience with these tumors {Haney, 2009 #2092}. In some embodiments, a titanium-tipped #11 breast biopsy needle (C. R. Bard, Tempe, Ariz.) is used; administered with vacuum suction. This has proven necessary due to the scirrous, lobular consistency of these tumors which can distort the tissue and/or bend even a #11 needle.

In some embodiments, biopsy samples are homogenized in 50 mM tris-HCl pH 7.4 buffer with 1 mM monothioglycerol and centrifuged at 2000 g. The supernatant representing cytosol and extracellular fluid is subjected to MMP2 ELISA. The ELISA assay intended for use in these experiments is designed to detect only the active form of MMP2 (Biotrak MMP-2 ELISA; GE Healthcare Life Sciences).

Anticipated results/potential problems & solutions: In some embodiments, this experiment in itself will provide novel cell signaling biology in a native tissue environment. The biopsy will also provide MMP2 levels that will help us understand quantitative systematics of the protein signal response system. For example, it will allow more accurate estimation of the quantity of EPR transmitter probe (EPRTP) that will be necessary for the subsequent EPR signal image. One potential problem lies in the hetereogeneity of oxygen images. This may cause averaging, obscuring variations in the EPROI. This should be circumventable by dividing the heterogeneous cores into corresponding high and low $pO_2$ sections from the image and combine the parts of the cores. The needle also has a tendency to be deflected by the fibrous periphery of the PC3 tumors. In some embodiments, the apparatus is implemented in steel to make it more rigid.

Ii. VEGF Responsive Element (VRE) Exploring Spatial Patterns of Vasculogenesis.

a. Hypothesis/Rationale.

It is hypothesized that quantitative in vivo tissue hypoxia imaged with EPROI will correlate spatially with in vivo VEGF signaling. This has been measured in vitro and imaged qualitatively in vivo. {Stephen, 2007 #2084; Gillespie, 2007 #2085; Lungu, 2007 #2086} However, registered images of chronic hypoxia and VEGF signaling have not, here-to-fore been presented. Building on our success in the construction of a Hypoxia Responsive Reporter Protein, we will enhance insight into the oxygen biology of native tissue with this technique.

Figure 14:
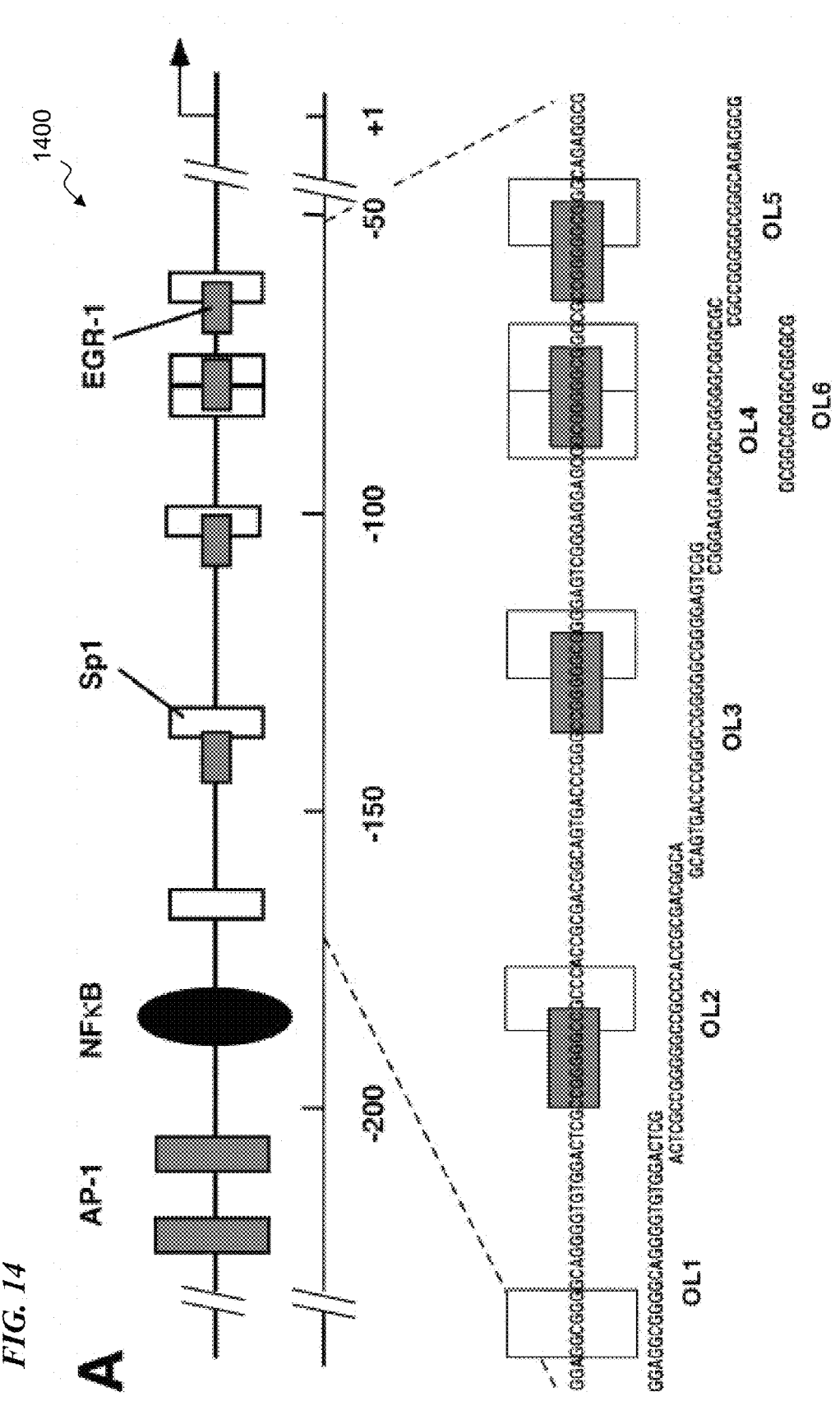
FIG. 14 is a schematic representation 1400 of the VEGF Response Element.

FIG. 14 is a schematic representation of the VEGF Response Element.

b. Experimental Design.

The DNA sequence of a VEGF response element has been defined {Mechtcheriakova, 1999 #2087; Schabbauer, 2007 #2095} in a promoter region of a Tissue Factor (TF) response element to VEGF protein as shown in FIG. 14 (VEGF Response Element).

This GC-rich region involves DNA-binding and cooperation of two transcriptional factors—EGR1 and Sp1 in response to VEGF signaling. We will construct reporter plasmids with 1, 3 and 5 copies of this element upstream of the MMP2 reporter protein in as was done with HIF1α. Our success with this is described in the Preliminary Studies section. This will provide the optimal VEGF response element (VRE) as for the HRE. {Shibata, 2000 #1659} These plasmids will be transferred to Viraquest for generation of an adenoviral-based vector with an MMP2 as described in the preliminary studies section above.

In Vitro Tests:

The construct will be tested in the fashion described for the HRE based hypoxia signaling vector in Preliminary studies. This will involve subjecting the PC3 tumor cells to hypoxia and assaying the medium for increased MMP2. These cells have been seen to have significant VEGF signaling. {Timke, 2008 #2091} We will stimulate the cells with hypoxia, 3.7 mmHg $pO_2$. The cell medium will be assayed for MMP2 protein via ELISA and for MMP2 activity using gelatin based zymograms as is described in detail in the Preliminary Studies section. These studies will establish levels vector PU that will be applied for in vivo studies.

In Vivo Initial Tests:

EPROI will be obtained from PC3 tumors growing SC in the legs of athymic nude mice. The vectorized VRE-reporter construct will be injected along tracks with high and low $pO_2$. Biopsies will be obtained from these tracks as indicated above, four hours after the vector is administered. These will be assayed for both VEGF protein in the entire sample and active MMP2.

Anticipated Results, Problems and Solutions to them.

We anticipate that these experiments will demonstrate a pattern of VEGF signaling similar to that of the HIF1α signaling experiment above. EPROI registered ELISA for both VEGF and MMP2 will establish, in native conditions, the quantitative relationship between the stimulating protein and the transcriptional response to it. This will enhance our understanding of the native signaling process. If unexpected dissimilarity between the HIF1α and VEGF signaling does occur, this is of interest. We can further analyze the specimens for factors that may modulate the VEGF response, e.g., tissue VEGF neutralizing antibody. {Pourgholami, 2008 #2088} It will also provide the general levels of MMP2 response via the VRE, giving us systematic levels of EPR transmitter probe that will be necessary.

Iii. EPR Transmitter Probe (EPRTP) Activated by MMP2 Reporter Protein.

a. Hypothesis/Rationale.

In the preliminary studies section above we describe the synthesis of peptide-linked nitroxide [3] in which nitroxides are connected to the amines along the backbone of the peptide. The EPR spectrum of [3] is broad, showing quenching of the proximate nitroxides. The "de-quenched" nitroxide monomer [2] has a typical narrow three-line EPR spectrum. The success in preparing a peptide-linked nitroxide [3] suggests that by substituting a linker which is substrate for the signal reporter MMP2, we can follow cellular signaling with the onset of nitroxide spectral signal via MMP2 hydrolysis.

b. Experimental Design. Syntheses of Nitroxide-Containing Peptides, as Substrates for MMP-2

Synthesis procedure.

Figure 15A:
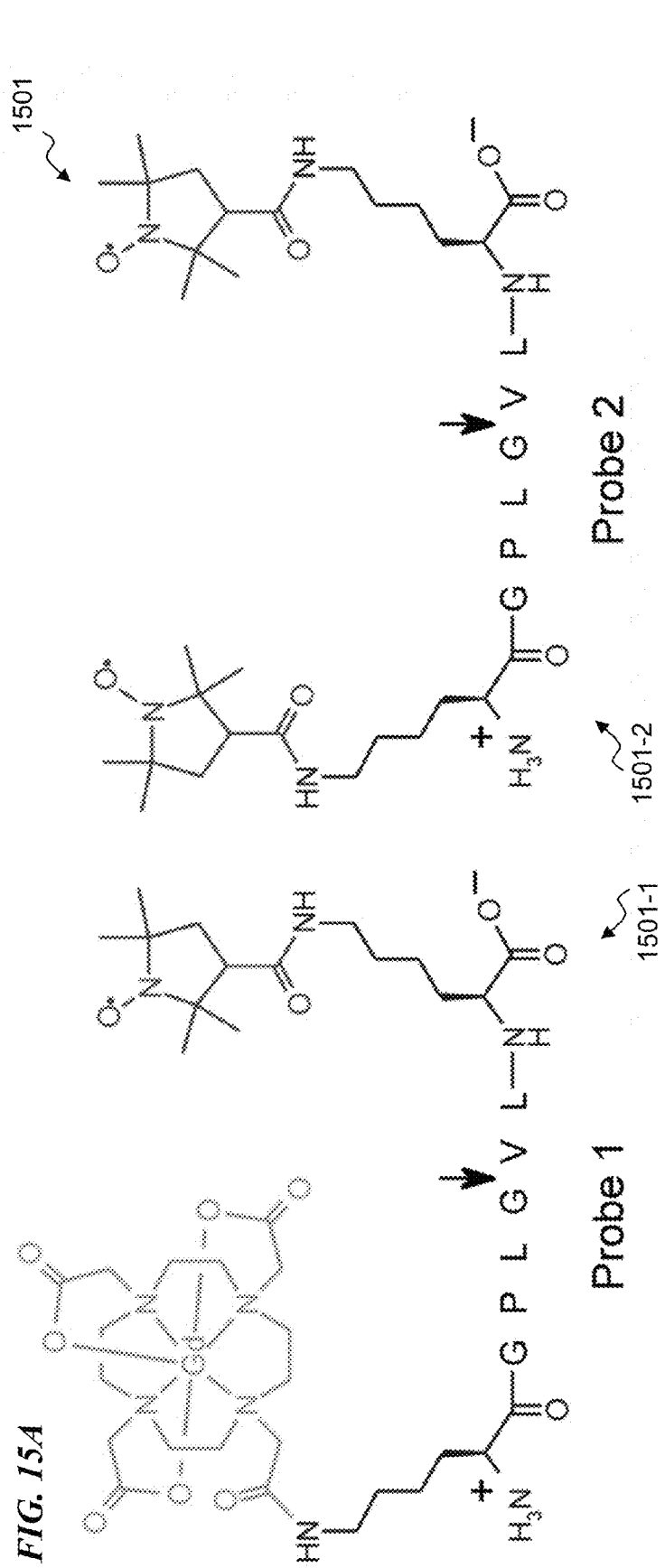
FIG. 15A shows chemical formulae 1501 of two probes 1501-1 and 1501-2.

FIG. 15A shows chemical formulae of two probes. The linker hydrolysis site is indicated by the arrow. Boc protection chemistry will be used for peptide synthesis.

Probe 1 of FIG. 15A: The C-terminal lysine ∈-amino will be protected with Cl—Z. The next six (6) residues comprising the MMP2 substrate sequence will be incorporated through standard Boc chemistry. The N-terminal lysine will have Fmoc-protected α-amino and Boc-protected ∈-amino. On-resin Boc removal exposes the N-terminal ∈-amino for conjugation to the free carboxyl group of tris(tert-butyl) ester of DOTA (Macrocylics, Dallas, Tex.). Subsequent HF treatment deprotects Boc and Cl—Z protective groups and cleaves the peptide from the resin, but leaves the N-terminal Fmoc intact. 2H,15N-Proxyl-3-carboxylate will be conjugated to the now-unprotected C-terminal lysine side chain. Thereafter, treatment with piperidine removes the sole remaining protective group (Fmoc) to yield the doubly-conjugated peptide. Complexation of the DOTA moiety with Gd3+ then yields the fully functional Probe 1. (See FIG. 15)

Probe 2 of FIG. 15A: The C-terminal lysine ∈-amino will be protected with Cl—Z. The next 6 residues comprising the MMP2 substrate sequence will be incorporated through standard Boc chemistry. The N-terminal lysine will have Fmoc-protected α-amino and Boc-protected ∈-amino. HF treatment cleaves the Boc and Cl—Z protective groups and cleaves the peptide from the resin, but leaves the N-terminal Fmoc intact. 2H,15N-Proxyl-3-carboxylate will be conjugated to both unprotected lysine ∈-amino groups. Subsequent piperidine treatment removes the N-terminal Fmoc group to yield full functional Probe 2.

Figure 15B:
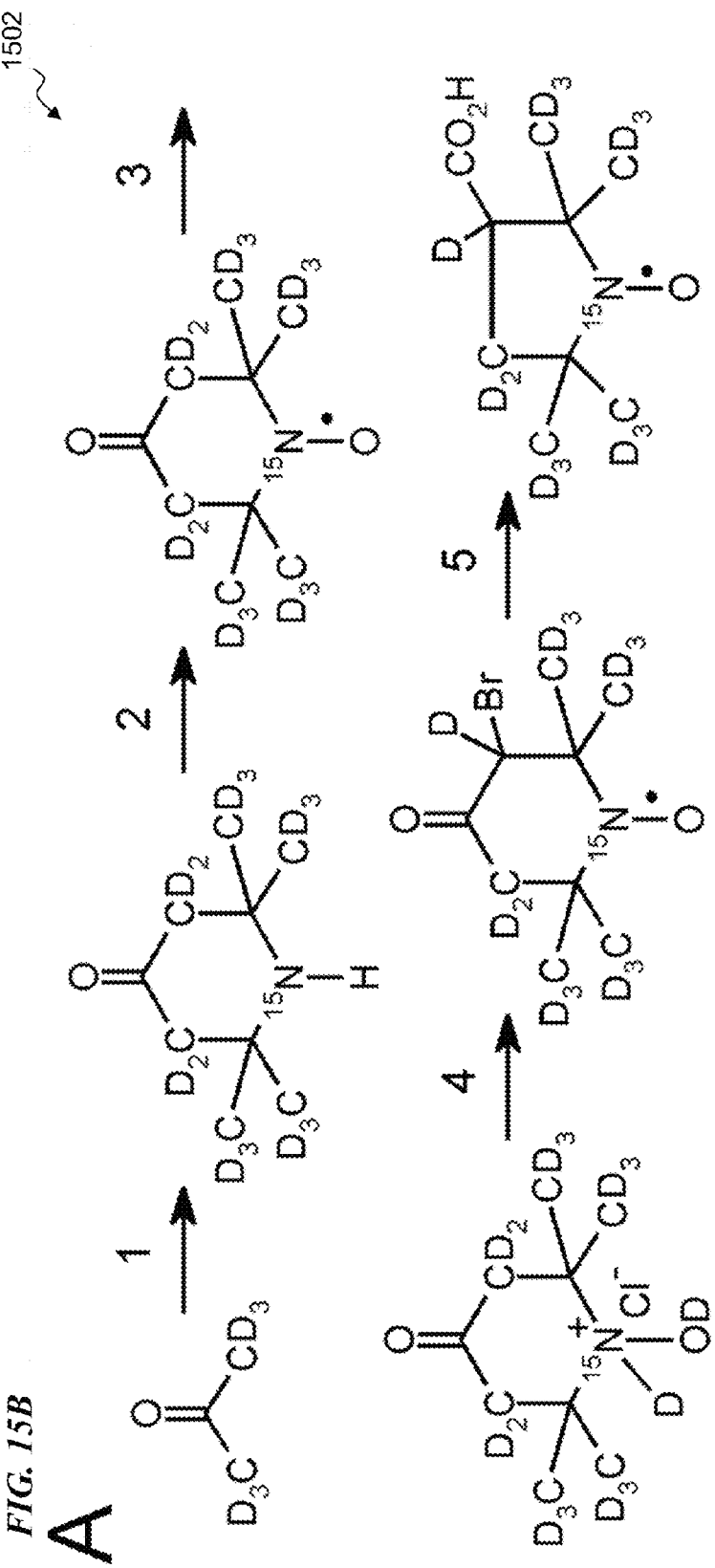
FIG. 15B illustrates a Scheme A for synthesis 1502 of 15N-perdeuterated nitroxides.

FIG. 15B shows a scheme "A" for synthesis of 15N-per-deuterated nitroxides. Perdeuterated nitroxides: In some embodiments, 15N-perdeuterated nitroxides will be synthesized as in Scheme A of FIG. 15B and detailed in {Burks, 2009 #2081; Lin, 1990 #118}

General Procedures.

All synthetic intermediates will be purified chromatographically. Non-paramagnetic compounds will be characterized by NMR spectroscopy and paramagnetic compounds will be analyzed by elemental analysis. High-resolution mass spectra will be acquired for all species. The functional Probes 1 and 2 will be analyzed by EPR spectroscopy (and the effect of MMP2 cleavage on the EPR spectra will be quantified). After full in vitro characterization, the probes will be tested by in vivo EPR imaging in the Halpern laboratory.

c. Anticipated Results.

Since we have already prepared of peptide-linked nitroxide [3] (as described above in the preliminary studies section) and have developed synthetic methods to link nitroxides to peptides, we expect that preparation of peptide-linked nitroxides Probes 1 and 2 should proceed without encountering any difficulties.

One key spectroscopic strategy: In some embodiments, the $^{15}N$ nitroxide from the cell signaling have two spectral lines separated by over 1 mT from the single line of the trityl used in the EPROI. Spectroscopic images of oxygen concentration and signaling intensity can be obtained simultaneously and automatically registered.

d. Potential Limitations.

The chemistry used for peptide synthesis and conjugation of the paramagnetic moieties is well tested. Therefore, we do not anticipate any significant problems in making the proposed molecular probes. Probe 2, with two conjugated nitroxides, has the potential to show an artifact—bioreduction of one of the nitroxides would leave the other, intact nitroxide unquenched. That is, if there is significant bioreduction, it is possible that an EPR signal could be generated in the absence of MMP2 activity (a false positive). We believe this is not likely to be a major problem, because we have shown that the aceto-methoxy ester of the proxyl nitroxide used in the probe is remarkably resistant to bioreduction. {Burks, 2008 #2101} Nevertheless, in the unlikely event that Probe 2 proves problematic, Probe 1 is expected to be free of this potential artifact—the Gd(III) chelate is completely resistant to metabolism, while any bioreduction of the nitroxide merely "silences" the probe, so that no signal can be generated irrespective of MMP2 activity. {Lin, 1990 #118; Burks, 2009 #2081}

Iv. Imaging Hypoxia with EPR Oxygen Image and HIF1 Signaling Image

Basic Approach/Rationale.

Animal tumors will be infected by the adenovirus coding the hypoxia response element upstream of the MMP2 reporter protein which, we have shown, is exported to the extracellular compartment and activated. The MMP2 reporter hydrolyses the EPRSM linked via GPLGVL peptides to $^{15}$N-perdeuterated nitroxides. This narrows the nitroxide spectrum and making it visible and imagable. Signaling images will be obtained simultaneous with EPROI. This will allow automatic registration of millimeter resolution images of oxygen and signal response images. The hypoxia signaling process is indicated in Scheme 3.

FIG. 15C illustrates Scheme 3 labeled 1503 wherein hypoxia or reduced oxygen results in increased MMP2, which is used to cut dinitroxide which then results in increased EPR signal (Hypoxia/$\downarrow O_2 \Rightarrow \uparrow$MMP2$\Rightarrow \times$ Dinitroxide$\Rightarrow \uparrow$EPR Signal).

Brief Methods:

The human prostate cancer cell line PC3 will be grown in the hind limbs of athymic nude mice. These tumors will be of linear dimension 8-10 mm in 25 g mice. Vector will be administered by intratumoral injection along a single track according to the EPROI, selecting a track with large $pO_2$ gradients. $10^9$ PU will be injected along the ~12 mm track. After waiting four hours, for vector infection and gene expression, all animals will be anesthetized with isofluorane gas anesthesia. Double lumen catheters will be placed in the urethra of all animals to allow the flushing of the trityl which accumulates rapidly in the bladder. {Haney, 2006 #1876} A solution yielding 200-400 µM dimers linked via GPLGVL peptides to $^{15}$N-nitroxides will be administered via tail vein injection. Nitroxides are well tolerated by mice at these concentrations. {Halpern, 1994 #93} Initially, measurement of the EPR spectrum in the tumor will demonstrate both the broadened spectrum from the peptide linked nitroxides and the narrow signal from the hydrolytic action of MMP2 on the peptide linker. Time sequences of non-imaging EPR spectra will measure the time course of the onset of narrow line signal in this system. This should determine the optimum time for imaging.

When an optimal time point has been determined, signaling images will begin. This will be at a time equal to the optimum narrow line spectrum for dimers minus half the imaging time. At this time OX063 oxymetric spin probe will be administered to the animals at doses of 0.5 g/kg to 1 g/kg via tail vein. A full spectral-spatial image of the OX063 and the $^{15}$N-nitroxides will be obtained. The two spectral lines of the $^{15}$N-nitroxides are separated by 2.2 mT. The carbon centered spectral line of the OX063 falls between the nitroxide lines. We will image all three lines simultaneously. Simultaneous imaging of both the oxygen concentrations and the signaling will allow more accurate measurement of an oxygen threshold triggering the signal. To distinguish tumor from normal tissue voxels, a $T_2$ MRI will be obtained after the signaling/oxygen EPR images. This will be registered with the EPR images as has been published and shown in preliminary studies above. {Elas, 2008 #2038; Haney, 2009 #2092}

As indicated in the rationale, the EPR oxygen image will be compared with the hypoxia signal response. Hypoxia signal intensity will be correlated with oxygen partial pressure on both a linear and a log scale to test for threshold behavior in vivo. Images will be continuous wave images with field shifting between the trityl and nitroxide lines. Because the spectral linewidth of the perdeuterated nitroxide—approximately 29 µT—are twice that of the trityl OX063—16 µT we expect that the spatial resolution of the signaling image will be about twice worse than the oxygen image, 2 mm vs. 1 mm. Recognizing this we will apply mutual information analysis {Wells, 1996 #1214; Studholme, 1996 #1215; Studholme, 1997 #1216} to register the images with different resolutions before the oxygen image voxels are averaged and subject to correlation analysis with the signaling.

Anticipated Results. If one assumes that the HIF-1 response, the basis of the hypoxia response, is heterogeneous, then comparison of voxels with high levels of HIF-1 with voxels from a trityl oxygen image should 1) demonstrate a potentially graded response depending on the level of hypoxia or 2) demonstrate an all or nothing response with a distinct oxygen threshold 3) no good correlation between oxygenation level and the HIF-1 response level. If this latter is what is found, other parameters such as pH, thiol level, and temperature may modulate the response. The EPR Center at the University of Chicago is developing the capability to image these parameters as well. If the assumption of a spatially heterogeneous response of HIF1 is incorrect, the homogeneity of the response is interesting in itself.

Potential Limitations and Responses:

The perdeuterated nitroxide (scheme A) is the simplest nitroxide and has shown to be a relatively bioreduction-resistant species. We will develop nitroxide [5] which has been shown to be unusually bioresistant should this be a major concern. If the initial nitroxide dimer concentration is insufficient, this can be increased, as can the dose of the vector.

v. Imaging Hypoxia and VEGF Signaling

Rationale/Basic Method:

This aim is designed to demonstrate the potential extension and generalization of the oxygen biology that these EPR images can provide. VEGF acts in a paracrine mode through cell membrane receptors. {Thurston, 2008 #2090} As noted previously, specific VEGF response elements have been identified in the evolution of Tissue Factor has been defined. {Mechtcheriakova, 1999 #2087} In the manner defined above, a VEGF response element will be constructed. This will be inserted in an adenoviral vector upstream of MMP2 cDNA in a configuration to promote the transcription/translation of MMP2 protein. VEGF signaling will result in the production of active extracellular MMP2 protein. This will then hydrolyse the EPRSM and narrow its EPR line for detection and imaging of the signal. The signal image will be obtained simultaneously with the EPROI.

Brief Methods:

Methods will recapitulate in their entirety the methods for the HRE based vector in this Specific Methods section 4, with the exception that the vector involved with be based on the VRE.

Expected Results:

Since VEGF signaling is thought to be a major consequence of hypoxia signaling, we initially expect that the spatial pattern of in vivo VEGF signaling will mimic the pattern of HIF signaling and inversely correlate with oxygen tension. This is the real strength of these images: they will allow the analysis of the spatial variation and covariation of oxygen, HIF, and VEGF signaling in native conditions. This will be the basis of image-based analysis of other local signals responding to hypoxia.

Potential Limitations and Responses:

The strength of the correlation, however may differ between portions of the tumor. For example, the rim of the tumor may have significantly different signaling intensity than the deeply hypoxic core of the tumor. We will apply image segmentation algorithms available through the Center for EPR Imaging In Vivo Physiology {Haney, 2009 #2092} to separate voxels from non-tumor, tumor-rim and tumor-core voxels. Should we find no co-variation, this will be the basis of investigation of other aspects of the fluid environment that might affect it—pH, redox status, thiol concentrations, and/or local-diffusion coefficients. These environmental characteristics can be interrogated with EPR imaging. We can further investigate other local in vivo signals using the localized, registered biopsy technique that are described above.

High-Isolation Transmit/Receive Surface Coils

One aspect of the present invention provides high-isolation surface coils useful for EPR imaging. In some embodiments, these coils isolate the magnetic fields from the excitation (transmit) signal from the detection (receive) signal. In some embodiments, one or more transmit coils are oriented relative to one or more receive coils in a manner that does not couple the magnetic field generated by the transmit coils to the receive coils (e.g., in some embodiments, oriented such that the coils are all overlapping the subject tissue but orthogonal to one another) in order to maximize a signal-to-noise ratio. The receive coils thus generate an RF electric signal based on spin resonances of the molecules excited by the transmit pulse while minimizing pickup of noise signal (the unwanted transmit signal) from the transmit pulse. The high-isolation surface coils thereby replace the coil(s) and transmit/receive (T/R) switch normally used in pulse-acquisition EPR imaging. For continuous-wave detection, the high-isolation surface coils decouple the detection from phase noise of the exciting power.

The original excite-and-receive system developed by the Bloch group at Stanford when co-discovering the phenomenon of magnetic resonance involved a system which transmitted the RF energy to the spin system which was as completely decoupled from the induced magnetization detection system as possible. Its sensitivity to the exciting RF power was diminished to avoid, as much as possible, confusion of the exciting RF signal from the magnetization induced by the excitation. In the context of EPR, the Denver consortium has developed a Crossed-Loop Resonator (CLR). This is a nested set of cylindrical resonators with orthogonal symmetry axes that produce axial RF B1s which are orthogonal. Similar to the way in which the Bloch design decoupled excitation RF (i.e., the transmitted RF) and the received RF, these designs decouple transmit from receive channels by as much as 60 dB. This reduces the sensitivity of the EPR signal-to-noise of any kind from the RF that excites the electron paramagnetic resonance magnetization without significant loss of that magnetization signal.

In some embodiments of the present invention, the CLR is modified and adapted as a surface coil assembly for small animals. We have made significant progress in this direction with an animal-compatible CLR as shown in FIG. 16A and FIG. 16B.

Figure 16A:
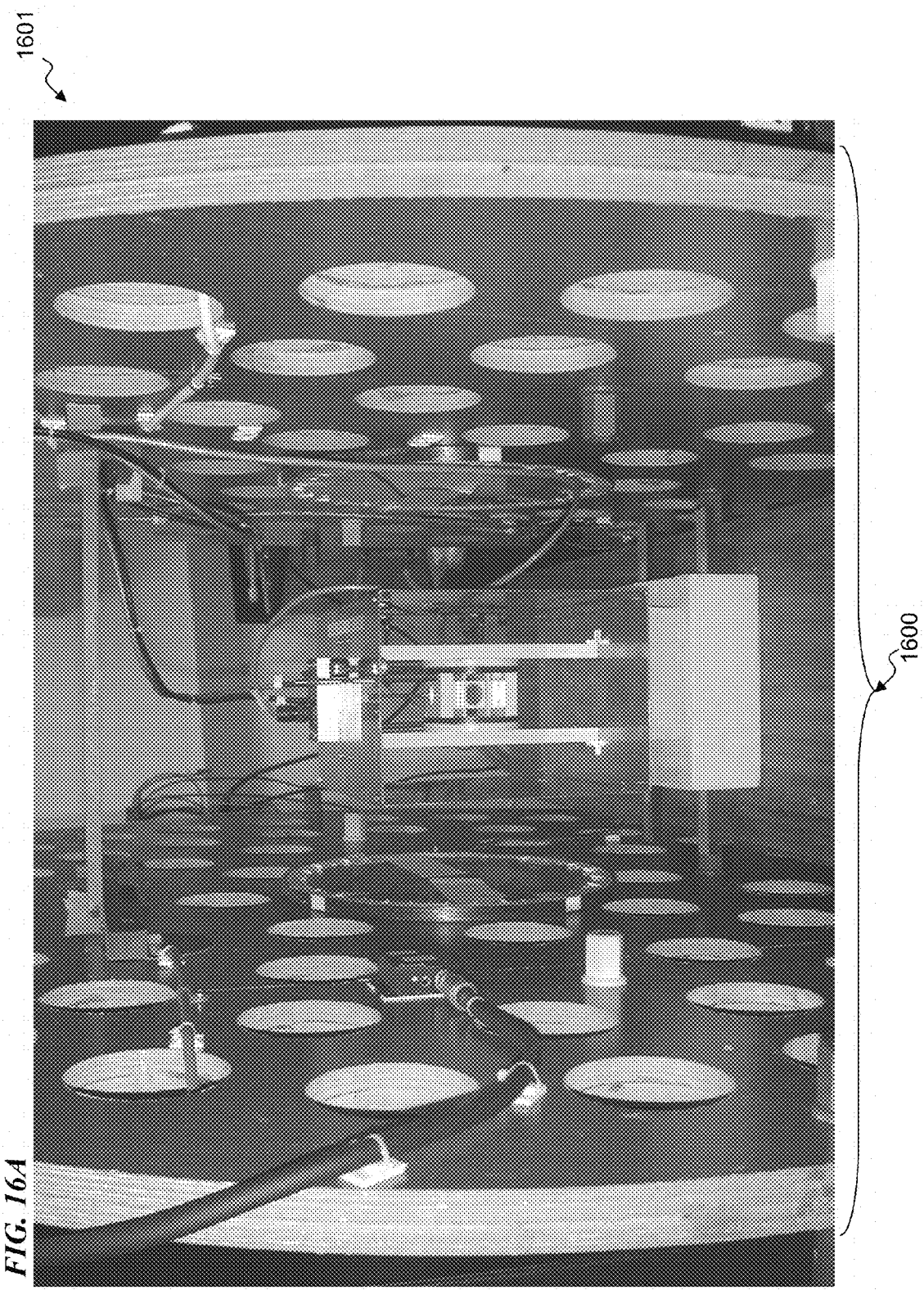
FIG. 16A is a photograph 1601 of an animal-compatible crossed-loop resonator 1600.
Figure 16B:
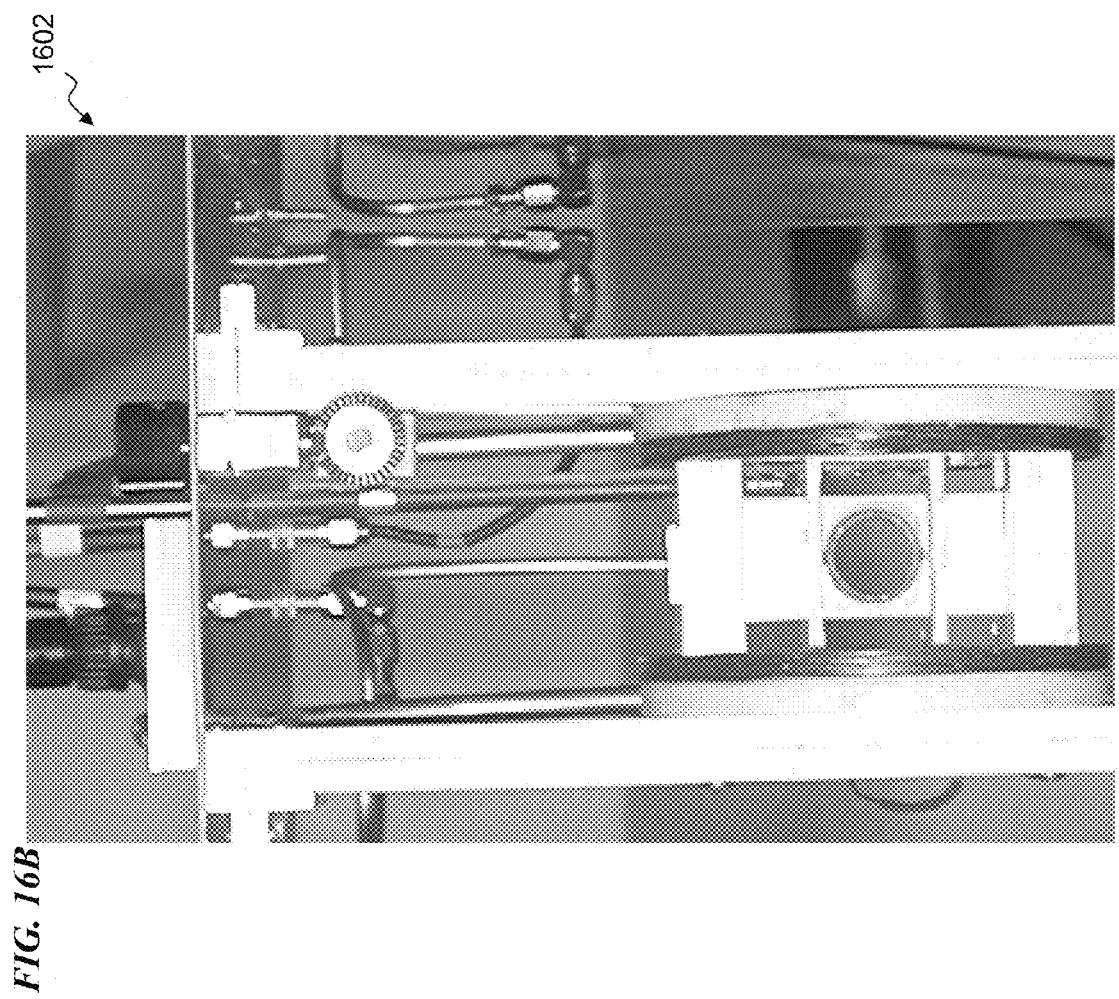
FIG. 16B is a photograph 1602 of the central portion of animal-compatible crossed-loop resonator 1600.

FIG. 16A is a photograph 1601 of an animal-compatible crossed-loop resonator 1600. FIG. 16B is a photograph 1602 of the central portion of animal-compatible crossed-loop resonator 1600. This crossed-loop resonator is suitable when the entire subject is very small (e.g., mouse-sized animals) such that it fits within the coil and such that a relatively low-power RF signal will penetrate deep enough in the volume being imaged via EPRI without causing tissue damage (such damage is usually the result of RF heating).

However, for the EPRI of the present invention to be applied to human subjects, some embodiments use surface coils or surface-volume coils for smaller volumes of tissue (e.g., volumes less than the entire animal) since resonators that completely contain the human subject or even a human limb or head are too large for convenient widespread use, and the power requirements scale as the volume of the resonator. Specific absorption rates (SAR) and RF heating of the tissue increase with resonator volume and rapidly exceed human health limits (i.e., the power of the transmitted excitation signal causes excessive heat absorption leading to tissue damage and/or excessive discomfort).

Many if not most of major human cancers are either superficial or are accessible through an orifice of the patient with minimal invasiveness. Therefore most human cancers can be accessed with a surface coil of the present invention with relatively limited depth sensitivity and relatively limited sensitive volume. Breast cancers, head and neck cancer are directly accessed with surface coils. Prostate cancer, cancer of the uterine cervix, half of colon cancers (rectal cancer), anal cancer and esophageal cancers are accessible to a surface coil of the present invention positioned through an orifice (e.g., via an endoscope or similar instrument).

The use of surface coils reduces power requirements by limiting the volume radiated. Limited regions of anatomy have less strict SAR limits (and heating limits) for human application. In some embodiments, the present invention provides apparatus for the surface coils, the drive and receive circuitry, control of the system, as well as image generation and display, as well as a computer-readable medium having instructions stored thereon for causing a computer to execute the method of signal processing and image generation. In some embodiments, the present invention provides a method for designing surface coils, as well as a computer-readable medium having instructions stored thereon for causing a computer to execute the method of designing coils.

Preliminary Data:

In some embodiments, the present invention provides surface coils that are constructed from two separate sets of conductors, the transmit and the receiver conductors, and oriented such that the conducting elements are substantially orthogonal. In some embodiments, the conducting elements are not necessarily orthogonal, but they are configured such that the magnetic field generated by the transmit conducting elements is orthogonal to the magnetic field detected or received by the receive conducting elements. The present invention combines the advantages of surface coils and crossed-loop resonators and can be used for EPR measurements and/or imaging. A simple conductor configuration including return current conductors has been modeled.

Figure 17A:
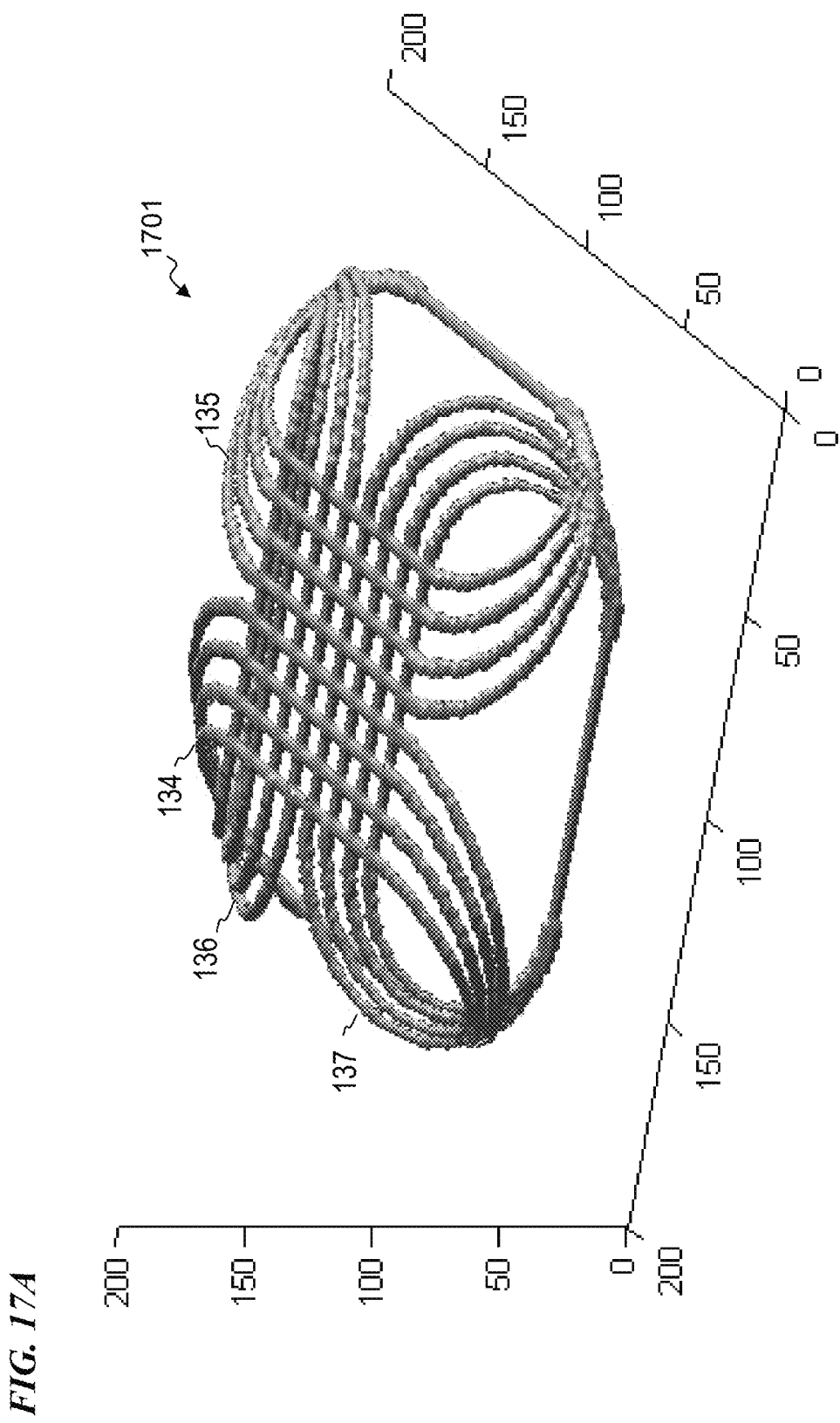
FIG. 17A is a schematic perspective drawing of a design of a transmit-receive isolation (TX-RX isolation) surface-volume coil resonator 1701, according to some embodiments of the present invention.

An example of a set of current-path configurations is shown in FIG. 17A. Its configuration focuses B1 away from the surface shown through the return paths. This configuration is appropriate for imaging or other measurement of a human breast cancer, a human cervical (neck) lymph node or a laryngeal cancer. It could possibly also be used for testicular or prostate cancer.

FIG. 17A is a conceptual schematic perspective drawing of a design of the crossed wire resonator 1701, according to some embodiments of the present invention. One or more (four are shown here) elongated (e.g., racetrack-shaped) RF transmit rungs (also called TX loops) 134 to the left of a center point are angled downward and toward the right, and one or more (four are shown here) elongated RF transmit rungs (TX loops) 135 to the right of the center point are angled downward and toward the left. The TX loop(s) 134 on the left are driven with an RF signal that is 180 degrees out of phase with the RF signal driving the TX loop(s) 135 on the right (i.e., at a point in time when current of the RF transmit pulse is traveling clockwise in the left TX loop(s), a corresponding current is traveling counterclockwise in the right-hand TX loop(s) as viewed from the top).

Similarly, one or more (four are shown here) elongated RF receive rungs (also called RX loops) 136 to the far side of the center point are angled downward and toward the front, and one or more (four are shown here) elongated RF transmit rungs (RX loops) 137 to the near side of the center point are angled downward and toward the back. The RX loop(s) 137 on the near side are connected to RF signal preamplifier(s) that are 180 degrees out of phase with the signal preamplifier(s) that are obtaining their input signal from the RX loop(s) 136 on the far side (i.e., at a point in time when current of the received RF signal is traveling clockwise in the far-side RX loop(s) 136, a corresponding current of the received RF signal is traveling counterclockwise in the near-side RX loop(s) 137 as viewed from the top).

In some embodiments, the TX loops 134 and 135 are tuned to the desired transmit frequency (e.g., in some embodiments, about 250 MHz based on a Larmor frequency for electrons in the given DC magnetic field generated by the constant and gradient coils) and the TX loops are spaced relatively from one another to obtain a relatively uniform horizontal transmitted RF field in the X direction in the tissue under the TX coils (in some embodiments, each TX coil 134 and 135 is angled to point towards a center volume within the tissue), while the RX loops 136 and 137 are tuned to the desired receive frequency (e.g., in some embodiments, about the same 250 MHz based on the Larmor frequency used for the transmit pulses) and the RX loops are spaced relatively from one another and relative to the TX loops 134 and 135 to receive a relatively uniform signal strength from a horizontal RF field in the Y direction in the tissue under the TX coils (in some embodiments, each RX coil 136 and 137 angled to point towards the center volume within the tissue). In some embodiments, an RF simulation software package (such as SEMCAD X uWave, available from SPEAG (Schmid and Partner Engineering AG) is used to empirically and iteratively improve the uniformity of the transmit and receive fields while optimizing the field isolation between the RX coils and TX coils.

FIG. 17B is a schematic plan drawing of an isolated surface-coil resonator 1702, according to some embodiments of the present invention. FIG. 17C is a schematic side-elevation drawing of isolated surface-coil resonator 1702. FIG. 17D is a schematic front-elevation drawing of isolated surface-coil resonator 1702.

In some embodiments, coil 1702 includes a single left-side transmit loop 134 driven at its left side by RF pulses (at a relative phase of zero degrees) generated by pulse drive circuit 151, and a single right-side transmit loop 135 driven at its right side by RF pulses (at a relative phase of 180 degrees) generated by pulse drive circuit 151, such that the current 133 in the center portion of each loop is in the same direction (at the moment in time represented here, current 133 is clockwise in loop 134 and counterclockwise in loop 135). In some embodiments, coil 1702 also includes a single top-side receive loop 136 that outputs RF signal at its top side (at a relative phase of zero degrees) into preamp circuit 152, and a single lower-side receive loop 135 that outputs RF signal at its bottom side (at a relative phase of 180 degrees) into preamp circuit 152, such that the received current in the center portion of each loop due to a given spin echo signal (e.g., from a reporter molecule in tissue 99 of a patient) is in the same direction, and the resulting electrical signal is combined by preamps that combine the signals 180 degrees out of phase with one another. In some embodiments, the patient is positioned prone (face down) such that the tissue being imaged hangs down into a depression in the RX-TX coil form 199 (upside down relative to the view shown in FIG. 17D). RF field 131 is an RF field (the arrow direction on dashed line 131 indicating the direction of the magnetic field generated by a current in the direction indicated by the arrows indicated by reference 133 (of course, since the transmitted RF field is caused by alternating current, the arrow head of dashed arrow 131 indicates the polarity of the field at a single moment in time, and at a later time that is one-half cycle of the RF frequency later, the polarity is reversed)) passes through the tissue volume being examined, while the return RF field 132 (see FIG. 17C and FIG. 17D) passes outside the tissue volume.

In some other embodiments (as indicated in FIG. 17A), a plurality of transmit loops 134 are provided to the left side and a plurality of transmit loops 135 are provided to the right side; and a plurality of receive loops 136 are provided to the near side and a plurality of receive loops 135 are provided to the far side.

In some embodiments, biopsy operations are performed in real time while the patient is in the EPRI machine, using non-magnetic needles (e.g., such as the titanium-tipped #11 breast biopsy needle (C. R. Bard, Tempe, Ariz.) described above, administered with vacuum suction. In some embodiments, the biopsy needle is held in a positioning device that is registered with the imaging portion of the machine, in order that the physician can direct the needle to the desired position using the images presented from the EPRI. In some such embodiments, the display is provided in 3D (using such techniques as switching-frame, red-green, polarization or other well known 3D techniques, and the physician is provided with suitable viewing glasses or other viewing means) and the position of the needle relative to the tissue is displayed for the physician to be able to guide the needle using the displayed EPRI and needle-position displayed output.

In some embodiments, this particular configuration produces an isolation of the excite power from the detection elements of 60 dB. The estimate is produced using a Biot-Savart magnetic-field calculation comparing the integrated magnitude of the dot product of the magnetic fields produced by each coil with the magnitude of the magnetic field produced by either current set. The square of that ratio is the power isolation of one from the other.

Hyde argues that in fact, it is the sum of the dot products to the magnetic field that is the crucial variable, not the sum or integral of the magnitude of the dot products so that this may be an underestimate of the isolation. On the other hand these estimates were obtained using an idealized filamentary approximation to the actual situation. A realistic set of current paths will likely not have the isolation of the idealized currents. Again, in some embodiments, a software simulation such as SEMCAD X is used to iteratively change the geometry of the coils to optimize TX-RX isolation.

FIG. 17B1 is a schematic plan-view diagram of just the transmit portion 1702TX of TX-RX isolation coil system 1702 of FIG. 17B according to one embodiment of the present invention. FIG. 17C1 is a schematic side-elevation-view diagram of transmit portion 1702TX of TX-RX isolation coil system 1702 (a view that is orthogonal to that of FIG. 17B1) according to one embodiment of the present invention. FIG. 17D1 is a schematic front-elevation-view diagram of transmit portion 1702TX of TX-RX isolation coil system 1702 (a view that is orthogonal to that of FIG. 17B1 and FIG. 17C1) according to one embodiment of the present invention. These views showing only the transmit portions are presented here separately for clarity, but would be implemented with the receive portions as shown in FIG. 17B, FIG. 17C, and FIG. 17D.

FIG. 17B2 is a schematic plan-view diagram of only the receive portion 1702RX of TX-RX isolation coil system 1702 according to one embodiment of the present invention. FIG. 17C2 is a schematic side-elevation-view diagram of only the receive portion 1702RX of TX-RX isolation coil system 1702 (a view that is orthogonal to that of FIG. 17B2) according to one embodiment of the present invention. FIG. 17D2 is a schematic front-elevation-view diagram of only the receive portion 1702RX of TX-RX isolation coil system 1702 (a view that is orthogonal to that of FIG. 17B2 and FIG. 17C2) according to one embodiment of the present invention. These views showing only the receive portions are presented here separately for clarity, but would be implemented along with the transmit portions as shown in FIG. 17B, FIG. 17C, and FIG. 17D. Dashed arrow 139 indicates generally a direction of the center of the sensed RF field (of course, since the sensed RF field causes alternating current, the arrow head of dashed arrow 139 indicates the polarity of the field at a single moment in time, and at a later time that is one-half cycle of the RF frequency later, the polarity is reversed).

FIG. 17B3 is a schematic plan drawing of a butterfly-type TX-RX isolation coil system 1703, according to some embodiments of the present invention. In some embodiments, the electrical current in the two half-butterfly portions (loop portion 134 and loop portion 135) of FIG. 17B3 travel in the same directions 133 as shown in FIG. 17B, but rather than driving both loops separately a single drive point to the left side is provided, and the current crosses over from one loop half to the other in the middle. In some embodiments, other aspects are as described above for FIG. 17B. FIG. 17C3 is a schematic side-elevation drawing of butterfly-type TX-RX isolation coil system 1703. FIG. 17D3 is a schematic front-elevation drawing of butterfly-type TX-RX isolation coil system 1703.

FIG. 17B4 is a schematic plan-view diagram of only the transmit portion 1703TX of butterfly-type TX-RX isolation coil system 1703 according to one embodiment of the present invention. FIG. 17C4 is a schematic side-elevation-view diagram of only the transmit portion 1703TX of butterfly-type TX-RX isolation coil system 1703 (a view that is orthogonal to that of FIG. 17B4) according to one embodiment of the present invention. FIG. 17D4 is a schematic front-elevation-view diagram of only the transmit portion 1703TX of butterfly-type TX-RX isolation coil system 1703 (a view that is orthogonal to that of FIG. 17B4 and FIG. 17C4) according to one embodiment of the present invention. These views showing only the transmit portions are presented here separately for clarity, but would be implemented with the receive portions as shown in FIG. 17B3, FIG. 17C3, and FIG. 17D3.

FIG. 17B5 is a schematic plan-view diagram of only the receive portion 1703RX of butterfly-type TX-RX isolation coil system 1703 according to one embodiment of the present invention. FIG. 17C5 is a schematic side-elevation-view diagram of only the receive portion 1703RX of butterfly-type TX-RX isolation coil system 1703 (a view that is orthogonal to that of FIG. 17B5) according to one embodiment of the present invention. FIG. 17D5 is a schematic front-elevation-view diagram of only the receive portion 1703RX of butterfly-type TX-RX isolation coil system 1703 (a view that is orthogonal to that of FIG. 17B5 and FIG. 17C5) according to one embodiment of the present invention. These views showing only the receive portions are presented here separately for clarity, but would be implemented along with the transmit portions as shown in FIG. 17B3, FIG. 17C3, and FIG. 17D3.

Figure 18A:
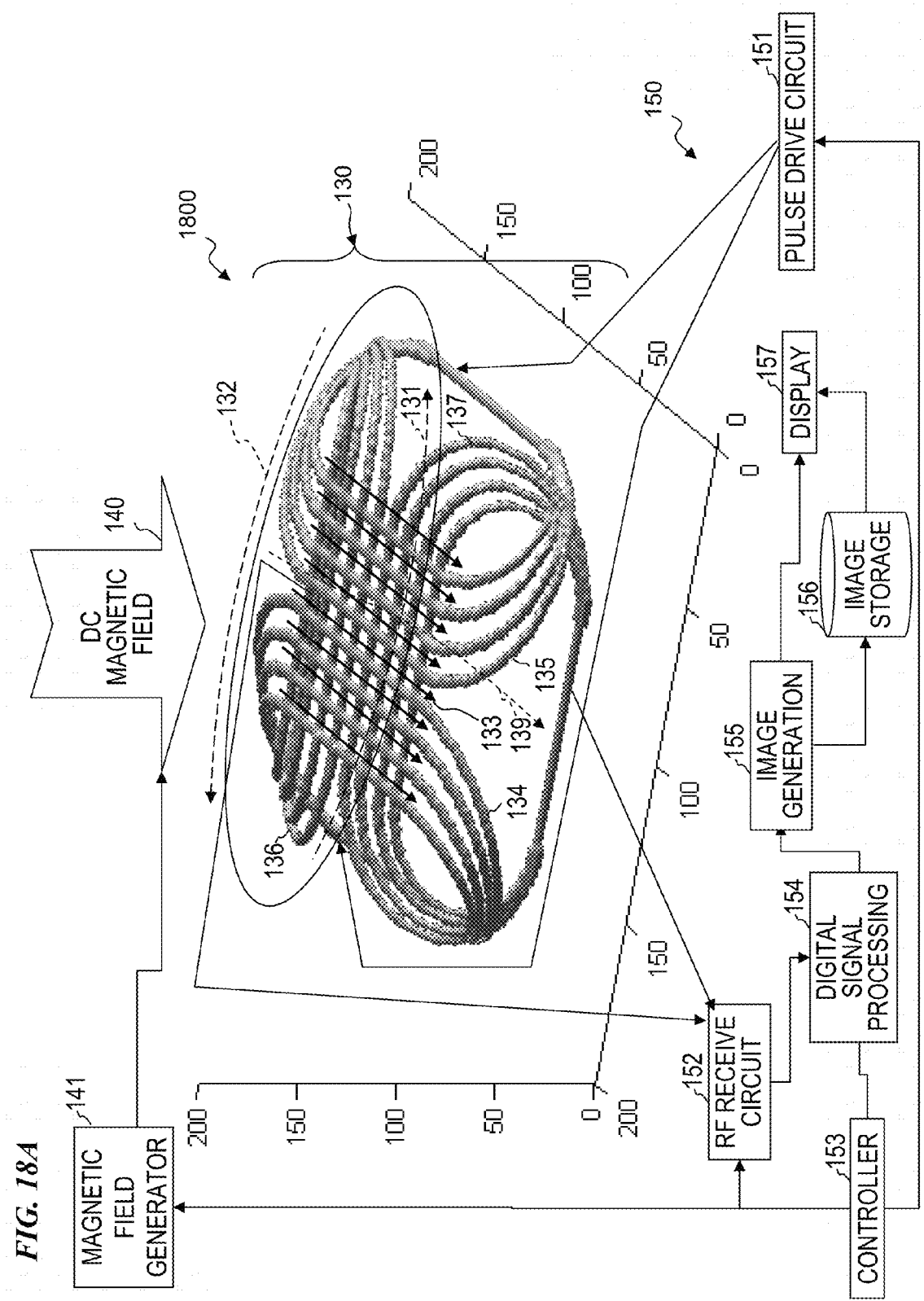
FIG. 18A is a schematic perspective diagram of a system 1800 according to one embodiment of the present invention.

FIG. 18A is a schematic perspective-view and block diagram of a system 1800 according to one embodiment of the present invention. In some embodiments, system 1800 includes a controller 153 that coordinates, times, and controls the operation of system 1800, including the generation, of a magnetic field 140 that is substantially fixed (e.g., generated by a direct-current (DC) electromagnet or other suitable magnetic-field generator 141 such as a movable set of permanent magnets such as high-field rare-earth magnets) for any one set of measurements (image acquisition), but that can be varied to be oriented in one or a plurality of different directions and/or geometry for each one of a series of sets of measurements (or image acquisition), which are then used to reconstruct a three-dimensional (3D) image (or one or more in a series of two-dimensional (2D) image slices) of the structure and/or chemical activity and/or biological activity of one or more proteins or other markers in a portion of tissue (such as a breast) of a patient 99, wherein coils 134, 135, 136, and 137 (which together form transmit-receive coil unit 130, which is connected to electronics and/or computer system 150) are arranged on a concave surface (e.g., in some embodiments, of a thin substrate of a rigid or semi-rigid material that, in some embodiments, includes fluorine-based polymer such as Teflon® or the like, and/or glass or ceramic or the like, that has little or no material having hydrogen atoms that would generate signal that interferes or hides the signal from the tissue of patient 99) that is placed against the tissue of patient 99 (see, e.g., FIG. 18D1). In some embodiments, the tissue of interest is convex (e.g., breast tissue, as shown in FIG. 18C1 and FIG. 18D1 described below) that conforms to (or that is forced to conform to by being compressed by) the concave surface of the coil substrate 199 (see FIG. 18B, FIG. 18D1 and FIG. 18C2 for a diagram of one embodiment of coil substrate 199). In some embodiments, each of the transmit coils 134, 135 has a characteristic impedance (e.g., in some embodiments, this characteristic impedance is 50 ohms) and the transmit coils are driven by a high-power pulse (e.g., in some embodiments, 1 KW to 5 KW pulse (e.g., a current of 20 amps to 100 amps into the characteristic impedance of 50 ohms) that is relatively short (e.g., a pulse duration of between 1 nanosecond and about 1 millisecond, in various embodiments). When there is no pulse of electric current applied to the transmit coil, the applied DC magnetic field 140 causes an alignment of the spins of the electrons in the portion of tissue of patient 99. Then, when an electric pulse is applied to the transmit coils 134 and 135, the resulting excitation magnetic pulse causes the direction of spins of the electrons to precess. The receive coils 136 and 137 are oriented (e.g., in some embodiments, perpendicular) relative to the transmit coils such that the excitation magnetic pulse causes little or none of its signal to be detected by the receive coils 136 and 137, in order that the precession signal from the electron spins (e.g., a low-level signal having frequency components in a general range of 100 to 1000 megahertz (MHz), and in particular having frequency components in a range near 250 MHz (such as described in the attached papers of Appendix A of U.S. Provisional Patent Application 61/306,917 titled "HIGH-ISOLATION TRANSMIT/RECEIVE SURFACE COILS AND METHOD FOR EPRI" filed Feb. 22, 2010 by Howard J. Halpern, which is incorporated herein by reference (the Appendix A is titled "A Versatile High Speed 250-MHz Pulse Imager for Biomedical Applications" by Epel, et al., Concepts Magn. Reson. Part B (Magn. Reson. Engineering) 33B: 163-176, 2008), and Appendix B (titled "Imaging radio frequency electron-spin-resonance spectrometer with high resolution and sensitivity for in vivo measurements" by Halpern et al., Rev. Sci. Instrum. 60(6), June 1989). In some embodiments, the DC magnetic field 140 can be changed to one of a plurality of different directional orientations and/or spatial patterns (also called gradients). The spectral components of the received signal from receive coils 136 and 137 can then be processed (based on the spatial and strength parameters of the applied DC magnetic field 140 for each of one or more pulses applied using the transmit coils 134 and 135) to assemble an image (in much the same way as is used to assemble an image using well-known conventional MRI techniques. Thus, in some embodiments, controller 153 controls the magnetic-field generator 141 to generate a DC magnetic field 140 for a given measurement, then controls pulse-drive circuit to apply a pulse of electrical current to transmit coils 134 and 135. RF receive circuit 152 receives the sensed RF signal from receive coils 136 and 137 and generates an amplified received signal having phase, amplitude and frequency information. In some embodiments, controller 153 controls the operation of digital signal processing unit 154 to process the received signal (e.g., in some embodiments, unit 154 performs Fourier transforming of digitized and/or saved time domain signals to obtain frequency information; and, using information from a plurality of different gradient directions, performs filtered back-projection inverse Radon transforming of the frequency information obtained from the Fourier transforming of the time domain signals to obtain spatial information (e.g., spatial EPR signal strength for each of a plurality of voxels in a three-dimensional configuration)) and output data that is delivered to image-generation unit 155 (e.g., in some embodiments, a combination of hardware and software processing) and/or to data storage unit 156. In some embodiments, image-generation unit 155 uses data from digital signal processing unit 154 and/or from data storage unit 156 and processes that data to form image data that is then stored to data storage unit 156 and/or displayed on display unit 157.

In some embodiments, transmit-receive coil unit 130 is relatively small (e.g., in some embodiments, 1 cm by 1 cm by 0.5 cm high, or in other embodiments, 2 cm by 2 cm by 0.5 cm high, 3 cm by 3 cm by 0.5 cm high, or other suitable size) in order to obtain a sufficient signal without undue heating of the tissue portion of patient 99 that is being imaged and/or measured. Such sizes are suitable for small volumes of tissue such as the prostate, testicle, or small portions of breast tissue. In other embodiments, larger sizes (such as 10 cm by 10 cm by 5 cm high or larger) are used for tissue such as the chin, forehead or breast. In some such embodiments, the patient is positioned prone, and the tissue to be examined is positioned to be hanging downward into and/or against the set of coils that is pointed in a generally upward direction. In other embodiments, the transmit-receive coil unit 130 is made of a size useful for the tissue to be examined (e.g., in some embodiments, 1 cm by 1 cm by 0.5 cm high, or in other embodiments, 2 cm by 2 cm by 1 cm high, 3 cm by 3 cm by 1.5 cm high, 4 cm by 4 cm by 2 cm high, 5 cm by 5 cm by 2.5 cm high, 6 cm by 6 cm by 3 cm high, 7 cm by 7 cm by 3.5 cm high, 8 cm by 8 cm by 4 cm high, or 9 cm by 9 cm by 4.5 cm high). In some embodiments, the width of the transmit coils is different than the perpendicular length of the receive coils.

FIG. 18B is a schematic plan-view diagram of transmit-receive system 1801 according to one embodiment of the present invention. This plan view shows both the transmit coils 134 and 135 and the pulse drive circuit 151 (these transmit elements are shown alone in FIG. 18B1) as well as the receive coils 136 and 137 and the receive circuit 152 that amplifies the sensed signal detected by the receive coils from the magnetic field of the electron spin precession (these receive elements are shown alone in FIG. 18B2).

FIG. 18C is a schematic elevation-view diagram of transmit-receive system 1801 (a view that is orthogonal to that of FIG. 18B) according to one embodiment of the present invention. This elevation-view diagram shows both the transmit coils 134 and 135 and the pulse drive circuit 151 (these transmit elements are shown alone in FIG. 18C1) as well as the receive coils 136 and 137 and the receive circuit 152 that amplifies the sensed signal detected by the receive coils from the magnetic field of the electron spin precession (these receive elements are shown alone in FIG. 18C2).

FIG. 18D is a schematic elevation-view diagram of transmit-receive system 1801 (a view that is orthogonal to that of FIG. 18B and FIG. 18C) according to one embodiment of the present invention. This elevation-view diagram shows both the transmit coils 134 and 135 and the pulse drive circuit 151 (these transmit elements are shown alone in FIG. 18D1) as well as the receive coils 136 and 137 and the receive circuit 152 that amplifies the sensed signal detected by the receive coils from the magnetic field of the electron spin precession (these receive elements are shown alone in FIG. 18D2).

FIG. 18B1 is a schematic plan-view diagram of transmit portion 1802 of transmit-receive system 1801 according to one embodiment of the present invention. This view shows the outline of the outer edge of a dielectric shell 199 that supports both the transmit coils 134 and 135, as well as the receive coils 136 and 137. Section line 18D1-18D1 in this figure shows the position of the cross-section view shown in FIG. 18D1. In some embodiments, a positive electrical current pulse in the direction 133 is applied to two or more conductor loops (e.g., to conductor loop 134.1 and conductor loop 135.1) or to four or more loops (to a quad of conductors such as e.g., to conductor loop 134.1 and conductor loop 135.1 and conductor loop 134.5 and conductor loop 135.5), or to all loops 134.1-134.5 and 135.1-135.5. In some embodiments, the pulse drive circuit 151 is configured to selectively drive a subset of the conductor loops based on control signals from controller 153.

FIG. 18C1 is a schematic elevation-view diagram of transmit portion 1802 of transmit-receive system 1801 (a view that is orthogonal to that of FIG. 18B1) according to one embodiment of the present invention. This view also shows the cross section (at section line 18D1-18D1 in FIG. 18B1) of the portion of tissue of patient 99 that that is being imaged and/or otherwise measured.

FIG. 18D1 is a schematic elevation-view diagram of transmit portion 1802 of transmit-receive system 1801 (a view that is orthogonal to that of FIG. 18B1 and FIG. 18C1) according to one embodiment of the present invention. This view shows the cross section (at section line 18D1-18D1 in FIG. 18B1) of the dielectric shell 199 that supports both the transmit coils 134 and 135, as well as the receive coils 136 and 137. This view also shows the cross section (at section line 18D1-18D1 in FIG. 18B1) of the portion of tissue of patient 99 that that is being imaged and/or otherwise measured.

FIG. 18B2 is a schematic plan-view diagram of receive portion 1803 of transmit-receive system 1801 according to one embodiment of the present invention. This view shows the outline of the outer edge of a dielectric shell 199 that supports both the transmit coils 134 and 135, as well as the receive coils 136 and 137. Section line 18C2-18C2 in this figure shows the position of the cross-section view shown in FIG. 18C2. In some embodiments, the received signal from two or more conductor loops (e.g., to conductor loop 136.1 and conductor loop 137.1) or to four or more loops (from a quad of conductors such as e.g., to conductor loop 136.1 and conductor loop 137.1 and conductor loop 136.5 and conductor loop 137.5), or to all loops 136.1-136.5 and 137.1-137.5 are each separately received and processed in order to retain phase information of the detected fields. In some embodiments, the receive circuit 151 is configured to selectively receive signal separately from each one of a subset of the conductor loops 136 and 137 based on control signals from controller 153.

FIG. 18C2 is a schematic elevation-view diagram of receive portion 1803 of transmit-receive system 1801 (a view that is orthogonal to that of FIG. 18B2) according to one embodiment of the present invention. This view shows the cross section (at section line 18C2-18C2 in FIG. 18B2) of the dielectric shell 199 that supports both the transmit coils 134 and 135, as well as the receive coils 136 and 137. This view also shows the cross section (at section line 18C2-18C2 in FIG. 18B2) of the portion of tissue of patient 99 that that is being imaged and/or otherwise measured.

FIG. 18D2 is a schematic elevation-view diagram of receive portion 1803 of transmit-receive system 1801 (a view that is orthogonal to that of FIG. 18B2 and FIG. 18C2) according to one embodiment of the present invention. This view also shows the cross section (at section line 18C2-18C2 in FIG. 18B2) of the portion of tissue of patient 99 that that is being imaged and/or otherwise measured.

Figure 18E:
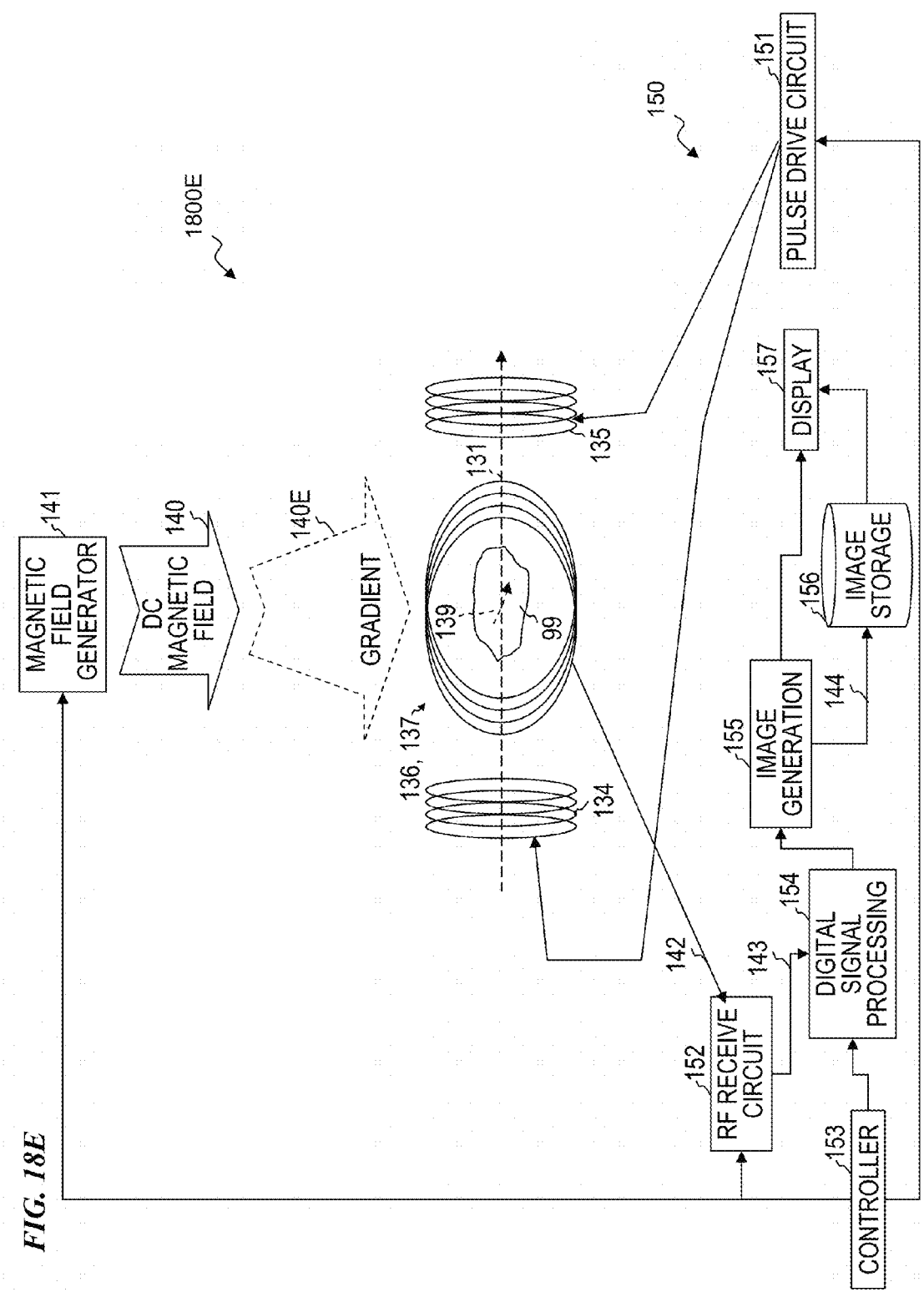
FIG. 18E is a schematic elevation-view diagram of a system 1800E with a background magnetic field 140 and its gradient 140E both in a vertical direction according to one embodiment of the present invention.

FIG. 18E is a schematic elevation-view block diagram of a system 1800 (shown as configuration 1800E with a background magnetic field 140E in a vertical direction) according to one embodiment of the present invention. In some embodiments it is preferred to have the background static magnetic field 140 in a direction that is maximally orthogonal to the bulk of the transmit field 131 and the bulk of the receive field 139 (which is directed out of the drawing sheet in a direction orthogonal. Thus the static field direction in FIG. 18E is vertical, while the direction of the gradient of that field (e.g., gradient directions 140E of FIG. 18E, gradient directions 140F of FIG. 18F, and gradient directions 140G of FIG. 18G) is varied to one of a plurality of different directions for FIG. 18E, FIG. 18F, and FIG. 18G. However, when the device is acquiring signal toward the edges of the transmit field or the receive field of surface-volume coils (where those fields are curved) such as shown in FIGS. 17B-17D5 and FIGS. 18B-18D, those fields curve upward at the edges and it is advantageous to tilt not only the gradient but also the direction of the background magnetic field 140, in order to have the static field direction orthogonal to the transmit RF field (i.e., the RF field generated by coils 134 and 135) and the receive RF signal (the signal received by coils 136 and 137).

Figure 18F:
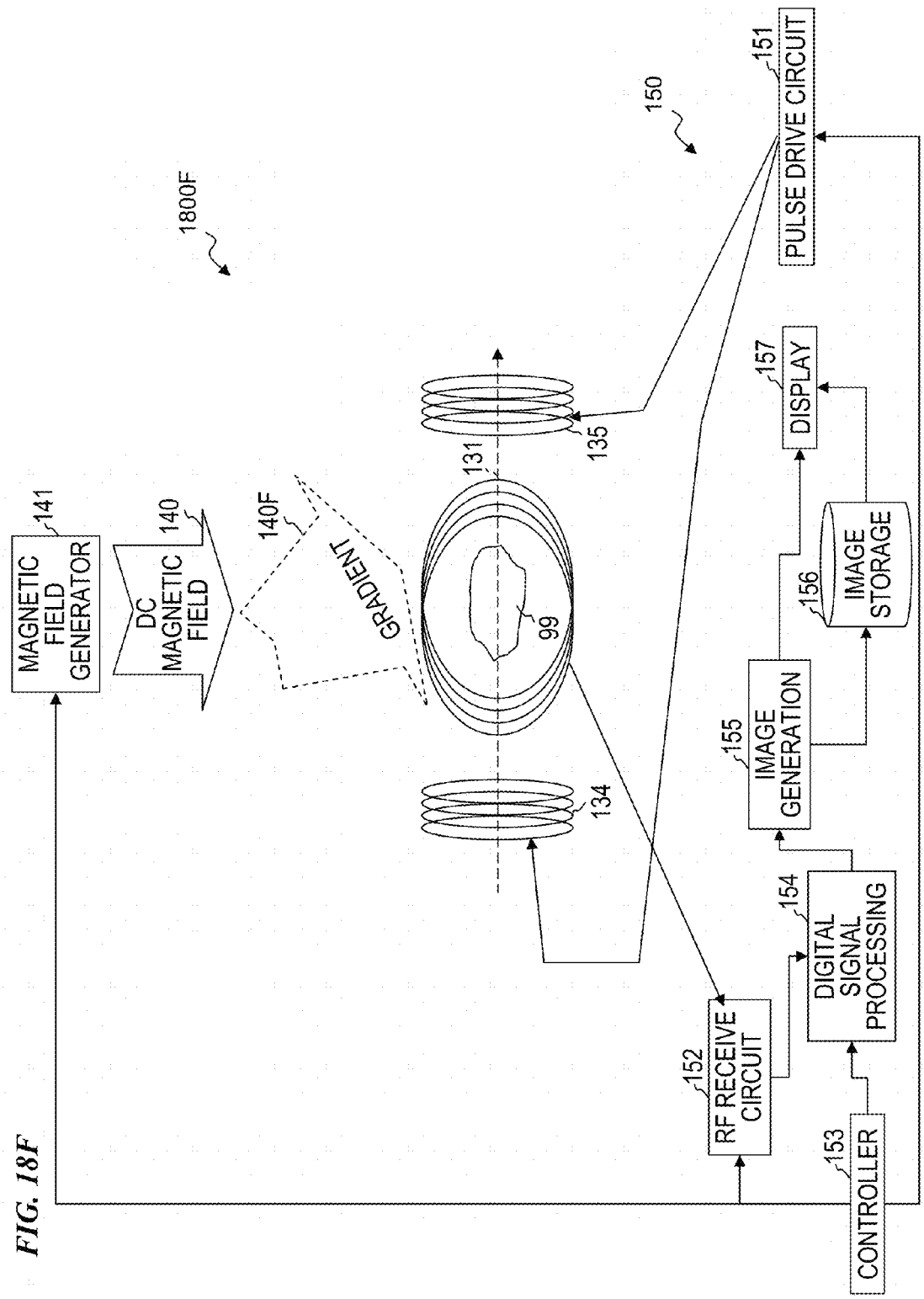
FIG. 18F is a schematic elevation-view diagram of a system 1800F with a background magnetic field 140 in a vertical direction and its gradient 140F angled from the left-hand side of a vertical direction according to one embodiment of the present invention.

FIG. 18F is a schematic elevation-view diagram of a system 1800 (shown as configuration 1800F with a background magnetic field angled from the left-hand side of a vertical direction) according to one embodiment of the present invention.

Figure 18G:
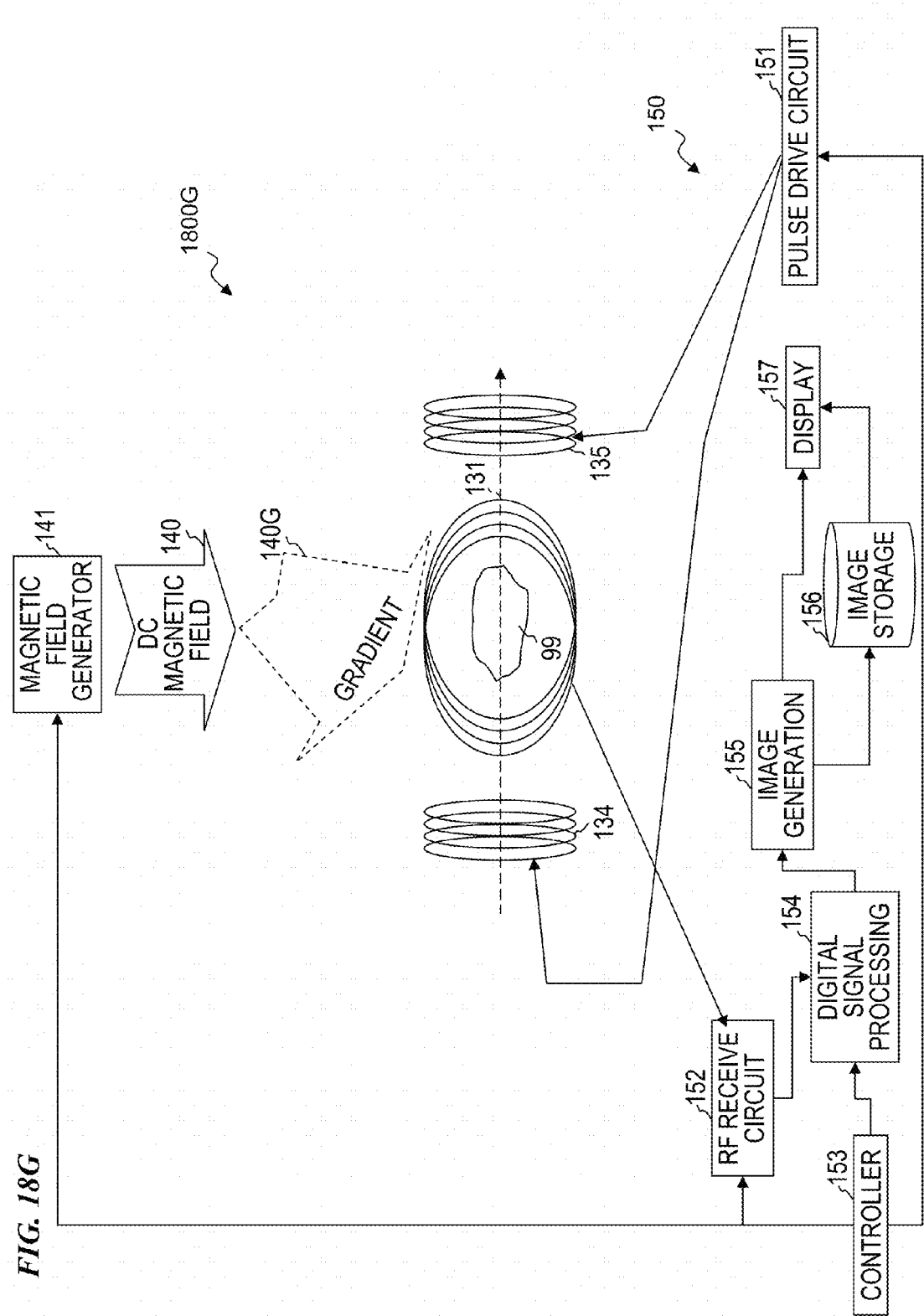
FIG. 18G is a schematic elevation-view diagram of a system 1800G with a background magnetic field 140 in a vertical direction and its gradient 140G angled from the right-hand side of a vertical direction according to one embodiment of the present invention.

FIG. 18G is a schematic elevation-view diagram of a system 1800 (shown as configuration 1800G with a background magnetic field angled from the right-hand side of a vertical direction) according to one embodiment of the present invention.

Figure 18H:
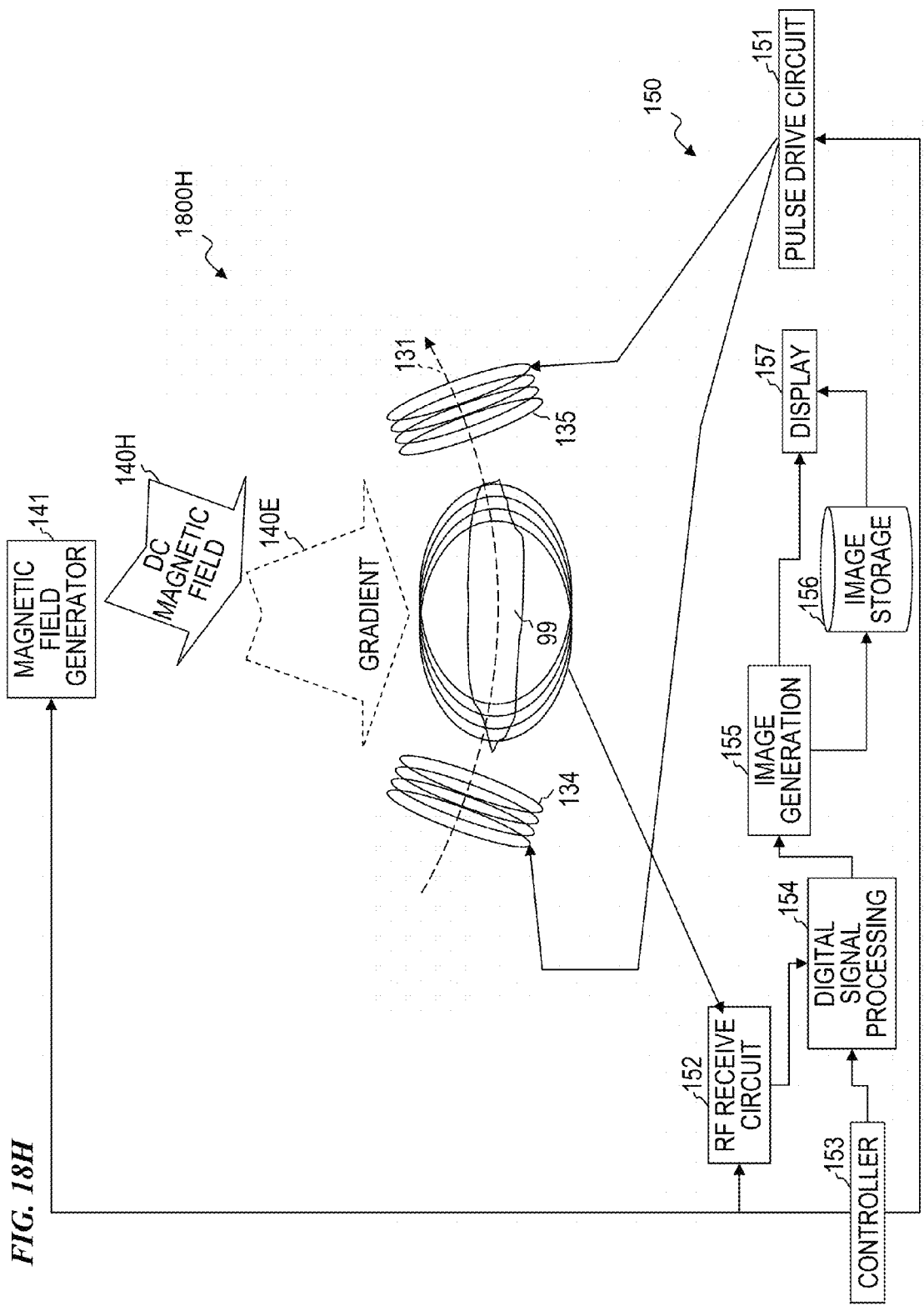
FIG. 18H is a schematic elevation-view diagram of a system 1800H with a background magnetic field 140 and its gradient 140H both angled from the right-hand side of a vertical direction according to one embodiment of the present invention.

FIG. 18H is a schematic elevation-view diagram of a system 1800 (shown as configuration 1800H with a background magnetic field 140 and its gradient 140H both angled from the right-hand side of a vertical direction according to one embodiment of the present invention. Although in some embodiments it is preferred to have the background magnetic field 140 in a single direction that is maximally orthogonal to the bulk of the transmit field 131 and the bulk of the receive field 139, with surface coils or surface-volume coils of the present invention, that is not always possible. FIG. 18H shows a configuration in which the direction of the background magnetic field 140 is tilted. Such a configuration of field direction is used with a plurality of difference gradient directions (e.g., 140E, 140F, . . . 140G, where gradient direction 140E is shown here in FIG. 18H) to obtain improved SNR at the edges of the volume of tissue being imaged. In a conventional nuclear MRI imager, the field strengths are typically 1.5 T to 3 T or even higher and it is very difficult to quickly change the field direction, and even changing the gradient direction is the cause of much of the undesirable noise in such machines. As noted above, because the magnetic moment of the electron is 658 times that of the water proton, the strength of the static magnetic fields are $\frac{1}{658}$ times lower allowing low-field inexpensive magnet systems ~90 gauss, (i.e., 9 milliTesla (mT)) at an operating frequency of 250 MHz. {Halpern, 1989 #89; Halpern, 1991 #899} This allows some embodiments to use a magnetic-field generator 141 that changes the direction of the static magnetic field 140 to a plurality of different directions (e.g., field direction 140 of FIG. 18E versus field direction 140H of FIG. 18H). Further still, in some embodiments, the direction of the static magnetic field 140 within the volume 99 being imaged has a direction that is curved, such that the direction of the static magnetic field 140, the direction of the transmitted RF signal 131 and the direction of the received RF signal 139 are much more orthogonal to one another over a larger volume than if the direction of the static magnetic field 140 were kept to be only in the Z direction (up-down in FIG. 18H).

In some embodiments, the present invention includes a design phase using the MAFIA (Maxwell equations solved with Finite Interval Analysis) 4 software. This software allows modeling small parts and finite wire diameters that are part of the realistic design.

In some embodiments, the present invention then includes a construction phase, in which various versions of individual elements and groups of elements are constructed. In some embodiments, a plurality of surface coil elements are ganged together. In FIG. 2, the indicated grouping of the elements divides the current paths into two separate groups. In some embodiments, pairs or quartets of the individual loop elements of the crossed wire groups are separately excited. This creates a phased array for excitation and for detection. In some embodiments, isolation is accomplished using isolation amplifiers to excite the transmit elements or read out currents from the receive elements of the surface coils.

In some embodiments, the present invention then includes a testing phase, in which various combinations of surface-coil elements and pulse sequencing of the different combinations are iteratively modified and tested to select among the designs and the strategies developed in the first two phases of the work to test prototypes of the crossed-wire resonator configurations.

In some embodiments, the present invention provides novel high-isolation transmit/receive surface coils for EPR imaging and measurement of biological tissue. The inventor believes there are no such EPR surface coils in use and in the literature, and that no such MRI coils exist either. In some embodiments, this technology enhances the signal-to-noise ratio (SNR) by three orders of magnitude relative to normal surface coil technology and should be of interest in the generally MRI community.

REFERENCES

{1.} Hall, E. J.; Radiobiology for the Radiologist, Edn. Fifth. (Lippincott Williams & Wilkins, Philadelphia; 2000). (Reference #1012 in the text above.)

{2.} Gatenby, R. A. et al.; Oxygen distribution in squamous cell carcinoma metastases and its relationship to outcome of radiation therapy. *Int. J. Radiat. Oncol. Biol. Phys.* 14, 831-838 (1988). (Reference #21 in the text above.)

{3.} Brizel, D. et al.; Tumor oxygenation predicts for the likelihood of distant metastases in human soft tissue sarcoma. *Cancer Res* 56, 941-943 (1996). (Reference #695 in the text above.)

{4.} Brizel, D. M., Dodge, R. K., Clough, R. W. & Dewhirst, M. W.; Oxygenation of head and neck cancer: changes during radiotherapy and impact on treatment outcome. *Radiother Oncol* 53, 113-117. (1999). (Reference #1121 in the text above.)

{5.} Brizel, D. M. et al.; Tumor oxygenation predicts for the likelihood of distant metastases in human soft tissue sarcoma. *Cancer Res* 56, 941-943. (1996). (Reference #1124 in the text above.)

{6.} Brizel, D. M., Sibley, G. S., Prosnitz, L. R., Scher, R. L. & Dewhirst, M. W.; Tumor hypoxia adversely affects the prognosis of carcinoma of the head and neck. *Int J Radiat Oncol Biol Phys* 38, 285-289. (1997). (Reference #1123 in the text above.)

{7.} Hockel, M. et al.; Association between tumor hypoxia and malignant progression in advanced cancer of the uterine cervix. *Cancer Res* 56, 4509-4515. (1996). (Reference #1111 in the text above.)

{8.} Shibata, T., Giaccia, A. J. & Brown, J. M.; Hypoxia-inducible regulation of a prodrug-activating enzyme for tumor-specific gene therapy. *Neoplasia* 4, 40-48 (2002). (Reference #1657 in the text above.)

{9.} Graeber, T. G. et al.; Hypoxia-mediated selection of cells with diminished apoptotic potential in solid tumours. *Nature* 379, 88-91 (1996). (Reference #942 in the text above.)

{10.} Semenza, G. L.; Hypoxia-inducible factor 1: master regulator of $O_2$ homeostasis. *Curr Opin Genet Dev* 8, 588-594 (1998). (Reference #1693 in the text above.)

{11.} Carmeliet, P. et al.; Role of HIF-1alpha in hypoxia-mediated apoptosis, cell proliferation and tumour angiogenesis. *Nature* 394, 485-490. (1998). (Reference #1132 in the text above.)

{12.} Elas, M. et al.; Electron paramagnetic resonance oxygen images correlate spatially and quantitatively with Oxylite oxygen measurements. *Clin Cancer Res* 12, 4209-4217 (2006). (Reference #1906 in the text above.)

{13.} Elas, M. et al.; Electron paramagnetic resonance oxygen image hypoxic fraction plus radiation dose strongly correlates with tumor cure in FSa fibrosarcomas. *Int J Radiat Oncol Biol Phys* 71, 542-549 (2008). (Reference #2117 in the text above.)

{14.} Alberts, B. et al.; Molecular Biology of the Cell, Edn. 5th. (Garland Science, New York, Milton Park UK; 2008). (Reference #2096 in the text above.)

{15.} Fischbach, C. et al.; Cancer cell angiogenic capability is regulated by 3D culture and integrin engagement. *Proc Natl Acad Sci USA* (2009). (Reference #2089 in the text above.)

{16.} Alam, J. & Cook, J. L.; Reporter genes: application to the study of mammalian gene transcription. *Anal Biochem* 188, 245-254 (1990). (Reference #1662 in the text above.)

{17.} Holt, S. J. & Sadler, P. W.; Studies in enzyme cytochemistry. II. Synthesis of indigogenic substrates for esterases. *Proc R Soc Lond B Biol Sci* 148, 481-494 (1958). (Reference #1663 in the text above.)

{18.} Chalfie, M., Tu, Y., Euskirchen, G., Ward, W. W. & Prasher, D. C.; Green fluorescent protein as a marker for gene expression. *Science* 263, 802-805 (1994). (Reference #1664 in the text above.)

{19.} Weissleder, R. & Ntziachristos, V.; Shedding light onto live molecular targets. *Nat Med* 9, 123-128 (2003). (Reference #1694 in the text above.)

{20.} McCaffrey, A., Kay, M. A. & Contag, C. H.; Advancing molecular therapies through in vivo bioluminescent imaging. *Mol Imaging* 2, 75-86 (2003). (Reference #1692 in the text above.)

{21.} Blasberg, R. G.; In vivo molecular-genetic imaging: multi-modality nuclear and optical combinations. *Nucl Med Biol* 30, 879-888 (2003). (Reference #1681 in the text above.)

{22.} Massoud, T. F. & Gambhir, S. S.; Molecular imaging in living subjects: seeing fundamental biological processes in a new light. *Genes Dev* 17, 545-580 (2003). (Reference #1687 in the text above.)

{23.} Herschman, H. R.; Molecular imaging: looking at problems, seeing solutions. *Science* 302, 605-608 (2003). (Reference #1684 in the text above.)

{24.} Dothager, R. S. & Piwnica-Worms, D.; Molecular imaging of pulmonary disease in vivo. *Proc Am Thorac Soc* 6, 403-410 (2009). (Reference #2227 in the text above.)

{25.} Zhang, W. et al.; Rapid in vivo functional analysis of transgenes in mice using whole body imaging of luciferase expression. *Transgenic Res* 10, 423-434 (2001). (Reference #1695 in the text above.)

{26.} Adams, J. Y. et al.; Visualization of advanced human prostate cancer lesions in living mice by a targeted gene transfer vector and optical imaging. *Nat Med* 8, 891-897 (2002). (Reference #1680 in the text above.)

{27.} Kirkpatrick, J. P., Oleson, J. R. & Dewhirst, M. W.; in Radiation ResearchSt. Louis, Mo., USA; 2004). (Reference #1691 in the text above.)

{28.} Dewhirst, M. W. et al.; Microvascular studies on the origins of perfusion-limited hypoxia. *Br J Cancer Suppl* 27, S247-251 (1996). (Reference #1775 in the text above.)

{29.} Schober, O., Rahbar, K. & Riemann, B.; Multimodality molecular imaging—from target description to clinical studies. *Eur J Nucl Med Mol Imaging* (2009). (Reference #2099 in the text above.)

{30.} Sun, X. et al.; Quantitative imaging of gene induction in living animals. *Gene Ther* 8, 1572-1579 (2001). (Reference #1374 in the text above.)

{31.} Blasberg, R. G. & Tjuvajev, J. G.; Molecular-genetic imaging: current and future perspectives. *J Clin Invest* 111, 1620-1629 (2003). (Reference #1665 in the text above.)

{32.} Beekman, F. & van der Have, F.; The pinhole: gateway to ultra-high-resolution three-dimensional radionuclide imaging. *Eur J Nucl Med Mol Imaging* 34, 151-161 (2007). (Reference #2100 in the text above.)

{33.} Raleigh, J. et al.; Development of an ELISA for the detection of 2-nitroimidazole hypoxia markers bound to tumor tissue. *Int J Radiat Oncol Biol Phys* 22, 403-405 (1992). (Reference #765 in the text above.)

{34.} Evans, S. M., Jenkins, W. T., Joiner, B., Lord, E. M. & Koch, C. J.; 2-Nitroimidazole (EF5) binding predicts radiation resistance in individual 9L s.c. tumors. *Cancer Res.* 56, 405-411 (1996). (Reference #931 in the text above.)

{35.} Lewis, J. S., McCarthy, D. W., McCarthy, T. J., Fujibayashi, Y. & Welch, M. J.; Evaluation of 64Cu-ATSM in vitro and in vivo in a hypoxic tumor model. *J Nucl Med* 40, 177-183 (1999). (Reference #1371 in the text above.)

{36.} Melo, T., Ballinger, J. R. & Rauth, A. M.; Role of NADPH:cytochrome P450 reductase in the hypoxic accumulation and metabolism of BRU59-21, a technetium-99m-nitroimidazole for imaging tumor hypoxia. *Biochem Pharmacol* 60, 625-634 (2000). (Reference #2229 in the text above.)

{37.} Louie, A. Y. et al.; In vivo visualization of gene expression using magnetic resonance imaging. *Nat Biotechnol* 18, 321-325 (2000). (Reference #1395 in the text above.)

{38.} Weissleder, R. et al.; In vivo magnetic resonance imaging of transgene expression. *Nat Med* 6, 351-355 (2000). (Reference #1673 in the text above.)

{39.} Vaughan, J. T. et al.; Whole-body imaging at 7T: preliminary results. *Magn Reson Med* 61, 244-248 (2009). (Reference #2230 in the text above.)

{40.} Halpern, H. J. et al.; An imaging radiofrequency electron spin resonance spectrometer with high resolution and sensitivity for in vivo measurements. *Rev. Sci. Instrum.* 60, 1040-1050 (1989). (Reference #89 in the text above.)

{41.} Halpern, H. J. & Bowman, M. K. (eds.); EPR Imaging at MHz frequencies. (CRC Press, Boca Raton, Fla.; 1991). (Reference #899 in the text above.)

{42.} Halpern, H. J. in In Vivo EPR(ESR): Theory and Applications, Vol. 18. (ed. L. J. Berliner) (Kluwer Academic/Plenum Pub Corp, New York; 2003). (Reference #1798 in the text above.)

{43.} Lauterbur, P. C., Levin, D. N. & Marr, R. B.; Theory and simulation of NMR spectroscopic imaging and field plotting by projection reconstruction involving an intrinsic frequency dimension. *J. Magn. Reson.* 59, 536-541 (1984). (Reference #177 in the text above.)

{44.} Maltempo, M. M.; Differentiation of spectral and spatial components in EPR imaging using 2-D image reconstruction algorithms. *J. Magn. Reson.* 69, 156-161 (1986). (Reference #181 in the text above.)

{45.} Halpern, H. J. et al.; Oxymetry deep in tissues with low-frequency electron paramagnetic resonance. *Proc. Natl. Acad. Sci. USA* 91, 13047-13051 (1994). (Reference #93 in the text above.)

{46.} Epel, B., Sundramoorthy, S. V., Mailer, C. & Halpern, H. J.; A versatile high speed 250-MHz pulse imager for biomedical applications. *Concept Magn Reson B* 33B, 163-176 (2008). (Reference #2200 in the text above.)

{47.} Haney, C. R. et al.; Characterization of response to radiation mediated gene therapy by means of multimodality imaging. *Magn Reson Med* 62, 348-356 (2009). (Reference #2194 in the text above.)

{48.} Colton, T.; Statistics in Medicine. (Little, Brown &Co., Boston; 1974). (Reference #1724 in the text above.)

{49.} Shibata, T., Giaccia, A. J. & Brown, J. M.; Development of a hypoxia-responsive vector for tumor-specific gene therapy. *Gene Ther* 7, 493-498 (2000). (Reference #1659 in the text above.)

{50.} Wilson, S. R., Gallagher, S., Warpeha, K. & Hawthorne, S. J.; Amplification of MMP-2 and MMP-9 production by prostate cancer cell lines via activation of protease-activated receptors. *Prostate* 60, 168-174 (2004). (Reference #2083 in the text above.)

{51.} Mechtcheriakova, D., Wlachos, A., Holzmuller, H., Binder, B. R. & Hofer, E.; Vascular endothelial cell growth factor-induced tissue factor expression in endothelial cells is mediated by EGR-1. *Blood* 93, 3811-3823 (1999). (Reference #2087 in the text above.)

{52.} Castro, B., Dormoy, J. R., Evin, G. & Selve, C.; Reactions of Peptide Bond 4. Benzotriazonyl-N-Oxytridimelthylamino Phosphonium Hexafluorophosphate (Bop). *Tetrahedron Lett,* 1219-1222 (1975). (Reference #2093 in the text above.)

{53.} Bremer, C., Bredow, S., Mahmood, U., Weissleder, R. & Tung, C. H.; Optical imaging of matrix metalloproteinase-2 activity in tumors: feasibility study in a mouse model. *Radiology* 221, 523-529 (2001). (Reference #1407 in the text above.)

{54.} Rosen, G. M. et al.; Dendrimeric-containing nitronyl nitroxides as spin traps for nitric oxide: Synthesis, kinetic and stability studies. *Macromolecules* 36, 1021-1027 (2003). (Reference #1548 in the text above.)

{55.} Alberts, B. et al.; Molecular Biology of the Cell, Edn. 3rd. (Garland, New York; 1994). (Reference #40 in the text above.)

{56.} Halpern, H. J. et al.; Selective isotopic labeling of a nitroxide spin label to enhance sensitivity for T2 oxymetry. *J. Magn. Reson.* 90, 40-51 (1990). (Reference #850 in the text above.)

{57.} Halpern, H. J., Peric, M., Yu, C. & Bales, B. L.; Rapid quantitation of parameters from inhomogeneously broadened EPR spectra. *J. Magn. Reson. A*103, 13-22 (1993). (Reference #91 in the text above.)

{58.} Fink, T., Kazlauskas, A., Poellinger, L., Ebbesen, P. & Zachar, V.; Identification of a tightly regulated hypoxia-response element in the promoter of human plasminogen activator inhibitor-1. *Blood* 99, 2077-2083 (2002). (Reference #1676 in the text above.)

{59.} Stephen, R. M. & Gillies, R. J.; Promise and progress for functional and molecular imaging of response to targeted therapies. *Pharm Res* 24, 1172-1185 (2007). (Reference #2084 in the text above.)

{60.} Gillespie, D. L. et al.; Silencing of hypoxia inducible factor-1alpha by RNA interference attenuates human glioma cell growth in vivo. *Clin Cancer Res* 13, 2441-2448 (2007). (Reference #2085 in the text above.)

{61.} Lungu, G. F., Li, M. L., Xie, X., Wang, L. V. & Stoica, G.; In vivo imaging and characterization of hypoxia-induced neovascularization and tumor invasion. *Int J Oncol* 30, 45-54 (2007). (Reference #2086 in the text above.)

{62.} Schabbauer, G. et al.; Nuclear factor of activated T cells and early growth response-1 cooperate to mediate tissue factor gene induction by vascular endothelial growth factor in endothelial cells. *Thromb Haemost* 97, 988-997 (2007). (Reference #2095 in the text above.)

{63.} Timke, C. et al.; Combination of vascular endothelial growth factor receptor/platelet-derived growth factor receptor inhibition markedly improves radiation tumor therapy. *Clin Cancer Res* 14, 2210-2219 (2008). (Reference #2091 in the text above.)

{64.} Pourgholami, M. H. & Morris, D. L.; Inhibitors of vascular endothelial growth factor in cancer. *Cardiovasc Hematol Agents Med Chem* 6, 343-347 (2008). (Reference #2088 in the text above.)

{65.} Burks, S. R. et al.; 2H,15N-Substituted nitroxides for measuring oxygen concentration: Implications for in vivo oxymetry using electron paramagnetic resonance imaging. *Magn Reson Med* Submitted (2009). (Reference #2081 in the text above.)

{66.} Lin, Y. J., Teicher, B. A. & Halpern, H. J.; Synthesis of 4-proto-3-carbamoyl-2,2,5,5-tetraperdeuteromethyl-3-pyrrolin-1-xsloyxy (mHCTPO): A selectively isotopically labeled compound for use in T2 spin label oxymetry. *J. Labelled Comp. Radiopharmaceut.* 28, 621-631 (1990). (Reference #118 in the text above.)

{67.} Burks, S. R. et al.; Optimization of labile esters for esterase-assisted accumulation of nitroxides into cells: a model for in vivo EPR imaging. *Bioconjug Chem* 19, 2068-2071 (2008). (Reference #2101 in the text above.)

{68.} Haney, C. R. et al.; Reduction of image artifacts in mice by bladder flushing with a novel double-lumen urethral catheter. *Mol Imaging* 5, 175-179 (2006). (Reference #1876 in the text above.)

{69.} Wells, W. M., 3rd, Viola, P., Atsumi, H., Nakajima, S. & Kikinis, R.; Multi-modal volume registration by maximization of mutual information. *Med Image Anal* 1, 35-51. (1996). (Reference #1214 in the text above.)

{70.} Studholme, C., Hill, D. L. & Hawkes, D. J.; Automated 3-D registration of MR and CT images of the head. *Med Image Anal* 1, 163-175. (1996). (Reference #1215 in the text above.)

{71.} Studholme, C., Hill, D. L. & Hawkes, D. J.; Automated three-dimensional registration of magnetic resonance and positron emission tomography brain images by multiresolution optimization of voxel similarity measures. *Med Phys* 24, 25-35. (1997). (Reference #1216 in the text above.)

{72.} Thurston, G. & Kitajewski, J.; VEGF and Delta-Notch: interacting signalling pathways in tumour angiogenesis. *Br J Cancer* 99, 1204-1209 (2008). (Reference #2090 in the text above.)

In some embodiments, the present invention provides an apparatus for electron paramagnetic resonance imaging (EPRI) of a volume of animal tissue in vivo. This apparatus includes: a set of RF transmit coils; and a set of RF receive coils, wherein the set of surface transmit coils generates an RF excitation magnetic field in the volume of animal tissue in response to an applied electrical signal, and the set of surface receive coils generates a sensed electrical signal in response to a sensed RF magnetization in the volume of animal tissue, and wherein the set of transmit coils and the set of receive coils are oriented relative to one another such that the sensed magnetization has a reduced component directly due to the excitation magnetic field. In some embodiments, the set of receive coils is configured to detect electron paramagnetic resonance signals in the volume of animal tissue.

Some embodiments of the apparatus (see, e.g., FIG. 18F) further include a main-and-gradient magnetic-field generator (e.g., 141) configured to generate a substantially static magnetic field (e.g., 140) in the volume of animal tissue, wherein the static magnetic field has a direction that is generally orthogonal to the RF excitation magnetic field and to the sensed RF magnetization in the volume of animal tissue, wherein the static magnetic field has a gradient field strength (e.g., 140F), and wherein the RF excitation magnetic field (e.g., 131) is generally orthogonal to the sensed RF magnetization in the volume of animal tissue; an RF frequency electrical pulse generation circuit (e.g., 151) operatively coupled to the set of surface transmit coils (e.g., 134, 135); an RF receiver circuit (e.g., 152) operatively coupled to the set of surface receive coils (e.g., 136, 137) to receive the sensed electrical signal (e.g., 142) from the set of surface receive coils and to generate a received electrical signal (e.g., 143); a digital-signal processor (DSP) unit (e.g., 154) operatively coupled to the RF receiver circuit (e.g., 152) and configured to process the received electrical signal (e.g., 143) and to generate image data (e.g., data 144 optionally generated using image-generation circuit 155); a storage unit (e.g., 156) operatively coupled to the DSP unit to receive and store the image data (e.g., 144); and a display unit (e.g., 157) operatively coupled to the storage unit (e.g., 156) to receive and display the image data (e.g., 144).

In some embodiments, the DSP unit (e.g., 154-155) performs image reconstruction by filtered backprojection inverse Radon transformation of frequency information obtained by Fourier transformation of time-domain signal for a plurality of different gradient directions (e.g., directions 140E of FIG. 18E, 140F of FIG. 18F, and 140G of FIG. 18G) to obtain spatial information (e.g., in some embodiments, EPR signal strength (e.g., See FIG. 3A) and/or EPR spectrum information such as linewidths or the like) for a plurality of voxels in a three-dimensional configuration.

In some embodiments, the RF excitation magnetic field is pulsed and has a carrier frequency of no more than about 500 MHz, and the sensed electrical signal represents a signal strength (e.g., See FIG. 3A) of an electron paramagnetic spin characteristic of at least one chemical species. In other embodiments, RF excitation magnetic field is pulsed and has a carrier frequency of no more than about 100 MHz; no more than about 200 MHz; no more than about 500 MHz; no more than about 300 MHz; or no more than about 400 MHz. In yet other embodiments, RF excitation magnetic field is pulsed and has a carrier frequency of no more than about 600 MHz; no more than about 700 MHz; no more than about 800 MHz; no more than about 900 MHz; or no more than about 1000 MHz. In some embodiments, frequencies at the lower end (e.g., no more than about 300 MHz) of these frequencies preferred since there is better tissue penetration and less tissue heating. In some embodiments, the RF excitation magnetic field is pulsed and has a carrier frequency of about 225 MHz. In some embodiments, the RF excitation magnetic field is pulsed and has a carrier frequency of about 250 MHz. In some embodiments, the RF excitation magnetic field is pulsed and has a carrier frequency of about 275 MHz. In some embodiments, the RF excitation magnetic field is pulsed and has a carrier frequency of about 300 MHz.

In some embodiments, the RF excitation magnetic field is pulsed and has a carrier frequency of no more than about 500 MHz, and the sensed electrical signal represents a electron paramagnetic spin spectrum (e.g., See FIG. 3B) of at least one chemical species.

In some embodiments, the set of RF transmit coils and the set of RF receive coils are arranged in a surface-volume configuration (e.g., See FIG. 1C, FIGS. 17A-17D5, and FIGS. 18A-17D2).

In some embodiments, the set of RF transmit coils (e.g., see FIG. 1C) includes a first transmit loop (e.g., 162) and a second transmit loop (e.g., 164), wherein the first transmit loop (e.g., 162) is positioned on a first surface (e.g., 172) having a first surface normal vector (e.g., 92) at a generally center location on the first surface (e.g., 172) within a periphery of the first transmit loop (e.g., 162), wherein the second transmit loop (e.g., 164) is positioned on a second surface (e.g., 174) having a second surface normal vector (e.g., 94) at a center location on the second surface (e.g., 174) within a periphery of the second transmit loop (e.g., 164), and wherein the first surface normal vector (e.g., 92) and the second surface normal vector (e.g., 94) define a first plane; wherein the set of RF receive coils includes a first receive loop (e.g., 161) and a second receive loop (e.g., 163), wherein the first receive loop (e.g., 161) is positioned on a third surface (e.g., 171) having a third surface normal vector (e.g., 91) at a center location on the third surface (e.g., 171) within a periphery of the first receive loop (e.g., 161), wherein the second receive loop (e.g., 163) is positioned on a fourth surface (e.g., 173) having a fourth surface normal vector (e.g., 93) at a center location on the fourth surface (e.g., 173) within a periphery of the second receive loop (e.g., 163), and wherein the third surface normal vector (e.g., 91) and the fourth surface normal vector (e.g., 93) define a second plane; and wherein the first plane is orthogonal to the second plane, and a line (e.g., 90) defined by the intersection of the first plane and the second plane forms an acute angle (the angle between vector 90 and 92) to the first normal vector, forms an acute angle (the angle between vector 90 and 94) to the second normal vector, forms an acute angle (the angle between vector 90 and 91) to the third normal vector, and forms an acute angle (the angle between vector 90 and 93) to the fourth normal vector.

In some embodiments, the apparatus is configured to obtain an electron paramagnetic resonance oxygen image (EPROI) of animal tissue at an RF frequency of no more than 300 MHz. In other embodiments, the RF frequency is between about 100 MHz and about 200 MHz. In other embodiments, the RF frequency is between about 200 MHz and about 300 MHz. In other embodiments, the RF frequency is about 250 MHz. In other embodiments, the RF frequency is between about 300 MHz and about 400 MHz. In other embodiments, the RF frequency is between about 400 MHz and about 500 MHz. In other embodiments, the RF frequency is between about 500 MHz and about 600 MHz. In other embodiments, the RF frequency is between about 600 MHz and about 700 MHz. In other embodiments, the RF frequency is between about 700 MHz and about 800 MHz. In other embodiments, the RF frequency is between about 800 MHz and about 900 MHz. In other embodiments, the RF frequency is between about 900 MHz and about 1000 MHz. In some embodiments, the lower RF frequencies (e.g., no more than about 300 MHz) are preferred because the RF energy penetrates human tissue with less heating than if higher frequencies are used. Conventionally RF frequencies above 1000 MHz (1 GHz) were used for EPR, making EPR impractical for imaging human tissue in vivo. In some embodiments, the strength of the static magnetic field and the RF frequency used are chosen such that the RF frequency matches the Larmor frequency for electron paramagnetic resonance at that field strength.

In some embodiments, the present invention provides a method for electron paramagnetic resonance imaging (EPRI) of a volume of animal tissue in vivo in an animal. This method includes generating a substantially static magnetic field in the volume of animal tissue, wherein the static magnetic field has a direction; generating an RF excitation magnetic field in a direction generally orthogonal to the direction of the substantially static magnetic field in the volume of animal tissue from a first surface next to the volume of animal tissue; sensing an RF magnetization in a direction generally orthogonal to the direction of the substantially static magnetic field in the volume of animal tissue from a second surface next to the volume of animal tissue, wherein the sensed RF magnetization is in a direction generally orthogonal to the pulsed excitation magnetic field; generating a received electrical signal based on the sensed RF magnetic field; digitally signal processing the received electrical signal to generate image data using a computer; storing the image data using the computer; and displaying the stored image data on a computer monitor.

In some embodiments of the method, the digitally signal processing of the received electrical signal includes Fourier transforming time to frequency information for a plurality of different gradient directions to obtain spatial EPR signal strength for a plurality of voxels in a three-dimensional configuration.

In some embodiments, the digitally signal processing of the received electrical signal includes Fourier transforming time domain signals to obtain frequency information; and filtered backprojection inverse Radon transforming of frequency information obtained from the Fourier transforming of the time domain signals for a plurality of different gradient directions to obtain spatial information (e.g., in some embodiments, EPR signal strength and/or EPR spectrum information such as linewidths or the like) for a plurality of voxels in a three-dimensional configuration.

In some embodiments of the method, the RF excitation magnetic field is pulsed and has a carrier frequency of no more than about 500 MHz, and the sensed electrical signal represents a signal strength of an electron paramagnetic spin characteristic of at least one chemical species.

In some embodiments of the method, the RF excitation magnetic field is pulsed and has a carrier frequency of no more than about 500 MHz, and the sensed electrical signal represents a electron paramagnetic spin spectrum of at least one chemical species.

In some embodiments of the method, the generating of the RF excitation magnetic field includes coupling an electrical RF pulse to a set of RF transmit coils and the sensing of the RF magnetization includes receiving an electrical signal from a set of RF receive coils, and wherein the set of RF transmit coils and the set of RF receive coils are arranged in a surface-volume configuration.

In some embodiments of the method, the set of RF transmit coils includes a first transmit loop and a second transmit loop, wherein the first transmit loop is positioned on a first surface having a first surface normal vector at a generally center location on the first surface within a periphery of the first transmit loop, wherein the second transmit loop is positioned on a second surface having a second surface normal vector at a center location on the second surface within a periphery of the second transmit loop, and wherein the first surface normal vector and the second surface normal vector define a first plane; the set of RF receive coils includes a first receive loop and a second receive loop, wherein the first receive loop is positioned on a third surface having a third surface normal vector at a center location on the third surface within a periphery of the first receive loop, wherein the second receive loop is positioned on a fourth surface having a fourth surface normal vector at a center location on the fourth surface within a periphery of the second receive loop, and wherein the third surface normal vector and the fourth surface normal vector define a second plane; and the first plane is orthogonal to the second plane, and a line defined by the intersection of the first plane and the second plane forms an acute angle to the first normal vector, forms an acute angle to the second normal vector, forms an acute angle to the third normal vector, and forms an acute angle to the fourth normal vector.

In some embodiments, the present invention provides an apparatus for electron paramagnetic resonance imaging (EPRI) of a volume of animal tissue in vivo. This apparatus includes: means for generating a substantially static magnetic field (e.g., 141 of FIG. 18E) in the volume of animal tissue, wherein the static magnetic field has a direction; means for generating an RF excitation magnetic field (e.g., 151, 134, 135 of FIG. 18E) in a direction generally orthogonal to the direction of the substantially static magnetic field in the volume of animal tissue from a first surface next to the volume of animal tissue; means for sensing an RF magnetization (e.g., 152, 136, 137 of FIG. 18E) in a direction generally orthogonal to the direction of the substantially static magnetic field in the volume of animal tissue from a second surface next to the volume of animal tissue, wherein the sensed RF magnetization is in a direction generally orthogonal to the pulsed excitation magnetic field; means for generating a received electrical signal (e.g., 152 of FIG. 18E) based on the sensed RF magnetic field; means for digitally signal processing (e.g., 153, 154 of FIG. 18E) the received electrical signal to generate image data; means for storing (e.g., 156 of FIG. 18E) the image data; and means for displaying (e.g., 157 of FIG. 18E) the stored image data.

In some embodiments of the apparatus, the means for digitally signal processing of the received electrical signal includes means for Fourier transforming time to frequency information for a plurality of different gradient directions to obtain spatial EPR signal strength for a plurality of voxels in a three-dimensional configuration.

In some embodiments, the means for digitally signal processing of the received electrical signal includes means for Fourier transforming time domain signals to obtain frequency information; and means for filtered backprojection inverse Radon transforming of frequency information obtained from the means for Fourier transforming of time domain signals for a plurality of different gradient directions to obtain spatial information (e.g., EPR signal strength and/or EPR spectrum information such as linewidths or the like) for a plurality of voxels in a three-dimensional configuration.

In some embodiments of the apparatus, the RF excitation magnetic field is pulsed and has a carrier frequency of no more than about 500 MHz, and the sensed electrical signal represents a signal strength of an electron paramagnetic spin characteristic of at least one chemical species.

In some embodiments of the apparatus, the RF excitation magnetic field is pulsed and has a carrier frequency of no more than about 500 MHz, and the sensed electrical signal represents a electron paramagnetic spin spectrum of at least one chemical species.

In some embodiments of the apparatus, the means for generating of the RF excitation magnetic field includes a set of RF transmit coils and the means for sensing of the RF magnetization includes a set of RF receive coils, and wherein the set of RF transmit coils and the set of RF receive coils are arranged in a surface-volume configuration.

In some embodiments of the apparatus, the set of RF transmit coils includes a first transmit loop and a second transmit loop, wherein the first transmit loop is positioned on a first surface having a first surface normal vector at a generally center location on the first surface within a periphery of the first transmit loop, wherein the second transmit loop is positioned on a second surface having a second surface normal vector at a center location on the second surface within a periphery of the second transmit loop, and wherein the first surface normal vector and the second surface normal vector define a first plane; the set of RF receive coils includes a first receive loop and a second receive loop, wherein the first receive loop is positioned on a third surface having a third surface normal vector at a center location on the third surface within a periphery of the first receive loop, wherein the second receive loop is positioned on a fourth surface having a fourth surface normal vector at a center location on the fourth surface within a periphery of the second receive loop, and wherein the third surface normal vector and the fourth surface normal vector define a second plane; and the first plane is orthogonal to the second plane, and a line defined by the intersection of the first plane and the second plane forms an acute angle to the first normal vector, forms an acute angle to the second normal vector, forms an acute angle to the third normal vector, and forms an acute angle to the fourth normal vector.

Environments for Some Embodiments

In some embodiments, a digital processing system or computer system includes a processor, which may represent one or more processors and may include one or more conventional types of such processors (e.g., x86, x86-64), such as an AMD processor, or Intel Pentium processor or the like. A memory is coupled to the processor by a bus. The memory may be a dynamic random access memory (DRAM) and/or may include static RAM (SRAM). The processor may also be coupled to other types of storage areas/memories (e.g., cache, Flash memory, disk, etc.), which could be considered as part of the memory or separate from the memory.

The bus further couples the processor to a display controller, a mass memory or some type of computer-readable medium device, the modem or network interface, and an input/output (I/O) controller. Computer-readable medium may include a magnetic, optical, magneto-optical, tape, and/or other type of machine-readable medium/device for storing information. For example, the computer-readable medium may represent a hard disk, a read-only or writeable optical CD, etc. The display controller controls in a conventional manner a display, which may represent a cathode ray tube (CRT) display, a liquid crystal display (LCD), a plasma display, or other type of display device. The I/O controller controls I/O device(s), which may include one or more keyboards, mouse/trackball or other pointing devices, magnetic and/or optical disk drives, printers, scanners, digital cameras, microphones, etc.

In some embodiments, the system includes a plurality of computers that are interconnected by local networks, private long-distance networks, virtual private networks or the internet (e.g., using the secure socket facilities of the software). In some embodiments, the system is controlled by computer program instructions stored on a computer-readable medium.

In some embodiments, the present invention may be implemented as a computer-readable medium having stored thereon executable computer program instructions that when executed on a suitable computer and/or other hardware perform a method according to the present invention or that make the computer and/or other hardware into a special-purpose machine, or, in other embodiments, may be implemented in a combination of software and hardware, or in certain embodiments, entirely in hardware.

Embodiments within the scope of the present invention include a computer-readable medium for carrying or having computer-executable instructions or data structures stored thereon. Such computer-readable medium may be any available medium, which is accessible by a general-purpose or special-purpose computer system. By way of example, and not limitation, such computer-readable medium can comprise physical storage medium such as RAM, ROM, EPROM, CD-ROM or other optical-disk storage, magnetic-disk storage or other magnetic-storage devices, EEPROM or FLASH storage devices, or any other medium which can be used to carry or store desired program code means in the form of computer-executable instructions, computer-readable instructions, or data structures and which may be accessed by a general-purpose or special-purpose computer system. This physical storage medium may be fixed to the computer system as in the case of a magnetic drive or removable as in the case of an EEPROM device (e.g., FLASH storage device).

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus for electron paramagnetic resonance imaging (EPRI) of a volume of animal tissue in vivo, the apparatus comprising:
    a set of RF transmit coils; and
    a set of RF receive coils,
    wherein the set of transmit coils generates an excitation RF magnetic field in the volume of animal tissue in response to an applied electrical signal, and the set of receive coils generates a sensed electrical signal in response to a sensed RF magnetization in the volume of animal tissue;
    wherein the set of transmit coils and the set of receive coils are oriented relative to one another such that the sensed magnetization has a reduced component directly due to the excitation magnetic field;
    wherein the set of receive coils is configured to detect electron paramagnetic resonance signals in the volume of animal tissue;
    wherein the set of RF transmit coils includes a first transmit loop and a second transmit loop, wherein the first transmit loop is positioned on a first surface having a first surface normal vector at a generally center location on the first surface within a periphery of the first transmit loop, wherein the second transmit loop is positioned on a second surface having a second surface normal vector at a center location on the second surface within a periphery of the second transmit loop, and wherein the first surface normal vector and the second surface normal vector define a first plane;
    wherein the set of RF receive coils includes a first receive loop and a second receive loop, wherein the first receive loop is positioned on a third surface having a third surface normal vector at a center location on the third surface within a periphery of the first receive loop, wherein the second receive loop is positioned on a fourth surface having a fourth surface normal vector at a center location on the fourth surface within a periphery of the second receive loop, and wherein the third surface normal vector and the fourth surface normal vector define a second plane; and
    wherein the first plane is orthogonal to the second plane, and a line defined by the intersection of the first plane and the second plane forms an acute angle to the first normal vector, forms an acute angle to the second normal vector, forms an acute angle to the third normal vector, and forms an acute angle to the fourth normal vector.

2. The apparatus of claim 1, further comprising:
    a main-and-gradient magnetic-field generator configured to generate a substantially static magnetic field in the volume of animal tissue, wherein the static magnetic field has a direction that is generally orthogonal to the RF excitation magnetic field and to the sensed RF magnetization in the volume of animal tissue, wherein the static magnetic field has a gradient field strength, and wherein the RF excitation magnetic field is generally orthogonal to the sensed RF magnetization in the volume of animal tissue;
    an RF electrical pulse generation circuit operatively coupled to the set of RF transmit coils;
    an RF receiver circuit operatively coupled to the set of RF receive coils to receive the sensed electrical signal from the set of RF receive coils and to generate a received electrical signal;
    a digital-signal processor (DSP) unit operatively coupled to the RF receiver circuit and configured to process the received electrical signal and to generate image data;
    a storage unit operatively coupled to the DSP unit to receive and store the image data; and
    a display unit operatively coupled to the storage unit to receive and display the image data.

3. The apparatus of claim 2, wherein the DSP unit performs image reconstruction by filtered backprojection inverse Radon transformation of frequency information obtained by Fourier transformation of time domain signal for a plurality of different gradient directions to obtain spatial EPR signal strength for a plurality of voxels in a three-dimensional configuration.

4. The apparatus of claim 1, wherein the RF excitation magnetic field is pulsed and has a carrier frequency of no more than about 500 MHz, and the sensed electrical signal represents a signal strength of an electron paramagnetic spin characteristic of at least one chemical species.

5. The apparatus of claim 1, wherein the RF excitation magnetic field is pulsed and has a carrier frequency of no more than about 500 MHz, and the sensed electrical signal represents a electron paramagnetic spin spectrum of at least one chemical species.

6. The apparatus of claim 1, wherein the set of RF transmit coils and the set of RF receive coils are arranged in a surface-volume configuration.

7. The apparatus of claim 1, wherein the apparatus is configured to obtain an electron paramagnetic resonance oxygen image (EPROI) of animal tissue at an RF frequency of no more than 300 MHz.

8. A method for electron paramagnetic resonance imaging (EPRI) of a volume of animal tissue in vivo in an animal, the method comprising:
    generating a substantially static magnetic field in the volume of animal tissue, wherein the static magnetic field has a direction;
    generating, with a set of RF transmit coils, an RF excitation magnetic field in a direction generally orthogonal to the direction of the substantially static magnetic field in the volume of animal tissue from a first surface next to the volume of animal tissue;
    sensing, with a set of RF receive coils, an RF magnetization in a direction generally orthogonal to the direction of the substantially static magnetic field in the volume of animal tissue from a second surface next to the volume of animal tissue, wherein the sensed RF magnetization is in a direction generally orthogonal to the pulsed excitation magnetic field;

generating a received electrical signal based on the sensed RF magnetic field;

digitally signal processing the received electrical signal to generate image data using a computer;

storing the image data using the computer; and displaying the stored image data on a computer monitor;

wherein the set of RF transmit coils includes a first transmit loop and a second transmit loop, wherein the first transmit loop is positioned on a first surface having a first surface normal vector at a generally center location on the first surface within a periphery of the first transmit loop, wherein the second transmit loop is positioned on a second surface having a second surface normal vector at a center location on the second surface within a periphery of the second transmit loop, and wherein the first surface normal vector and the second surface normal vector define a first plane;

wherein the set of RF receive coils includes a first receive loop and a second receive loop, wherein the first receive loop is positioned on a third surface having a third surface normal vector at a center location on the third surface within a periphery of the first receive loop, wherein the second receive loop is positioned on a fourth surface having a fourth surface normal vector at a center location on the fourth surface within a periphery of the second receive loop, and wherein the third surface normal vector and the fourth surface normal vector define a second plane; and wherein the first plane is orthogonal to the second plane, and a line defined by the intersection of the first plane and the second plane forms an acute angle to the first normal vector, forms an acute angle to the second normal vector, forms an acute angle to the third normal vector, and forms an acute angle to the fourth normal vector.

9. The method of claim 8, wherein the digitally signal processing of the received electrical signal includes Fourier transforming time to frequency information for a plurality of different gradient directions to obtain spatial EPR signal strength for a plurality of voxels in a three-dimensional configuration.

10. The method of claim 8, wherein the RF excitation magnetic field is pulsed and has a carrier frequency of no more than about 500 MHz, and the sensed electrical signal represents a signal strength of an electron paramagnetic spin characteristic of at least one chemical species.

11. The method of claim 8, wherein the RF excitation magnetic field is pulsed and has a carrier frequency of no more than about 500 MHz, and the sensed electrical signal represents a electron paramagnetic spin spectrum of at least one chemical species.

12. The method of claim 8, wherein the generating of the RF excitation magnetic field includes coupling an electrical RF pulse to a set of RF transmit coils and the sensing of the RF magnetization includes receiving an electrical signal from a set of RF receive coils, and wherein the set of RF transmit coils and the set of RF receive coils are arranged in a surface-volume configuration.

13. An apparatus for electron paramagnetic resonance imaging (EPRI) of a volume of animal tissue in vivo in an animal, the apparatus comprising:

means for generating a substantially static magnetic field in the volume of animal tissue, wherein the static magnetic field has a direction;

means for generating an RF excitation magnetic field in a direction generally orthogonal to the direction of the substantially static magnetic field in the volume of animal tissue from a first surface next to the volume of animal tissue;

means for sensing an RF magnetization in a direction generally orthogonal to the direction of the substantially static magnetic field in the volume of animal tissue from a second surface next to the volume of animal tissue, wherein the sensed RF magnetization is in a direction generally orthogonal to the pulsed excitation magnetic field;

means for generating a received electrical signal based on the sensed RF magnetic field;

means for digitally signal processing the received electrical signal to generate image data;

means for storing the image data;

means for displaying the stored image data; and wherein the set of RF transmit coils includes a first transmit loop and a second transmit loop, wherein the first transmit loop is positioned on a first surface having a first surface normal vector at a generally center location on the first surface within a periphery of the first transmit loop, wherein the second transmit loop is positioned on a second surface having a second surface normal vector at a center location on the second surface within a periphery of the second transmit loop, and wherein the first surface normal vector and the second surface normal vector define a first plane;

wherein the set of RF receive coils includes a first receive loop and a second receive loop, wherein the first receive loop is positioned on a third surface having a third surface normal vector at a center location on the third surface within a periphery of the first receive loop, wherein the second receive loop is positioned on a fourth surface having a fourth surface normal vector at a center location on the fourth surface within a periphery of the second receive loop, and wherein the third surface normal vector and the fourth surface normal vector define a second plane; and wherein the first plane is orthogonal to the second plane, and a line defined by the intersection of the first plane and the second plane forms an acute angle to the first normal vector, forms an acute angle to the second normal vector, forms an acute angle to the third normal vector, and forms an acute angle to the fourth normal vector.

14. The apparatus of claim 13, wherein the means for digitally signal processing of the received electrical signal includes:

means for Fourier transforming time domain signals to obtain frequency information; and means for filtered backprojection inverse Radon transforming of frequency information obtained from the means for Fourier transforming of time domain signals for a plurality of different gradient directions to obtain spatial EPR signal strength for a plurality of voxels in a three-dimensional configuration.

15. The apparatus of claim 13, wherein the RF excitation magnetic field is pulsed and has a carrier frequency of no more than about 500 MHz, and the sensed electrical signal represents a signal strength of an electron paramagnetic spin characteristic of at least one chemical species.

16. The apparatus of claim 13, wherein the RF excitation magnetic field is pulsed and has a carrier frequency of no more than about 500 MHz, and the sensed electrical signal represents a electron paramagnetic spin spectrum of at least one chemical species.

17. The apparatus of claim 13, wherein the means for generating of the RF excitation magnetic field includes a set of RF transmit coils and the means for sensing of the RF magnetization includes a set of RF receive coils, and wherein the set of RF transmit coils and the set of RF receive coils are arranged in a surface-volume configuration.

18. The apparatus of claim 13, wherein the means for generating an RF excitation magnetic field include surface-volume coils, and wherein the means for sensing an RF magnetization include surface-volume coils.

19. The apparatus of claim 13, wherein the means for generating of the static magnetic field includes means for generating a gradient field strength in the static magnetic field.

20. The method of claim 8, wherein the generating of the static magnetic field includes generating a gradient field strength in the static magnetic field.

* * * * *